US011437583B2

(12) United States Patent
Kase et al.

(10) Patent No.: US 11,437,583 B2
(45) Date of Patent: Sep. 6, 2022

(54) ORGANIC ELECTROLUMINESCENCE DEVICE THAT INCLUDES COMPOUND HAVING BENZOAZOLE STRUCTURE

(71) Applicant: HODOGAYA CHEMICAL CO., LTD., Tokyo (JP)

(72) Inventors: Kouki Kase, Tokyo (JP); Naoaki Kabasawa, Tokyo (JP); Shunji Mochizuki, Tokyo (JP); Kazuyuki Suruga, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/636,599

(22) PCT Filed: Jul. 25, 2018

(86) PCT No.: PCT/JP2018/027928
§ 371 (c)(1),
(2) Date: Feb. 4, 2020

(87) PCT Pub. No.: WO2019/026728
PCT Pub. Date: Feb. 7, 2019

(65) Prior Publication Data
US 2020/0373500 A1    Nov. 26, 2020

(30) Foreign Application Priority Data
Aug. 4, 2017    (JP) .............................. JP2017-151855

(51) Int. Cl.
*H01L 51/00* (2006.01)
*H01L 51/42* (2006.01)
*H01L 51/50* (2006.01)

(52) U.S. Cl.
CPC ...... *H01L 51/0069* (2013.01); *H01L 51/0057* (2013.01); *H01L 51/0059* (2013.01);
(Continued)

(58) Field of Classification Search
CPC ............. H01L 51/0069; H01L 51/0059; H01L 51/0067; H01L 51/0072; H01L 51/0073; H01L 51/0074
(Continued)

(56) References Cited

U.S. PATENT DOCUMENTS 5,639,914 A    6/1997  Tomiyama et al.
5,707,747 A    1/1998  Tomiyama et al.
(Continued)

FOREIGN PATENT DOCUMENTS

CN    109790132 A    5/2019
EP    3 483 148 A1   5/2019
(Continued)

OTHER PUBLICATIONS

English Machine Translation of WO 2016/153283 (Year: 2016).*
(Continued)

*Primary Examiner* — Dzung Tran
(74) *Attorney, Agent, or Firm* — Birch, Stewart, Kolasch & Birch, LLP

(57) ABSTRACT

It is an object of the present invention to provide an organic EL device in which, as a highly efficient and highly durable organic EL material, various materials excelling in electron injection/transport performance, hole blocking performance, hole resistance performance, exciton confinement performance, stability in a film state, and durability, are combined so that properties of each material can be effectively demonstrated, thereby achieving (1) high light emission efficiency and power efficiency, (2) low luminescence starting voltage, (3) low practical driving voltage, and (4) particularly long lifetime.

An organic EL device including at least a anode, a hole transport layer, a light-emitting layer, a hole blocking layer,
(Continued)

← 9 Cathode
← 8 Electron injection layer
← 7 Electron transport layer
← 6 Hole blocking layer
← 5 Light-emitting layer
← 4 Hole transport layer
← 3 Hole injection layer
← 2 Transparent anode
← 1 Glass substrate an electron transport layer, and a cathode in this order, characterized in that the hole blocking layer includes a compound having a benzoazole structure represented by the following general formula (1).

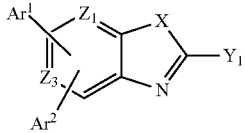

(Chem. 1)

(In the formula, $Ar^1$ and $Ar^2$ may be the same or different from each other and each represent a hydrogen atom, a deuterium atom, a substituted or unsubstituted aromatic hydrocarbon group, a substituted or unsubstituted fused polycyclic aromatic group, or a substituted or unsubstituted aromatic heterocyclic group. $Y_1$ represents a substituted or unsubstituted aromatic hydrocarbon group, a substituted or unsubstituted fused polycyclic aromatic group, a substituted or unsubstituted aromatic heterocyclic group, a straight-chained or branched alkyl group that has 1 to 6 carbon atoms and may have a substituent group, a cycloalkyl group that has 5 to 10 carbon atoms and may have a substituent group, or a straight-chained or branched alkenyl group that has 2 to 6 carbon atoms and may have a substituent group. X represents an oxygen atom or a sulfur atom. $Z_1$ and $Z_2$ may be the same or different from each other and each represent a carbon atom or a nitrogen atom).

8 Claims, 25 Drawing Sheets

(52) U.S. Cl.
CPC ...... *H01L 51/0067* (2013.01); *H01L 51/0071* (2013.01); *H01L 51/0072* (2013.01); *H01L 51/0073* (2013.01); *H01L 51/0074* (2013.01); *H01L 51/4273* (2013.01); *H01L 51/5056* (2013.01); *H01L 51/5072* (2013.01); *H01L 51/5096* (2013.01)

(58) Field of Classification Search
USPC .......................................................... 257/40
See application file for complete search history.

(56) References Cited

U.S. PATENT DOCUMENTS

| | | | |
|---|---|---|---|
| 5,792,557 A | 8/1998 | Nakaya et al. | |
| 5,834,130 A | 11/1998 | Kido | |
| 5,869,199 A | 2/1999 | Kido | |
| 2003/0165715 A1 | 9/2003 | Yoon et al. | |
| 2005/0064237 A1 | 3/2005 | Kato et al. | |
| 2007/0293704 A1 | 12/2007 | Kato et al. | |
| 2010/0060154 A1 | 3/2010 | Nomura et al. | |
| 2012/0104376 A1 | 5/2012 | Nomura et al. | |
| 2012/0228598 A1 | 9/2012 | Yokoyama et al. | |
| 2014/0374721 A1 | 12/2014 | Yokoyama et al. | |
| 2015/0236264 A1* | 8/2015 | Kim .................... | H01L 51/0061 257/40 |
| 2015/0380657 A1* | 12/2015 | Yokoyama ........... | C07D 401/14 257/40 |
| 2016/0118591 A1* | 4/2016 | Yokoyama .......... | H01L 51/0072 257/40 |
| 2016/0126464 A1* | 5/2016 | Yokoyama ............ | C07C 211/61 257/40 |
| 2017/0005273 A1* | 1/2017 | Hwang ................ | C07D 209/88 |
| 2017/0186967 A1 | 6/2017 | Hayashi et al. | |
| 2017/0358754 A1* | 12/2017 | Hayashi ................ | C07C 211/61 |
| 2019/0252621 A1 | 8/2019 | Kabasawa et al. | |

FOREIGN PATENT DOCUMENTS

| | | |
|---|---|---|
| JP | 7-126615 A | 5/1995 |
| JP | 8-48656 A | 2/1996 |
| JP | 2734341 B2 | 3/1998 |
| JP | 3194657 B2 | 7/2001 |
| JP | 2005-108804 A | 4/2005 |
| JP | 2010-83862 A | 4/2010 |
| JP | 2010-147115 A | 7/2010 |
| TW | 201100522 A1 | 1/2011 |
| WO | WO 03/060956 A2 | 7/2003 |
| WO | WO 2010/126270 A1 | 11/2010 |
| WO | WO 2011/059000 A1 | 5/2011 |
| WO | WO 2013/054764 A1 | 4/2013 |
| WO | WO 2014/009310 A1 | 1/2014 |
| WO | WO 2015/038503 A1 | 3/2015 |
| WO | WO 2015/190400 A1 | 12/2015 |
| WO | WO 2016/111269 A1 | 7/2016 |
| WO | WO 2016/153283 A1 | 9/2016 |

OTHER PUBLICATIONS

English Machine Translation of WO 2010/126270 (Year: 2010).*
Chinese Office Action and Search Report for Chinese Application No. 201880050693.1, dated Dec. 15, 2021, with English translation.
Extended European Search Report for European Application No. 18842101.0, dated Mar. 24, 2021.
Endo et al., "Efficient Up-conversion of Triplet Excitons into a Singlet State and Its Application for Organic Light Emitting Diodes," Applied Physics Letters, vol. 98, 2011 (published online Feb. 24, 2011), 3 pages.
Evindar et al., "Parallel Synthesis of a Library of Benzoxazoles and Benzothiazoles Using Ligand-Accelerated Copper-Catalyzed Cyclizations of ortho-Halobenzanilides," J. Org. Chem., vol. 71, 2006 (Published on Web, Jan. 31, 2006), pp. 1802-1808.
Hosokawa et al., "Development of Styryl-Based Light Emitting Material," The Japan Society of Applied Physics Proceedings of the Ninth Workshop, 2001, pp. 55-61. (total 8 pages), with English translation.
Kido, "White-Light-Emitting Organic EL Devices," Molecular Electronics and Bioelectronics, vol. 11, No. 1, 2000, pp. 13-19 (total 10 pages), with English translation.
Mayo et al., "Synthesis of Benzoxazoles from 2-Aminophenols and βDiketones Using a Combined Catalyst of Brønsted Acid and Copper Iodide," J. Org. Chem., vol. 79, 2014 (Published Jun. 3, 2014), pp. 6310-6314.
Wakimoto et al., "Optimization of Driving Lifetime Durability in Organic LED Devices Using Phosphorescent Guest Emitter," The Japan Society of Applied Physics Proceedings of the Ninth Workshop, 2001, pp. 23-31. (total 11 pages), with English translation.
Watanabe et al., "Organic LEDs Using Hexaphenylbenzene Derivatives," Proceedings of the 50th Meeting of the Japan Society of Applied Physics and Related Societies, 28p-A-6, 2013, 1413 (total 2 pages), with English translation.
Taiwanese Office Action and Search Report for Taiwanese Application No. 107127088, dated Nov. 10, 2021, with English translation.
Japanese Office Action for Japanese Application No. 2019-534435, dated Jun. 14, 2022, with English translation.

* cited by examiner (Compound 1)

(Compound 2)

(Compound 3)

(Compound 4)

(Compound 5)

(Compound 6)

(Compound 7)

(Compound 8)

(Compound 9)

(Compound 10)

(Compound 11)

(Compound 12)

(Compound 13)

(Compound 14)

(Compound 15)

(Compound 16)

(Compound 17)

(Compound 18)

(Compound 19)

(Compound 20)

(Compound 21)

(Compound 22)

(Compound 23)

(Compound 24)

(Compound 25)

(Compound 26)

(Compound 27)

(Compound 28)

(Compound 29)

(Compound 30)

(Compound 31) (Compound 32) (Compound 33)

(Compound 34) (Compound 35) (Compound 36)

(Compound 37) (Compound 38) (Compound 39)

(Compound 40) (Compound 41) (Compound 42)

(Compound 43) (Compound 44) (Compound 45)

FIG.3

(Compound 46) (Compound 47) (Compound 48)
(Compound 49) (Compound 50) (Compound 51)
(Compound 52) (Compound 53) (Compound 54)
(Compound 55) (Compound 56) (Compound 57)
(Compound 58) (Compound 59) (Compound 60)

FIG.4

(Compound 61)  (Compound 62)  (Compound 63)

(Compound 64)  (Compound 65)  (Compound 66)

(Compound 67)  (Compound 68)  (Compound 69)

(Compound 70)  (Compound 71)  (Compound 72)

(Compound 73)  (Compound 74)  (Compound 75)

FIG.5

(Compound 76)

(Compound 77)

(Compound 78)

(Compound 79)

(Compound 80)

(Compound 81)

(Compound 82)

(Compound 83)

(Compound 84)

(Compound 85)

(Compound 86)

(Compound 87)

(Compound 88)

(Compound 89)

(Compound 90)

(Compound 91)

(Compound 92)

(Compound 93)

(Compound 94)

(Compound 95)

(Compound 96)

(Compound 97)

(Compound 98)

(Compound 99)

(Compound 100)

(ETM-1-1)　　(ETM-1-2)　　(ETM-1-3)

(ETM-1-4)　　(ETM-1-5)　　(ETM-1-6)

(ETM-1-7)　　(ETM-1-8)　　(ETM-1-9)

(ETM-1-10)　　(ETM-1-11)　　(ETM-1-12)

(ETM-1-13)　　(ETM-1-14)　　(ETM-1-15)

(ETM-1-16) (ETM-1-17) (ETM-1-18)
(ETM-1-19) (ETM-1-20) (ETM-1-21)
(ETM-1-22) (ETM-1-23) (ETM-1-24)
(ETM-1-25) (ETM-1-26) (ETM-1-27)
(ETM-1-28) (ETM-1-29) (ETM-1-30)

FIG.9

(ETM-1-31)

(ETM-1-32)

(ETM-1-33)

(ETM-1-34)

(ETM-1-35)

(ETM-1-36)

(ETM-1-37)

(ETM-1-38)

(ETM-1-39)

(ETM-1-40)

(ETM-1-41)

(ETM-1-42)

(ETM-1-43)

(ETM-1-44)

(ETM-1-45)

(ETM-1-46)

(ETM-1-47)

(ETM-1-48)

(ETM-1-49)

(ETM-1-50)

(ETM-1-51)

(ETM-1-52)

(ETM-1-53)

(ETM-1-54)

(ETM-1-55)

(ETM-1-56)

(ETM-1-57)

(ETM-1-58)

(ETM-1-59)

(ETM-1-60)

(ETM-1-61)

(ETM-1-62)

(ETM-1-63)

(ETM-1-64)

(ETM-1-65)

(ETM-1-66)

(ETM-1-67)

(ETM-1-68)

(ETM-1-69)

(ETM-1-70)

(ETM-1-71)

(ETM-1-72)

(ETM-1-73)

(ETM-1-74)

(ETM-1-75)

(ETM-1-76)

(ETM-1-77)

(ETM-1-78)

(ETM-1-79)

(ETM-1-80)

(ETM-1-81)

(ETM-1-82)

(ETM-1-83)

(ETM-1-84)

(ETM-1-85)

(ETM-1-86)

(ETM-1-87)

(ETM-1-88)

(ETM-1-89)

(ETM-1-90)

(ETM-1-91)

(ETM-1-92)

(ETM-1-93)

(ETM-1-94)

(ETM-1-95)

(ETM-1-96)

(ETM-1-97)

(ETM-1-98)

(ETM-1-99)

(ETM-2-1)

(ETM-2-2)

(ETM-2-3)

(ETM-2-4)

(ETM-2-5)

(ETM-2-6)

(ETM-2-7)

(ETM-2-8)

(ETM-2-9)

(ETM-2-10)

(ETM-2-11)

(ETM-2-12)

(ETM-2-13)

(ETM-2-14)

(ETM-2-15)

(ETM-2-16)

(ETM-2-17)

(ETM-2-18)

(ETM-2-19)

(ETM-2-20)

(ETM-2-21)

(ETM-2-22)

(ETM-2-23)

(ETM-2-24)

(ETM-2-25)

(ETM-2-26)

(ETM-2-27)

(ETM-2-28)

(ETM-2-29)

(ETM-2-30)

(ETM-2-31) (ETM-2-32) (ETM-2-33)

(ETM-2-34) (ETM-2-35) (ETM-2-36)

(ETM-2-37) (ETM-2-38) (ETM-2-39)

(ETM-2-40) (ETM-2-41) (ETM-2-42)

(ETM-2-43) (ETM-2-44) (ETM-2-45)

(ETM-2-46)
(ETM-2-47)
(ETM-2-48)
(ETM-2-49)
(ETM-2-50)
(ETM-2-51)
(ETM-2-52)
(ETM-2-53)
(ETM-2-54)
(ETM-2-55)
(ETM-2-56)
(ETM-2-57)
(ETM-2-58)
(ETM-2-59)
(ETM-2-60)

(ETM-2-73)

(ETM-2-74)

(ETM-2-75)

(ETM-2-76)

(ETM-2-77)

(ETM-2-78)

(ETM-2-79)

(ETM-2-80)

(ETM-2-81)

(ETM-2-82)

(ETM-2-83)

(ETM-2-84)

(ETM-2-85)   (ETM-2-86)   (ETM-2-87)

(HTM-1-1)

(HTM-1-2)

(HTM-1-3)

(HTM-1-4)

(HTM-1-5)

(HTM-1-6)

(HTM-1-7)

(HTM-1-8)

(HTM-1-9)

(HTM-1-10)

(HTM-1-11)

(HTM-1-12)

(HTM-1-13)

(HTM-1-14)

(HTM-1-15)

(HTM-2-11)

(HTM-2-12)

(HTM-2-13)

(HTM-2-14)

(HTM-2-15)

(HTM-2-16)

ORGANIC ELECTROLUMINESCENCE DEVICE THAT INCLUDES COMPOUND HAVING BENZOAZOLE STRUCTURE

TECHNICAL FIELD

The present invention relates to a compound and an device suitable for an organic electroluminescence device (hereinafter, abbreviated as organic EL device) that is a self-light-emitting device suitable for various display devices, and specifically to an organic EL device that uses a compound having a benzoazole structure.

BACKGROUND ART

Since the organic EL device is a self-light-emitting device, it is brighter than the liquid crystal device and excellent in visibility, and capable of performing clear display, and thus, active research has been done thereon.

In 1987, C. W. Tang et al. (Eastman Kodak Company) have developed a stacked structural device in which various roles are assigned to the materials, and put an organic EL device using an organic material to practical use. They have stacked a phosphor capable of transporting electrons and an organic material capable of transporting holes, and injected both charges into a phosphor layer to emit light, thereby achieving high luminance of not less than 1000 cd/m$^2$ with a voltage of not more than 10 V (see, for example, Patent Literature 1 and Patent Literature 2).

Many improvements have been made for practical use of the organic EL device until now. In an electroluminescence device that subdivides the various roles in the stacked structure and includes a anode, a hole injection layer, a hole transport layer, a light-emitting layer, an electron transport layer, an electron injection layer, and a cathode in the stated order on a substrate, high efficiency and durability have been achieved (see, for example, Non-Patent Literature 1).

Further, for the purpose of further improving the light emission efficiency, attempts have been made to use a triplet exciton and utilization of a phosphorescent compound is being considered (see, for example, Non-Patent Literature 2).

Then, an device using light emission by thermally activated delayed fluorescence (TADF) has also been developed. In 2011, Adachi et al. (Kyushu University) have realized the external quantum efficiency of 5.3% by an device using a thermally activated delayed fluorescence material. (see, for example, Non-Patent Literature 3).

The light-emitting layer can also be prepared by doping a charge transport compound generally called a host material with a fluorescent compound, a phosphorescent compound, or a material emitting delayed fluorescence. As described in the above-mentioned Non-Patent Literature, selection of an organic material in the organic EL device significantly affects various properties such as efficiency and durability of the device (see, for example, Non-Patent Literature 2).

In the organic EL device, charges injected from both electrodes are recombined in the light-emitting layer to obtain light emission, and it is important how to efficiently transfer both charges of holes and electrons to the light-emitting layer.

By enhancing the electron injection property, enhancing the mobility, enhancing the hole blocking property for blocking the holes injected from the anode, improving the probability of recombination of holes and electrons, and further confining the excitons generated in the light-emitting layer, it is possible to achieve highly efficient light emission. Therefore, the role played by the electron transport material is important, and an electron transport material having a high electron injection property, a high mobility of electrons, a high hole blocking property, and a high durability to holes is desired.

Further, from the viewpoint of device lifetime, the heat resistance and amorphous property of the material are also important. In the case of a material having a low heat resistance, thermal decomposition occurs even at a low temperature due to heat generated at the time of driving the device, and the material is degraded. In the case of a material having a low amorphous property, crystallization of the thin film occurs even in a short time, and the device is degraded. Therefore, the material to be used is desired to have a high heat resistance and an excellent amorphous property.

Tris (8-hydroxyquinoline) aluminum (hereinafter, abbreviated as Alq$_3$), which is a typical light-emitting material, is generally used as an electron transport material. However, it cannot be said that the hole blocking property is enough because electron movement in the Alq$_3$ is slow and the work function of the Alq$_3$ is 5.6 eV.

As a compound having improved properties such as the electron injection property and the mobility, a compound having a benzotriazole structure has been proposed (see, for example, Patent Literature 3). However, in the device using these compounds for the electron transport layer, although the light emission efficiency has been improved, it is still not sufficient and a further lower driving voltage and further higher light emission efficiency are desired.

Further, as an electron transport material excellent in the hole blocking property, 3-(4-biphenylyl)-4-phenyl-5-(4-t-butylphenyl)-1,2,4-triazole (hereinafter, abbreviated as TAZ) has been proposed (see, for example, Patent Literature 4).

Because TAZ has a large work function of 6.6 eV and high hole blocking performance, TAZ is used as a hole blocking layer having an electrons transport property, which is stacked on the cathode side of a fluorescent light-emitting layer or a phosphorescent light-emitting layer prepared by vacuum deposition, coating, or the like, and contributes to make an organic EL device more highly efficient (see, for example, Non-Patent Literature 4).

However, a low electron transport property has been a major issue in TAZ, and it has been necessary to prepare an organic EL device by combining TAZ with an electron transport material having a higher electron transport property (see, for example, Non-Patent Literature 5).

Further, also in BCP, although the work function is high, i.e., 6.7 eV and the hole blocking performance is high, the stability of the thin film is poor because the glass transition point (Tg) is low, i.e., 83° C., and it cannot be said that BCP sufficiently functions as a hole blocking layer.

None of the materials has sufficient film stability or a sufficient function of blocking holes. In order to improve device properties of an organic EL device, an organic compound that is excellent in electron injection/transport performance and hole blocking performance and has high stability in a film state is desired.

CITATION LIST

Patent Literature

Patent Literature 1: Japanese Patent Application Laid-open No. 1996-048656
Patent Literature 2: Japanese Patent No. 3194657
Patent Literature 3: WO 2013/054764

Patent Literature 4: Japanese Patent Registration No. 2734341
Patent Literature 5: Japanese Patent Application Laid-open No. 2010-83862
Patent Literature 6: WO 2015/038503
Patent Literature 7: WO 2011/059000
Patent Literature 8: WO 2003/060956
Patent Literature 9: Japanese Patent Application Laid-open No. 1995-126615
Patent Literature 10: Japanese Patent Application Laid-open No. 1996-048656
Patent Literature 11: Japanese Patent Application Laid-open No. 2005-108804
Patent Literature 12: WO 2014/009310

Non-Patent Literature

Non-Patent Literature 1: The Japan Society of Applied Physics, proceedings of the ninth workshop, pp. 55-61 (2001)
Non-Patent Literature 2: The Japan Society of Applied Physics, proceedings of the ninth workshop, pp. 23-31 (2001)
Non-Patent Literature 3: Appl. Phys. Let., 98, 083302(2011)
Non-Patent Literature 4: Proceedings of the 50th Meeting of The Japan Society of Applied Physics and Related Societies 28p-A-6, p. 1413 (2003)
Non-Patent Literature 5: Molecular electronics and bioelectronics, Vol. 11, No. 1, pp. 13-19 (2000)
Non-Patent Literature 6: J. Org. chcm., 71, 1802(2006)
Non-Patent Literature 7: J. Org. chcm., 79, 6310(2014)

DISCLOSURE OF INVENTION

Technical Problem

In view of the circumstances as described above, it is an object of the present invention to provide an organic EL device in which, as a highly efficient and highly durable organic EL material, various materials excelling in electron injection/transport performance, hole blocking performance, hole resistance performance, exciton confinement performance, stability in a film state, and durability, are combined so that properties of each material can be effectively demonstrated, thereby achieving (1) high light emission efficiency and power efficiency, (2) low luminescence starting voltage, (3) low practical driving voltage, and (4) particularly long lifetime.

Examples of the physical properties that an organic compound to be provided by the present invention should have include (1) having a favorable electron injection property, (2) having high mobility of electrons, (3) being excellent in hole blocking performance, (4) being stable in a film state, and (5) being excellent in the heat resistance.

Solution to Problem

In view of the above, the present inventors have focused on that a benzoazole-based material has hole blocking performance, hole resistance performance, exciton confinement performance, and stability/durability in a film state, in order to achieve the above-mentioned object.

The present inventors have obtained knowledge that higher efficiency can be achieved by causing an electron transport layer to have a two-layer structure and selecting a benzoxazole ring compound having a specific structure as a material for a hole blocking layer (second electron transport layer) adjacent to a light-emitting layer to play a role to confine holes that have passed through the light-emitting layer from the hole side, a role to prevent, by high resistance, the material from being degraded, and a role to confine recombined excitons. Further, while obtaining knowledge that holes/electrons can be injected/transported into the light-emitting layer more efficiently by respectively selecting an arylamine compound having a specific structure and a benzoazole compound or pyrimidine compound having a specific structure as a hole transport layer and an electron transport layer (first electron transport layer), the present inventors have combined various materials with each other, studied combinations of the materials having a refined carrier balance, and intensively evaluated the properties of the device. As a result, the present invention has been completed.

[1] An organic EL device including at least a anode, a hole transport layer, a light-emitting layer, a hole blocking layer, an electron transport layer, and a cathode in this order, characterized in that the hole blocking layer includes a compound having a benzoazole structure represented by the following general formula (1).

(Chem. 1)

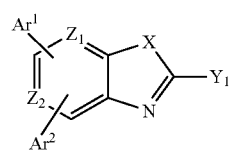

(1)

(In the formula, $Ar^1$ and $Ar^2$ may be the same or different from each other and each represent a hydrogen atom, a deuterium atom, a substituted or unsubstituted aromatic hydrocarbon group, a substituted or unsubstituted fused polycyclic aromatic group, or a substituted or unsubstituted aromatic heterocyclic group, $Y_1$ represents a substituted or unsubstituted aromatic hydrocarbon group, a substituted or unsubstituted fused polycyclic aromatic group, a substituted or unsubstituted aromatic heterocyclic group, a straight-chained or branched alkyl group that has 1 to 6 carbon atoms and may have a substituent group, a cycloalkyl group that has 5 to 10 carbon atoms and may have a substituent group, or a straight-chained or branched alkenyl group that has 2 to 6 carbon atoms and may have a substituent group, X represents an oxygen atom or a sulfur atom, and $Z_1$ and $Z_2$ may be the same or different from each other and each represent a carbon atom or a nitrogen atom).

[2] The organic EL device according to [1] above, characterized in that
the general formula (1) includes a compound having a benzoazole structure represented by the following general formula (2).

(Chem. 2)

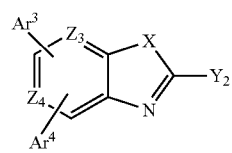

(2)

(In the formula, $Ar^3$ and $Ar^4$ may be the same or different from each other and each represent a hydrogen atom, a deuterium atom, a substituted or unsubstituted aromatic hydrocarbon group, or a substituted or unsubstituted aromatic heterocyclic group, $Y_2$ represents a substituted or unsubstituted aromatic hydrocarbon group, a substituted or unsubstituted aromatic heterocyclic group, a straight-chained or branched alkyl group that has 1 to 6 carbon atoms and may have a substituent group, a cycloalkyl group that has 5 to 10 carbon atoms and may have a substituent group, or a straight-chained or branched alkenyl group that has 2 to 6 carbon atoms and may have a substituent group, X represents an oxygen atom or a sulfur atom, and $Z_3$ and $Z_4$ may be the same or different from each other and each represent a carbon atom or a nitrogen atom. However, the aromatic heterocyclic group of each of $Ar^3$, $Ar^4$, and $Y_2$ is other than an azine ring, and the substituent group of each of $Ar^3$, $Ar^4$, and $Y_2$ is other than a fused polycyclic aromatic group and an azine ring.)

[3] The organic EL device according to [2] above, characterized in that the general formula (2) includes a compound having a benzoazole structure represented by the following general formula (3).

(Chem. 3)

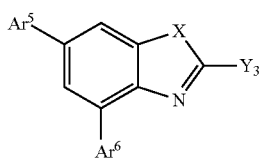

(3)

(In the formula, $Ar^5$ and $Ar^6$ may be the same or different from each other and each represent a hydrogen atom, a deuterium atom, a substituted or unsubstituted aromatic hydrocarbon group, or a substituted or unsubstituted aromatic heterocyclic group, $Y_3$ represents a substituted or unsubstituted aromatic hydrocarbon group, a substituted or unsubstituted aromatic heterocyclic group, a straight-chained or branched alkyl group that has 1 to 6 carbon atoms and may have a substituent group, a cycloalkyl group that has 5 to 10 carbon atoms and may have a substituent group, or a straight-chained or branched alkenyl group that has 2 to 6 carbon atoms and may have a substituent group, and X represents an oxygen atom or a sulfur atom. However, the aromatic heterocyclic group of each of $Ar^5$, $Ar^6$, and $Y_3$ is other than an azine ring, and the substituent group of $Ar^5$, $Ar^6$, and $Y_3$ is other than a fused polycyclic aromatic group and an azine ring.)

[4] The organic EL device according to [3] above, characterized in that the general formula (3) includes a compound having a benzoazole structure represented by the following general formula (4).

(Chem. 4)

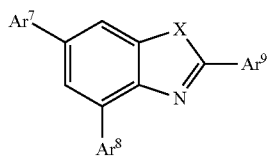

(4)

(In the formula, $Ar^7$ to $Ar^9$ may be the same or different from each other and each represent a hydrogen atom, a deuterium atom, a substituted or unsubstituted aromatic hydrocarbon group, or a substituted or unsubstituted aromatic heterocyclic group, and X represents an oxygen atom or a sulfur atom. However, the aromatic heterocyclic group of each of $Ar^7$ to $Ar^9$ is other than an azine ring, and the substituent group of each of $Ar^7$ to $Ar^9$ is other than a fused polycyclic aromatic group and an azine ring.)

[5] The organic EL device according to [4] above, characterized in that the general formula (4) includes a compound having a benzoazole structure represented by the following general formula (5).

(Chem. 5)

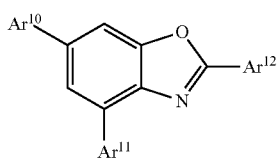

(5)

(In the formula, $Ar^{10}$ to $Ar^{12}$ may be the same or different from each other and each represent a hydrogen atom, a deuterium atom, a substituted or unsubstituted aromatic hydrocarbon group, or a substituted or unsubstituted aromatic heterocyclic group. However, the aromatic heterocyclic group of each of $Ar^{10}$ to $Ar^{12}$ is other than an azine ring, and the substituent group of $Ar^{10}$ to $Ar^{12}$ is other than a fused polycyclic aromatic group and an azine ring.)

[6] The organic EL device according to [5] above, characterized in that the general formula (5) includes a compound having a benzoazole structure represented by the following general formula (6).

(Chem. 6)

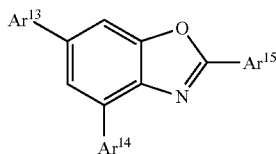

(6)

(In the formula, $Ar^{13}$ to $Ar^{15}$ may be the same or different from each other and each represent a hydrogen atom, a deuterium atom, a substituted or unsubstituted aromatic hydrocarbon group, or a substituted or unsubstituted aromatic heterocyclic group. However, the aromatic heterocyclic group of each of $Ar^{13}$ to $Ar^{15}$ is other than an azine ring, the substituent group of each of each of $Ar^{13}$ to $Ar^{15}$ is other than a fused polycyclic aromatic group and an azine ring, and at least one monovalent group represented by the following structural formula (A-1) or (A-2) is included as the aromatic heterocyclic group of each of $Ar^{13}$ to $Ar^{15}$ or the substituent group of each of $Ar^{13}$ to $Ar^{15}$)

(Chem. 7)

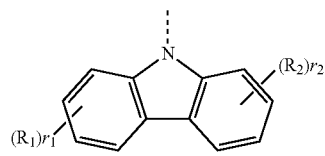
(A-1)

(Chem. 8)

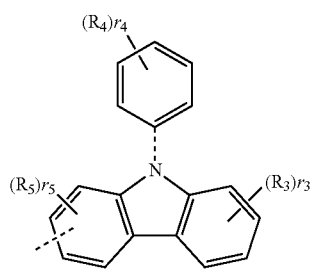
(A-2)

(In the formula, a broken line represents a binding site, each of $R_1$ to $R_5$ is a deuterium atom, a fluorine atom, a chlorine atom, a cyano group, a nitro group, a straight-chained or branched alkyl group that has 1 to 6 carbon atoms and may have a substituent group, a cycloalkyl group that has 5 to 10 carbon atoms and may have a substituent group, a straight-chained or branched alkenyl group that has 2 to 6 carbon atoms and may have a substituent group, a straight-chained or branched alkyloxy group that has 1 to 6 carbon atoms and may have a substituent group, a cycloalkyloxy group that has 5 to 10 carbon atoms and may have a substituent group, a substituted or unsubstituted aromatic hydrocarbon group, a substituted or unsubstituted aromatic heterocyclic group, or a substituted or unsubstituted aryloxy group, $r_1$ to $r_5$ may be the same or different from each other, $r_1$ to $r_3$ each represent an integer of 0 to 4, $r_4$ represents an integer of 0 to 5, and $r_5$ represents an integer of 0 to 3. In a case where any of $r_1$ to $r_5$ is an integer of two or more, a plurality of $R_1$, a plurality of $R_2$, a plurality of $R_3$, a plurality of $R_4$, or a plurality of $R_5$ bonded to the same benzene ring may be the same as or different from each other and the plurality of $R_1$, the plurality of $R_2$, the plurality of $R_3$, and the plurality of $R_5$ may be bonded to the same substituted benzene ring via a single bond, a substituted or unsubstituted methylene group, an oxygen atom, or a sulfur atom to form a ring.)

[7] The organic EL device according to any one of [1] to [6] above, characterized in that
the electron transport layer includes a compound having a benzoazole structure represented by the following general formula (ETM-1) or a compound having a pyrimidine ring structure represented by the following general formula (ETM-2).

(Chem. 9)

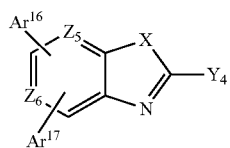
(ETM-1)

(In the formula, $Ar^{16}$ and $Ar^{17}$ may be the same or different from each other and each represent a hydrogen atom, a deuterium atom, a substituted or unsubstituted aromatic hydrocarbon group, a substituted or unsubstituted aromatic heterocyclic group, or a substituted or unsubstituted fused polycyclic aromatic group, $Y_4$ represents a substituted or unsubstituted aromatic hydrocarbon group, a substituted or unsubstituted aromatic heterocyclic group, a substituted or unsubstituted fused polycyclic aromatic group, a straight-chained or branched alkyl group that has 1 to 6 carbon atoms and may have a substituent group, a cycloalkyl group that has 5 to 10 carbon atoms and may have a substituent group, or a straight-chained or branched alkenyl group that has 2 to 6 carbon atoms and may have a substituent group, X represents an oxygen atom or a sulfur atom, and $Z_5$ and $Z_6$ may be the same or different from each other and each represent a carbon atom or a nitrogen atom.)

(Chem. 10)

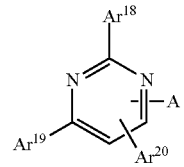
(ETM-2)

(In the formula, $Ar^{18}$ represents a substituted or unsubstituted aromatic hydrocarbon group, a substituted or unsubstituted aromatic heterocyclic group, or a substituted or unsubstituted fused polycyclic aromatic group, $Ar^{19}$ and $Ar^{20}$ each represent a hydrogen atom, a deuterium atom, a substituted or unsubstituted aromatic hydrocarbon group, a substituted or unsubstituted aromatic heterocyclic group, or a substituted or unsubstituted fused polycyclic aromatic group, both $Ar^{19}$ and $Ar^{20}$ do not represent any of a hydrogen atom and a deuterium atom, and A represents a monovalent group represented by the following structural formula (ETM-A).)

(Chem. 11)

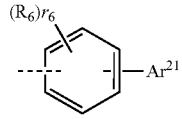
(ETM-A)

(In the formula, a broken line represents a binding site, $Ar^{21}$ represents a substituted or unsubstituted aromatic heterocyclic group, $R_6$ represents a deuterium atom, a fluorine atom, a chlorine atom, a cyano group, a trifluoromethyl group, a straight-chained or branched alkyl group that has 1 to 6 carbon atoms and may have a substituent group, a cycloalkyl group that has 5 to 10 carbon atoms and may have a substituent group, a straight-chained or branched alkenyl group that has 2 to 6 carbon atoms and may have a substituent group, a substituted or unsubstituted aromatic hydrocarbon group, a substituted or unsubstituted aromatic heterocyclic group, or a substituted or unsubstituted fused polycyclic aromatic group, and $r_6$ represents an integer of 0 to 4. In a case where $r_6$ is an integer of two or more, a plurality of $R_6$ bonded to the same benzene ring may be the same or different from each other and $R_6$ and $Ar^{21}$ may be bonded to each other via a single bond, a substituted or unsubstituted methylene group, an oxygen atom, or a sulfur atom to form a ring.)

[8] The organic EL device according to [7] above, characterized in that the hole transport layer has a two-layer structure of a first hole transport layer and a second hole transport layer, and the first hole transport layer is a triphenylamine derivative represented by the following general formula (HTM-1) or (HTM-2).

(Chem.12)

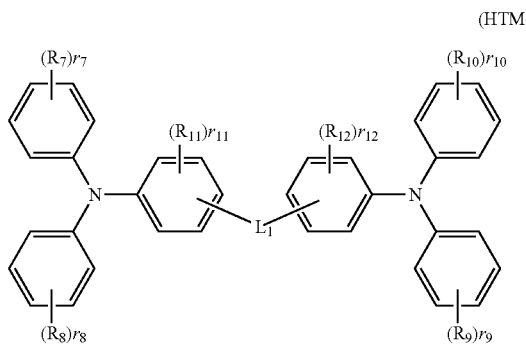

(HTM-1)

(In the formula, each of $R_7$ to $R_{12}$ represents a deuterium atom, a fluorine atom, a chlorine atom, a cyano group, a nitro group, a straight-chained or branched alkyl group that has 1 to 6 carbon atoms and may have a substituent group, a cycloalkyl group that has 5 to 10 carbon atoms and may have a substituent group, a straight-chained or branched alkenyl group that has 2 to 6 carbon atoms and may have a substituent group, a straight-chained or branched alkyloxy group that has 1 to 6 carbon atoms and may have a substituent group, a cycloalkyloxy group that has 5 to 10 carbon atoms and may have a substituent group, a substituted or unsubstituted aromatic hydrocarbon group, a substituted or unsubstituted aromatic heterocyclic group, a substituted or unsubstituted fused polycyclic aromatic group, or a substituted or unsubstituted aryloxy group. $r_7$ to $r_{12}$ may be the same or different from each other, $r_7$ to $r_{10}$ each represent an integer of 0 to 5, and $r_{10}$ and $r_{12}$ each represent an integer of 0 to 4. In a case where any of $r_7$ to $r_{12}$ is an integer of two or more, a plurality of $R_7$, a plurality of $R_8$, a plurality of $R_9$, a plurality of $R_{10}$, a plurality of $R_{11}$, or a plurality of $R_{12}$ bonded to the same benzene ring may be the same or different from each other. Further, a benzene ring and a substituent group substituted with a benzene ring, a plurality of substituent groups substituted with the same benzene ring, or benzene rings adjacent to each other via a nitrogen atom may be bonded to each other via a single bond, a substituted or unsubstituted methylene group, an oxygen atom, or a sulfur atom to form a ring. $L_1$ represents a bivalent group represented by the following structural formulae (HTM-A) to (HTM-F) or a single bond.)

(Chem. 13)

(HTM-A)

(In the formula, n represents an integer of 1 to 3.)

(Chem. 14)

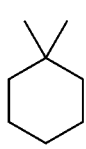

(HTM-B)

(Chem. 15)

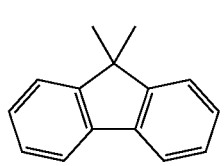

(HTM-C)

(Chem. 16)

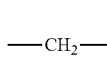

(HTM-D)

—CH$_2$—

(Chem. 17)

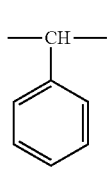

(HTM-E)

—CH—

(Chem. 18)

(HTM-F)

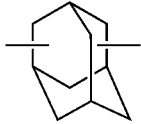

(Chem. 19)

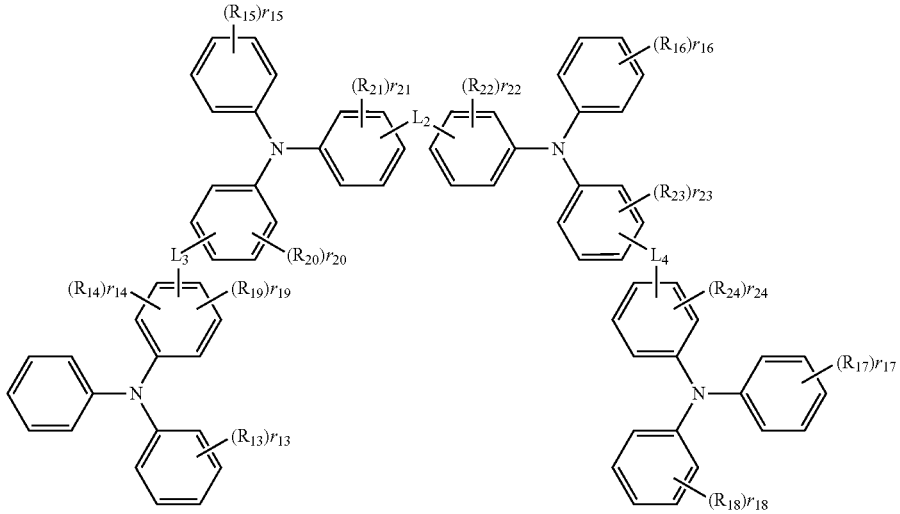

(HTM-2)

(In the formula, $R_{13}$ to $R_{24}$ each represent a deuterium atom, a fluorine atom, a chlorine atom, a cyano group, a nitro group, a straight-chained or branched alkyl group that has 1 to 6 carbon atoms and may have a substituent group, a cycloalkyl group that has 5 to 10 carbon atoms and may have a substituent group, a straight-chained or branched alkenyl group that has 2 to 6 carbon atoms and may have a substituent group, a straight-chained or branched alkyloxy group that has 1 to 6 carbon atoms and may have a substituent group, a cycloalkyloxy group that has 5 to 10 carbon atoms and may have a substituent group, a substituted or unsubstituted aromatic hydrocarbon group, a substituted or unsubstituted aromatic heterocyclic group, a substituted or unsubstituted fused polycyclic aromatic group, or a substituted or unsubstituted aryloxy group. $r_{13}$ to $r_{24}$ may be the same or different from each other, $r_{13}$ to $r_{18}$ each represent an integer of 0 to 5, and $r_{19}$ to $r_{24}$ each represent an integer of 0 to 4. In a case where any of $r_{13}$ to $r_{24}$ is an integer of two or more, a plurality of $R_{13}$, a plurality of $R_{14}$, a plurality of $R_{15}$, a plurality of $R_{16}$, a plurality of $R_{17}$, a plurality of $R_{18}$, a plurality of $R_{19}$, a plurality of $R_{20}$, a plurality of $R_{21}$, a plurality of $R_{22}$, a plurality of $R_{23}$, or a plurality of $R_{24}$ bonded to the same benzene ring may be the same or different from each other. Further, a benzene ring and a substituent group substituted with a benzene ring, a plurality of substituent groups substituted with the same benzene ring, or benzene rings adjacent to each other via a nitrogen atom may be bonded to each other via a single bond, a substituted or unsubstituted methylene group, an oxygen atom, or a sulfur atom to form a ring. $L_2$ to $L_4$ may be the same or different from each other, and each represent a bivalent group represented by the following structural formulae (HTM-A) to (HTM-F) or a single bond.)

The "aromatic hydrocarbon group", "aromatic heterocyclic group", and "fused polycyclic aromatic group" in the "substituted or unsubstituted aromatic hydrocarbon group", "substituted or unsubstituted aromatic heterocyclic group", and "substituted or unsubstituted fused polycyclic aromatic group" represented by $Ar^1$, $Ar^2$, and $Y_1$ in the general formula (1) are selected from, specifically, the group consisting of an aryl group having 6 to 30 carbon atoms and a heteroaryl group having 2 to 20 carbon atoms in addition to a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, a triphenylenyl group, a pyridyl group, a pyrimidinyl group, a triazinyl group, a furil group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a naphthyridinyl group, a phenanthrolinyl group, an acridinyl group, and a carbolinyl group.

Specific examples of the "straight-chained or branched alkyl group that has 1 to 6 carbon atoms", "cycloalkyl group that has 5 to 10 carbon atoms", and "straight-chained or branched alkenyl group that has 2 to 6 carbon atoms" in the "straight-chained or branched alkyl group that has 1 to 6 carbon atoms and may have a substituent group", "cycloalkyl group that has 5 to 10 carbon atoms and may have a substituent group", and "straight-chained or branched alkenyl group that has 2 to 6 carbon atoms and may have a substituent group" represented by $Y_1$ in the general formula (1) include a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, and a 2-buthenyl group.

Specific examples of the "substituent group" in the "substituted aromatic hydrocarbon group", "substituted aromatic heterocyclic group", "substituted fused polycyclic aromatic group", "straight-chained or branched alkyl group that has 1 to 6 carbon atoms and may have a substituent group", "cycloalkyl group that has 5 to 10 carbon atoms and may have a substituent group", and "straight-chained or branched alkenyl group that has 2 to 6 carbon atoms and may have a substituent group" represented by $Ar^1$, $Ar^2$, and $Y_1$ in the general formula (1) include an aryl group having 6 to 30 carbon atoms and a heteroaryl group having 2 to 20 carbon atoms in addition to a deuterium atom, a cyano group, a nitro group; a halogen atom such as a fluorine atom, a chlorine atom, a bromine atom, and an iodine atom; a silyl group such as a trimethylsilyl group and a triphenylsilyl group; a straight-chained or branched alkyl group that has 1 to 6 carbon atoms such as a methyl group, an ethyl group, and a propyl group; a straight-chained or branched alkyloxy group that has 1 to 6 carbon atoms such as a methyloxy group, an ethyloxy group, and a propyloxy group; an alkenyl group such as a vinyl group and an allyl group; an aryloxy group such as a phenyloxy group and a tolyloxy group; an arylalkyloxy group such as a benzyloxy group and a phenethyloxy group; an aromatic hydrocarbon group or fused polycyclic aromatic group such as a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, and a triphenylenyl group; a pyridyl group, a thienyl group, a furil group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, and a carbolinyl group, and these substituent groups may be further substituted with the exemplified substituent groups. Further, benzene rings substituted with these substituent groups or a plurality of substituent groups substituted on the same benzene ring may be bonded to each other via a single bond, a substituted or unsubstituted methylene group, an oxygen atom, or a sulfur atom to form a ring.

The "aromatic hydrocarbon group" and "aromatic heterocyclic group" in the "substituted or unsubstituted aromatic hydrocarbon group" and "substituted or unsubstituted aromatic heterocyclic group" represented by $Ar^3$ to $Ar^{15}$, $Y_2$, and $Y_3$ in the general formulae (2) to (6) are selected from, specifically, the group consisting of an aromatic hydrocarbon group having 6 to 30 carbon atoms and an aromatic heterocyclic group having 2 to 20 carbon atoms in addition to a phenyl group, a biphenylyl group, a terphenylyl group, a fluorenyl group, an indenyl group, a spirobifluorenyl group, a furil group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a naphthyridinyl group, a phenanthrolinyl group, an acridinyl group, and a carbolinyl group.

Examples of the "straight-chained or branched alkyl group that has 1 to 6 carbon atoms", "cycloalkyl group that has 5 to 10 carbon atoms", and "straight-chained or branched alkenyl group that has 2 to 6 carbon atoms" in the "straight-chained or branched alkyl group that has 1 to 6 carbon atoms and may have a substituent group", "cycloalkyl group that has 5 to 10 carbon atoms and may have a substituent group", and "straight-chained or branched alkenyl group that has 2 to 6 carbon atoms and may have a substituent group" represented by $Y_2$ and $Y_3$ in the general formulae (2) and (3) include the similar ones as described for the "straight-chained or branched alkyl group that has 1 to 6 carbon atoms", "cycloalkyl group that has 5 to 10 carbon atoms", and "straight-chained or branched alkenyl group that has 2 to 6 carbon atoms" represented by $Y_1$ in the general formula (1), and aspects similar to those of the "straight-chained or branched alkyl group that has 1 to 6 carbon atoms", "cycloalkyl group that has 5 to 10 carbon atoms", and "straight-chained or branched alkenyl group that has 2 to 6 carbon atoms" can be taken.

Specific examples of the "substituent group" in the "substituted aromatic hydrocarbon group", "substituted aromatic heterocyclic group", "straight-chained or branched alkyl group that has 1 to 6 carbon atoms and may have a substituent group", "cycloalkyl group that has 5 to 10 carbon atoms and may have a substituent group", and "straight-chained or branched alkenyl group that has 2 to 6 carbon atoms and may have a substituent group" represented by $Ar^3$ to $Ar^{15}$, $Y_2$, and $Y_3$ in the general formulae (2) to (6) include an aromatic hydrocarbon group having 6 to 30 carbon atoms and an aromatic heterocyclic group having 2 to 20 carbon atoms in addition to a deuterium atom, a cyano group, a nitro group; a halogen atom such as a fluorine atom, a chlorine atom, a bromine atom, and an iodine atom; a silyl group such as a trimethylsilyl group and a triphenylsilyl group; a straight-chained or branched alkyl group that has 1 to 6 carbon atoms such as a methyl group, an ethyl group, and a propyl group; a straight-chained or branched alkyloxy group that has 1 to 6 carbon atoms such as a methyloxy group, an ethyloxy group, and a propyloxy group; an alkenyl group such as a vinyl group and an allyl group; an aryloxy group such as a phenyloxy group and a tolyloxy group; an arylalkyloxy group such as a benzyloxy group and a phenethyloxy group; an aromatic hydrocarbon group such as a phenyl group, a biphenylyl group, a terphenylyl group, a fluorenyl group, a spirobifluorenyl group, and an indenyl group; a thienyl group, a furil group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, and a carbolinyl group, and these substituent groups may be further substituted with the exemplified substituent groups. Further, benzene rings substituted with these substituent groups or a plurality of substituent groups substituted on the same benzene ring may be bonded to each other via a single bond, a substituted or unsubstituted methylene group, an oxygen atom, or a sulfur atom to form a ring.

Examples of the "aromatic hydrocarbon group" and "aromatic heterocyclic group" in the "substituted or unsubstituted aromatic hydrocarbon group" and "substituted or unsubstituted aromatic heterocyclic group" represented by $R_1$ to $R_5$ in the structural formulae (A-1) and (A-2) in the general formula (6) include similar ones as described for the "aromatic hydrocarbon group" and "aromatic heterocyclic group" represented by the $Ar^3$ to $Ar^{15}$, $Y_2$, and $Y_3$ in the general formulae (2) to (6), and aspects similar to those of the "aromatic hydrocarbon group" and "aromatic heterocyclic group" can be taken.

Specific examples of the "straight-chained or branched alkyl group that has 1 to 6 carbon atoms", "cycloalkyl group that has 5 to 10 carbon atoms", "straight-chained or branched alkenyl group that has 2 to 6 carbon atoms", "straight-chained or branched alkyloxy group that has 1 to 6 carbon atoms", "cycloalkyloxy group that has 5 to 10 carbon atoms", and "aryloxy group" in the "straight-chained or branched alkyl group that has 1 to 6 carbon atoms and may have a substituent group", "cycloalkyl group that has 5 to 10 carbon atoms and may have a substituent group", "straight-chained or branched alkenyl group that has 2 to 6 carbon atoms and may have a substituent group", "straight-chained or branched alkyloxy group that has 1 to 6 carbon atoms and may have a substituent group", "cycloalkyloxy group that has 5 to 10 carbon atoms and may have a substituent group", and "substituted or unsubstituted aryloxy group" represented by $R_1$ to $R_5$ in the structural formulae (A-1) and (A-2) in the general formula (6) include a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, a 2-buthenyl group, a methyloxy group, an ethyloxy group, an n-propyloxy group, a cyclopentyloxy group, a cyclohexyloxy group, a 1-adamantyloxy group, a phenyloxy group, a tolyloxy group, and a biphenyloxy group.

Specific examples of the "substituent group" in the "substituted aromatic hydrocarbon group", "substituted aromatic heterocyclic group", "straight-chained or branched alkyl group that has 1 to 6 carbon atoms and may have a substituent group", "cycloalkyl group that has 5 to 10 carbon atoms and may have a substituent group", "straight-chained or branched alkenyl group that has 2 to 6 carbon atoms and may have a substituent group", "straight-chained or branched alkyloxy group that has 1 to 6 carbon atoms and may have a substituent group", "cycloalkyloxy group that has 5 to 10 carbon atoms and may have a substituent group", and "substituted aryloxy group" represented by $R_1$ to $R_5$ in the structural formulae (A-1) and (A-2) in the general formula (6) include a deuterium atom, a cyano group, a nitro group; a halogen atom such as a fluorine atom, a chlorine atom, a bromine atom, and an iodine atom; a silyl group such as a trimethylsilyl group and a triphenylsilyl group; a straight-chained or branched alkyl group that has 1 to 6 carbon atoms such as a methyl group, an ethyl group, and a propyl group; a straight-chained or branched alkyloxy group that has 1 to 6 carbon atoms such as a methyloxy group, an ethyloxy group, and a propyloxy group; an alkenyl group such as a vinyl group and an allyl group; an aryloxy group such as a phenyloxy group and a tolyloxy group; an arylalkyloxy group such as a benzyloxy group and a phenethyloxy group; an aromatic hydrocarbon group such as a phenyl group, a biphenylyl group, a terphenylyl group, a fluorenyl group, an indenyl group, and a spirobifluorenyl group; an aromatic heterocyclic group such as a thienyl group, a furil group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, and a carbolinyl group, and these substituent groups may be further substituted with the exemplified substituent groups. Further, benzene rings substituted with these substituent groups or a plurality of substituent groups substituted on the same benzene ring may be bonded to each other via a single bond, a substituted or unsubstituted methylene group, an oxygen atom, or a sulfur atom to form a ring.

Examples of the "aromatic hydrocarbon group", "aromatic heterocyclic group", and "fused polycyclic aromatic group" in the "substituted or unsubstituted aromatic hydrocarbon group", "substituted or unsubstituted aromatic heterocyclic group", and "substituted or unsubstituted fused polycyclic aromatic group" represented by $Ar^{16}$ to $Ar^{20}$, $Y_4$, and $R_6$ in the general formulae (ETM-1), (ETM-2), and (ETM-A) include similar ones as described for the "aromatic hydrocarbon group", "aromatic heterocyclic group", and "fused polycyclic aromatic group" represented by $Ar^1$, $Ar^2$, and $Y_1$ in the general formula (1), and aspects similar to those of the "aromatic hydrocarbon group", "aromatic heterocyclic group", and "fused polycyclic aromatic group" can be taken.

Examples of the "straight-chained or branched alkyl group that has 1 to 6 carbon atoms and may have a substituent group", "cycloalkyl group that has 5 to 10 carbon atoms and may have a substituent group", and "straight-chained or branched alkenyl group that has 2 to 6 carbon atoms and may have a substituent group" represented by $Y_4$ in the general formula (ETM-1) include similar ones as described for the "straight-chained or branched alkyl group that has 1 to 6 carbon atoms", "cycloalkyl group that has 5 to 10 carbon atoms", and "straight-chained or branched alkenyl group that has 2 to 6 carbon atoms" represented by $Y_1$ in the general formula (1), and aspects similar to those of the "straight-chained or branched alkyl group that has 1 to 6 carbon atoms", "cycloalkyl group that has 5 to 10 carbon atoms", and "straight-chained or branched alkenyl group that has 2 to 6 carbon atoms" can be taken.

Examples of the "substituent group" in the "substituted aromatic hydrocarbon group", "substituted aromatic heterocyclic group", "substituted fused polycyclic aromatic group", "straight-chained or branched alkyl group that has 1 to 6 carbon atoms and may have a substituent group", "cycloalkyl group that has 5 to 10 carbon atoms and may have a substituent group", and "straight-chained or branched alkenyl group that has 2 to 6 carbon atoms and may have a substituent group" represented by $Ar^{16}$ to $Ar^{120}$, $Y_4$, and $R_6$ in the general formulae (ETM-1), (ETM-2), and (ETM-A) include similar ones as described for the "substituent group" represented by $Ar^1$, $Ar^2$, and $Y_1$ in the general formula (1), and aspects similar to those of the "substituent group" can be taken.

Specific examples of the "aromatic heterocyclic group" in the "substituted or unsubstituted aromatic heterocyclic group" represented by $Ar^{21}$ in the general formula (ETM-A) include groups such as a pyridyl group, a pyrimidinyl group, a triazinyl group, a furil group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, a naphthyridinyl group, a phenanthrolinyl group, an acridinyl group, and a carbolinyl group.

Examples of the "substituent group" in the "substituted aromatic heterocyclic group" represented by $Ar^{21}$ in the general formula (ETM-A) include similar ones as described for the "substituent group" represented by $Ar^1$, $Ar^2$, and $Y_1$ in the general formula (1), and aspects similar to those of the "substituent group" can be taken.

Examples of the "aromatic hydrocarbon group", "aromatic heterocyclic group", and "fused polycyclic aromatic group" in the "substituted or unsubstituted aromatic hydrocarbon group", "substituted or unsubstituted aromatic heterocyclic group", and "substituted or unsubstituted fused polycyclic aromatic group" represented by $R_7$ to $R_{24}$ in the general formulae (HTM-1) and (HTM-2) include similar ones as described for the "aromatic hydrocarbon group", "aromatic heterocyclic group", and "fused polycyclic aromatic group" represented by $Ar^1$, $Ar^2$, and $Y_1$ in the general formula (1), and aspects similar to those of the "aromatic hydrocarbon group", "aromatic heterocyclic group", and "fused polycyclic aromatic group" can be taken.

Examples of the "straight-chained or branched alkyl group that has 1 to 6 carbon atoms", "cycloalkyl group that has 5 to 10 carbon atoms", "straight-chained or branched alkenyl group that has 2 to 6 carbon atoms", "straight-chained or branched alkyloxy group that has 1 to 6 carbon atoms", "cycloalkyloxy group that has 5 to 10 carbon atoms", and "an aryloxy group" in the "straight-chained or branched alkyl group that has 1 to 6 carbon atoms and may have a substituent group", "cycloalkyl group that has 5 to 10 carbon atoms and may have a substituent group", "straight-chained or branched alkenyl group that has 2 to 6 carbon atoms and may have a substituent group", "straight-chained or branched alkyloxy group that has 1 to 6 carbon atoms and may have a substituent group", "cycloalkyloxy group that has 5 to 10 carbon atoms and may have a substituent group", and "substituted or unsubstituted aryloxy group" represented by $R_7$ to $R_{24}$ in the general formulae (HTM-1) and (HTM-2) include similar ones as described for the "straight-chained or branched alkyl group that has 1 to 6 carbon atoms", "cycloalkyl group that has 5 to 10 carbon atoms", "straight-chained or branched alkenyl group that has 2 to 6 carbon atoms", "straight-chained or branched alkyloxy group that has 1 to 6 carbon atoms", "cycloalkyloxy group that has 5 to 10 carbon atoms", and "aryloxy group" in the "straight-chained or branched alkyl group that has 1 to 6 carbon atoms and may have a substituent group", "cycloalkyl group that has 5 to 10 carbon atoms and may have a substituent group", "straight-chained or branched alkenyl group that has 2 to 6 carbon atoms and may have a substituent group", "alkyloxy group that has 1 to 6 carbon atoms and may have a substituent group", "cycloalkyl group that has 5 to 10 carbon atoms and may have a substituent group", and "substituted or unsubstituted aryloxy group" represented by the $R_1$ to $R_5$ in the structural formulae (A-1) and (A-2) in the general formula (6), and aspects similar to those of the "straight-chained or branched alkyl group that has 1 to 6 carbon atoms", "cycloalkyl group that has 5 to 10 carbon atoms", "straight-chained or branched alkenyl group that has 2 to 6 carbon atoms", "straight-chained or branched alkyloxy group that has 1 to 6 carbon atoms", "cycloalkyloxy group that has 5 to 10 carbon atoms", and "aryloxy group" can be taken.

Examples of the "substituent group" in the "substituted aromatic hydrocarbon group", "substituted aromatic heterocyclic group", "substituted fused polycyclic aromatic group", "straight-chained or branched alkyl group that has 1 to 6 carbon atoms and may have a substituent group", "cycloalkyl group that has 5 to 10 carbon atoms and may have a substituent group", "straight-chained or branched alkenyl group that has 2 to 6 carbon atoms and may have a substituent group", "straight-chained or branched alkyloxy group that has 1 to 6 carbon atoms and may have a substituent group", "cycloalkyloxy group that has 5 to 10 carbon atoms and may have a substituent group", and "substituted aryloxy group" represented by $R_7$ to $R_{24}$ in the general formulae (HTM-1) and (HTM-2) include similar ones as described for the "substituent group" represented by $Ar^1$, $Ar^2$, and $Y_1$ in the general formula (1), and aspects similar to those of the "substituent group" can be taken.

A compound having a benzoazole structure represented by the general formula (1), which is favorably used for an organic EL device according to the present invention can be used as a material of a hole blocking layer in an organic EL device. It is a compound that has hole blocking performance, hole resistance performance, exciton confinement performance, and stability/durability in a film state, and is favorable as a material of a hole blocking layer.

Each of a compound having a benzoazole structure and a compound having a pyrimidine ring structure respectively represented by the general formulae (ETM-1) and (ETM-2), which are used for the organic EL device according to the present invention, can be used as a constituent material of an electron injection layer and an electron transport layer of the organic EL device. Each of the compound having a benzoazole structure and the compound having a pyrimidine ring structure is excellent in electron injection/transport performance, and is a favorable compound as a material of an electron transport layer.

Each of the aryldiamine compound and aryltetraamine compound respectively represented by the general formulae (HTM-1) and (HTM-2), which is used for an organic EL device according to the present invention, can be used as a constituent material of a hole injection layer or a hole transport layer in the organic EL device. Each of the aryldiamine compound and aryltetraamine compound has high mobility of holes, and is a favorable compound as a hole injection layer or a hole transport layer.

By providing a material for an organic EL device excellent in hole blocking/resistance performance and exciton confinement performance between a light-emitting layer and an electron transport layer, the organic EL device according to the present invention prevents the electron transport layer from being degraded and takes out excitons without thermally deactivating them, thereby improving light emission efficiency and also durability of the organic EL device as compared with the existing organic EL device.

Further, by combining the electron transport material (ETM-1, ETM-2) and the hole transport material (HTM-1, HTM-2), which have specific structures, with each other in consideration of carrier balance, it is possible to inject/transport holes and electrons into a light-emitting layer more efficiently. By widening the recombination area in the light-emitting layer, light emission efficiency is improved, and durability of the organic EL device can be improved. The above-mentioned general formula (1) and the general formula (ETM-1) may be the same compound.

Thus, it has become possible to realize an organic EL device that has a low driving voltage, long lifetime, and particularly high efficiency.

Advantageous Effects of Invention

In, the organic EL device according to the present invention, since a compound having a specific benzoazole structure capable of effectively demonstrating the role of hole blocking/resistance/confinement has been selected, movement of holes from a light-emitting layer to an electron transport layer is controlled, thereby realizing an organic EL device that is excellent in stability/durability of a thin film and has high efficiency, a low driving voltage, and long lifetime. Further, since the electron transport material (ETM-1, ETM-2) and the hole transport material (HTM-1, HTM-2), which have specific structures, are combined with each other, materials have been selected so that holes and electrons can be injected/transported into the light-emitting layer more efficiently and a combination having more refined carrier balance has been selected, thereby realizing an organic EL device that has a lower driving voltage, longer lifetime, and higher efficiency. According to the present invention, it is possible to improve light emission efficiency, driving voltage, and particularly durability of the existing organic EL device.

BRIEF DESCRIPTION OF DRAWINGS

FIG. 3 is a diagram showing structural formulae of compounds 31 to 45 that are benzoxazole compounds.

FIG. 4 is a diagram showing structural formulae of compounds 46 to 60 that are benzoxazole compounds.

FIG. 5 is a diagram showing structural formulae of compounds 61 to 75 that are benzoxazole compounds.

FIG. 9 is a diagram showing structural formulae (ETM-1-16) to (ETM-1-30) that are compounds each having a benzoazole structure.

FIG. 17 is a diagram showing structural formulae (ETM-2-31) to (ETM-2-45) that are compounds each having a pyrimidine ring structure.

FIG. 18 is a diagram showing structural formulae (ETM-2-46) to (ETM-2-60) that are compounds each having a pyrimidine ring structure.

MODE(S) FOR CARRYING OUT THE INVENTION

Compounds 1 to 100 are shown in FIGS. 1 to 7 as specific examples of favorable compounds among the benzoxazole compounds represented by the above-mentioned general formula (1), which are favorably used for the organic EL device according to the present invention. However, the present invention is not limited to these compounds.

Structural formulae (ETM-1-1) to (ETM-1-99) are shown in FIGS. 8 to 14 as specific examples of favorable compounds among compounds each having a benzoazole structure represented by the above-mentioned general formula (ETM-1), which are favorably used for the organic EL device according to the present invention. However, the present invention is not limited to these compounds.

Note that the above-mentioned compound having a benzoazole structure can be synthesized in accordance with a method well-known per se (see, for example, patent Literatures 5 and 6, and Non-Patent Literatures 6 and 7).

Structural formulae (ETM-2-1) to (ETM-2-87) are shown in FIGS. 15 to 21 as specific examples of favorable compounds among compounds each having a pyrimidine ring structure represented by the above-mentioned general formula (ETM-2), which are favorably used for the organic EL device according to the present invention. However, the present invention is not limited to these compounds.

Note that the above-mentioned compound having a pyrimidine ring structure can be synthesized by a method well-known per se (see, for example, patent Literatures 7 and 8).

Figure 1:
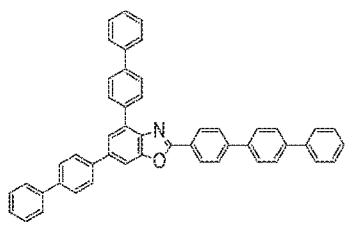
FIG. 1 is a diagram showing structural formulae of compounds 1 to 15 that are benzoxazole compounds.
Figure 1:
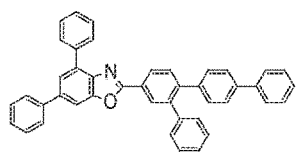
Figure 1:
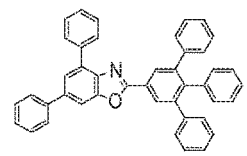
Figure 1:
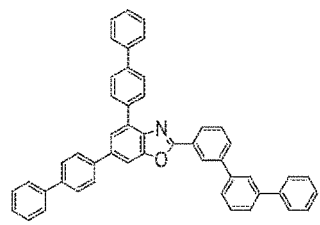
Figure 1:
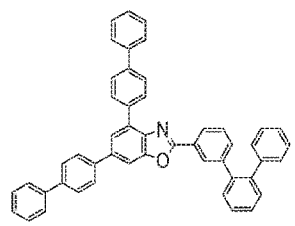
Figure 1:
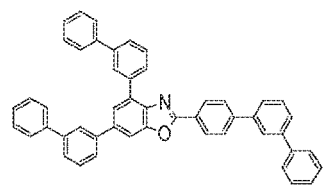
Figure 1:
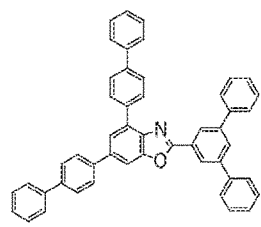
Figure 1:
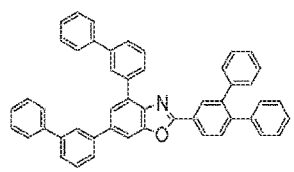
Figure 1:
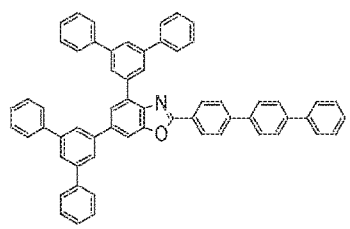
Figure 1:
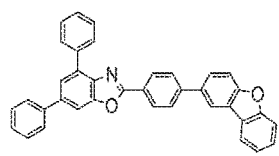
Figure 1:
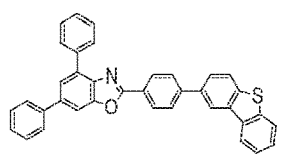
Figure 1:
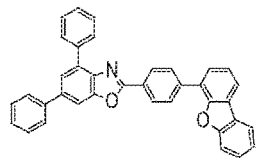
Figure 1:
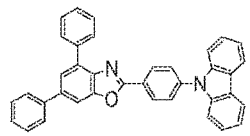
Figure 1:
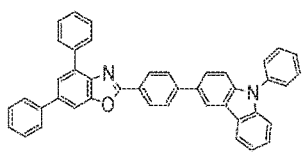
Figure 1:
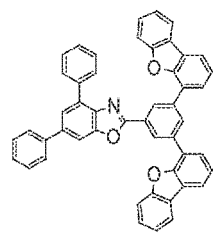
Figure 2:
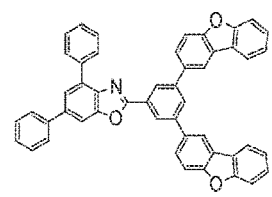
FIG. 2 is a diagram showing structural formulae of compounds 16 to 30 that are benzoxazole compounds.
Figure 2:
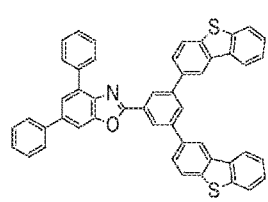
Figure 2:
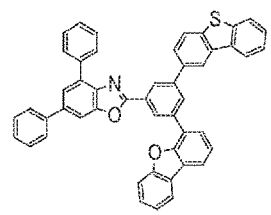
Figure 2:
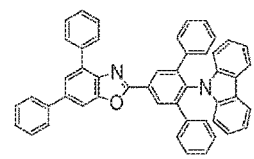
Figure 2:
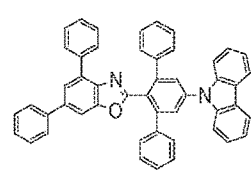
Figure 2:
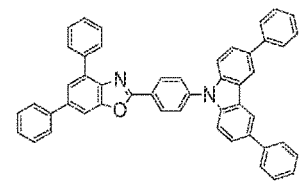
Figure 2:
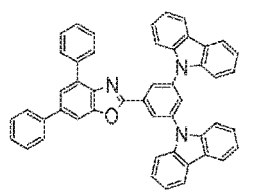
Figure 2:
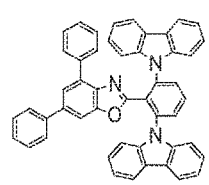
Figure 2:
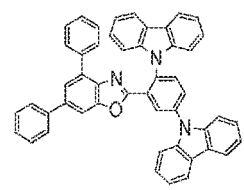
Figure 2:
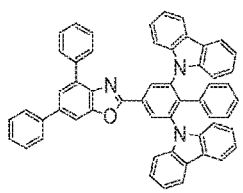
Figure 2:
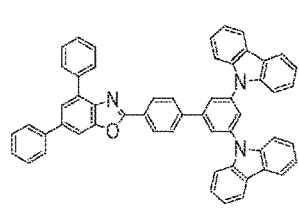
Figure 2:
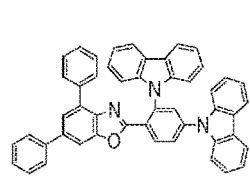
Figure 2:
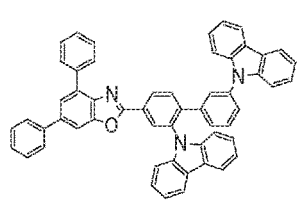
Figure 2:
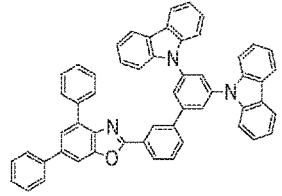
Figure 2:
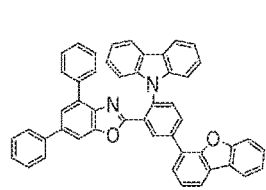
Figure 6:
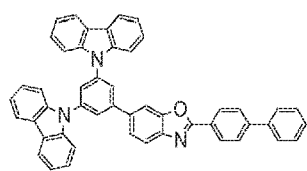
FIG. 6 is a diagram showing structural formulae of compounds 76 to 90 that are benzoxazole compounds.
Figure 6:
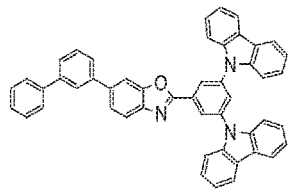
Figure 6:
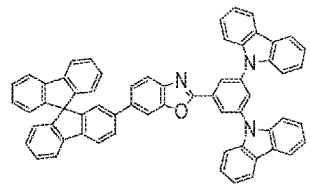
Figure 6:
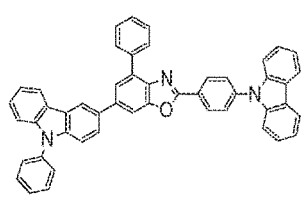
Figure 6:
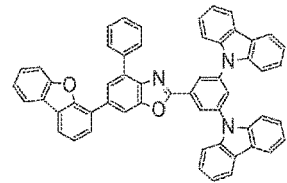
Figure 6:
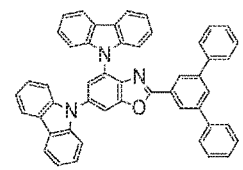
Figure 6:
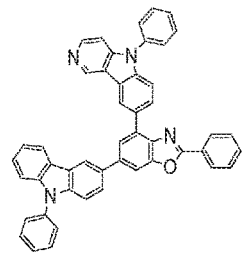
Figure 6:
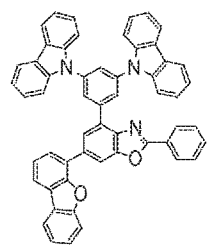
Figure 6:
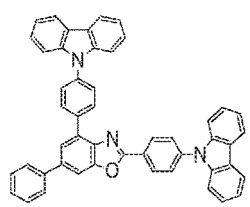
Figure 6:
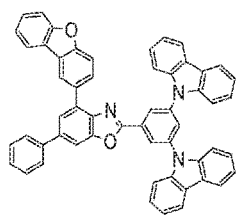
Figure 6:
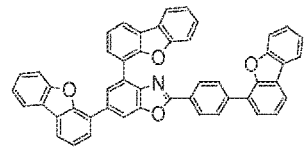
Figure 6:
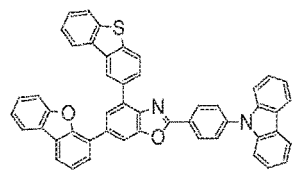
Figure 6:
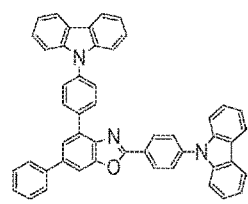
Figure 6:
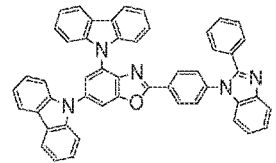
Figure 6:
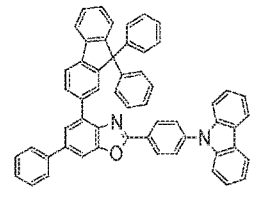
Figure 7:
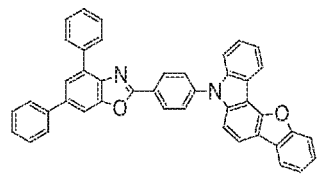
FIG. 7 is a diagram showing structural formulae of compounds 91 to 100 that are benzoxazole compounds.
Figure 7:
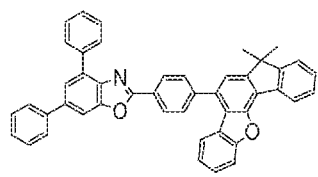
Figure 7:
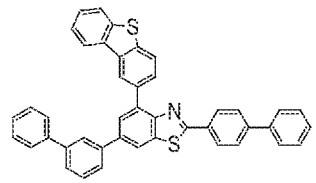
Figure 7:
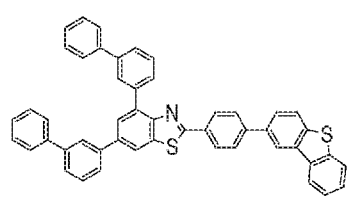
Figure 7:
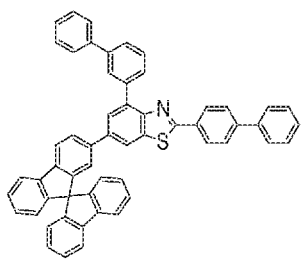
Figure 7:
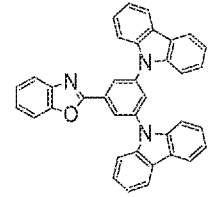
Figure 7:
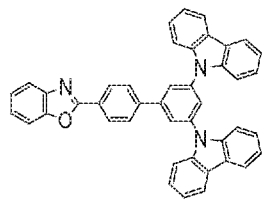
Figure 7:
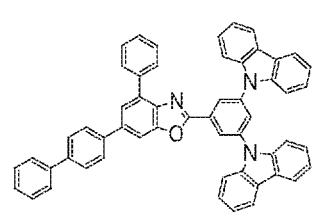
Figure 7:
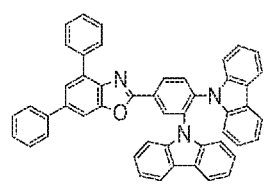
Figure 7:
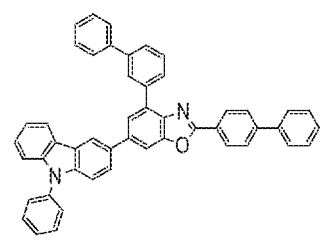
Figure 8:
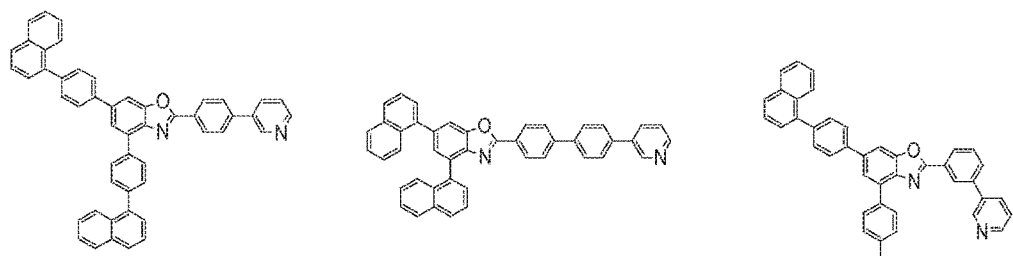
FIG. 8 is a diagram showing structural formulae (ETM-1-1) to (ETM-1-15) that are compounds each having a benzoazole structure.
Figure 8:
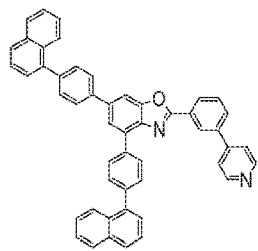
Figure 8:
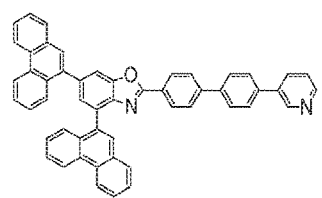
Figure 8:
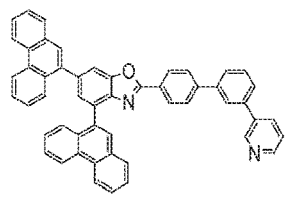
Figure 8:
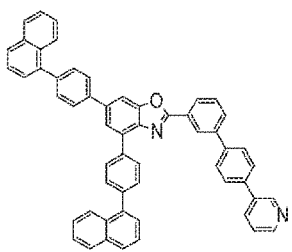
Figure 8:
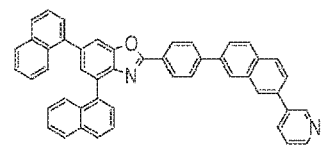
Figure 8:
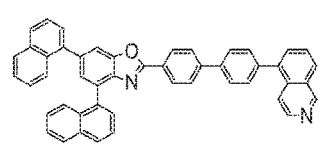
Figure 8:
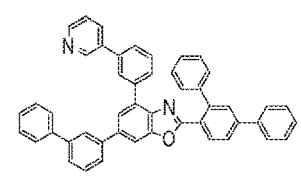
Figure 8:
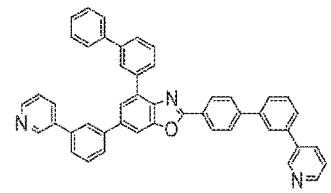
Figure 8:
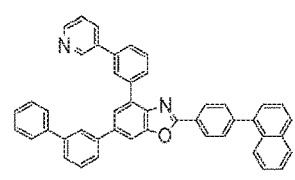
Figure 8:
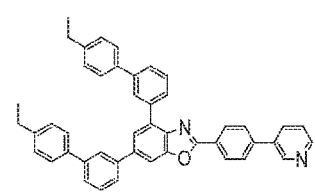
Figure 8:
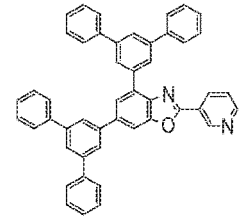
Figure 8:
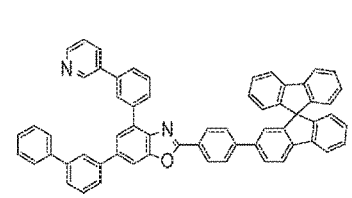
Figure 10:
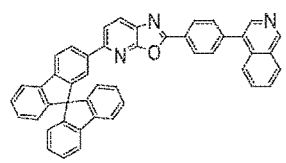
FIG. 10 is a diagram showing structural formulae (ETM-1-31) to (ETM-1-45) that are compounds each having a benzoazole structure.
Figure 10:
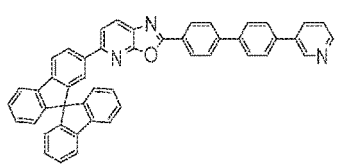
Figure 10:
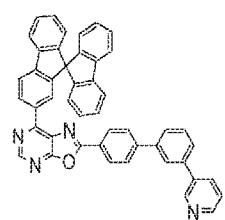
Figure 10:
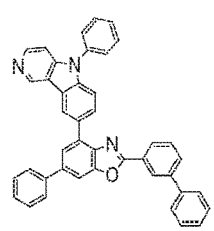
Figure 10:
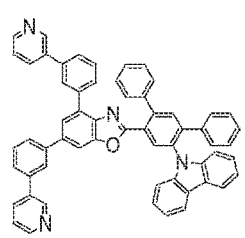
Figure 10:
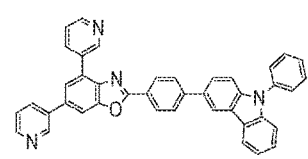
Figure 10:
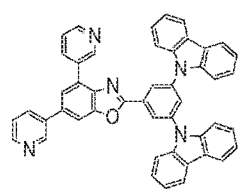
Figure 10:
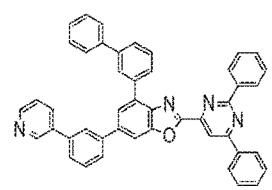
Figure 10:
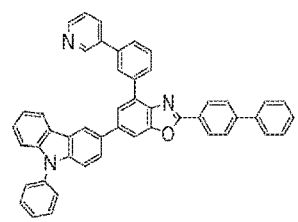
Figure 10:
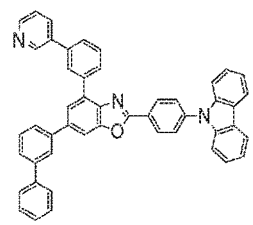
Figure 10:
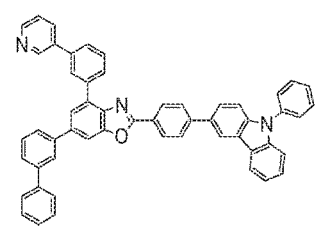
Figure 10:
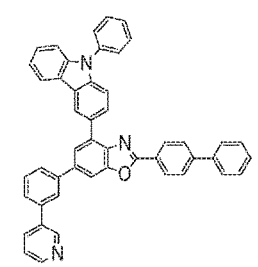
Figure 10:
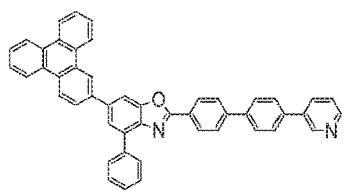
Figure 10:
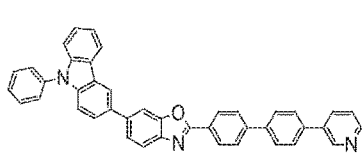
Figure 10:
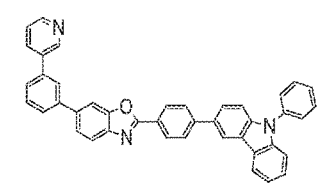
Figure 11:
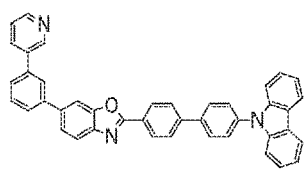
FIG. 11 is a diagram showing structural formulae (ETM-1-46) to (ETM-1-60) that are compounds each having a benzoazole structure.
Figure 11:
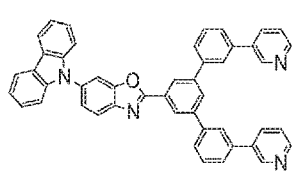
Figure 11:
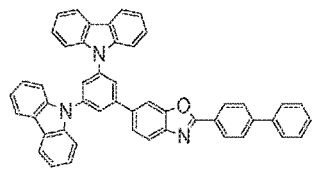
Figure 11:
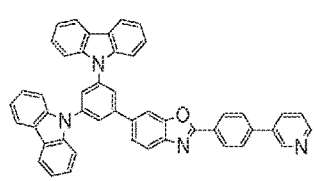
Figure 11:
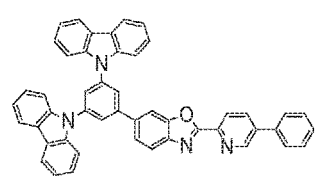
Figure 11:
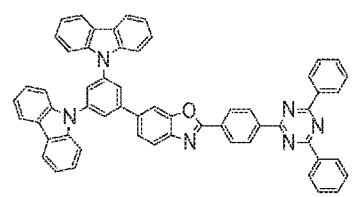
Figure 11:
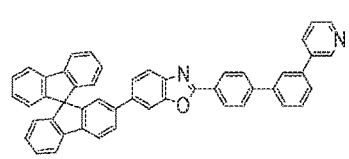
Figure 11:
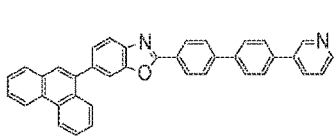
Figure 11:
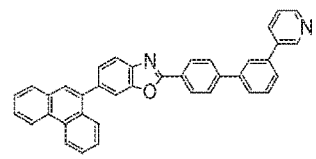
Figure 11:
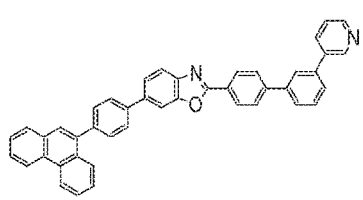
Figure 11:
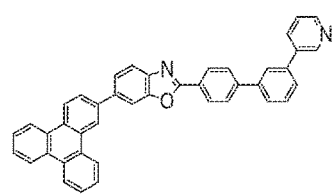
Figure 11:
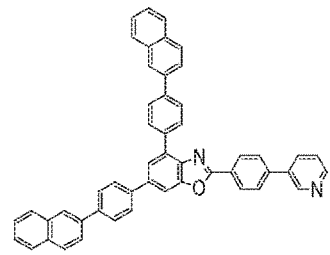
Figure 11:
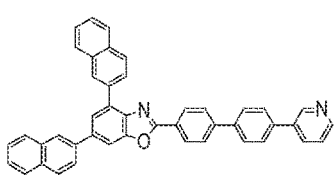
Figure 11:
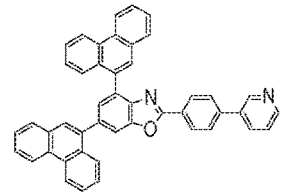
Figure 11:
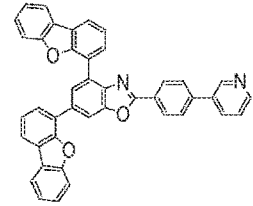
Figure 12:
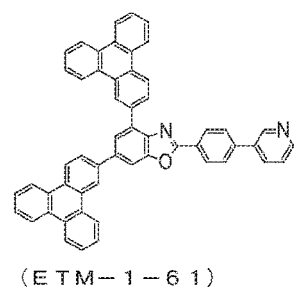
FIG. 12 is a diagram showing structural formulae (ETM-1-61) to (ETM-1-75) that are compounds each having a benzoazole structure.
Figure 12:
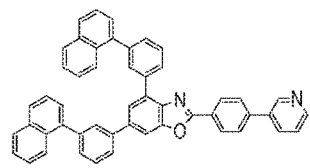
Figure 12:
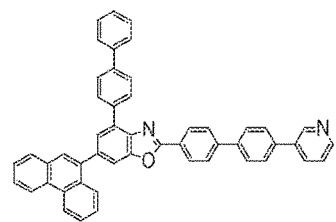
Figure 12:
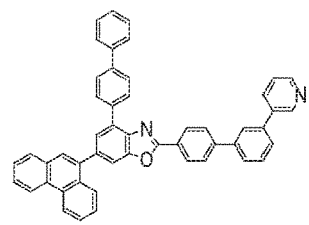
Figure 12:
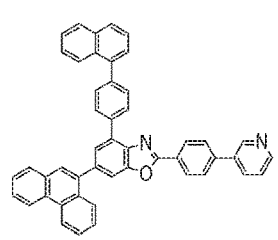
Figure 12:
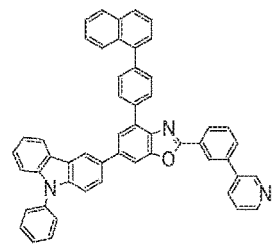
Figure 12:
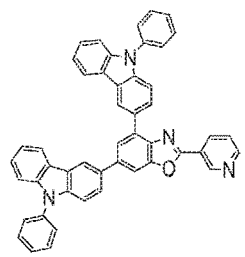
Figure 12:
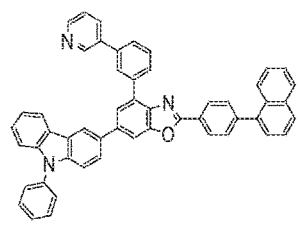
Figure 12:
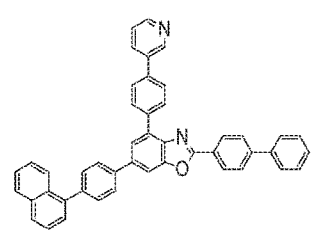
Figure 12:
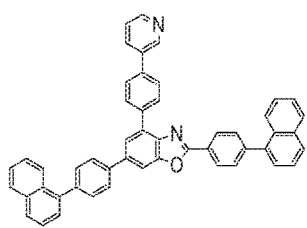
Figure 12:
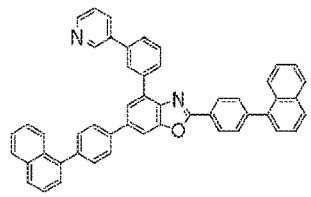
Figure 12:
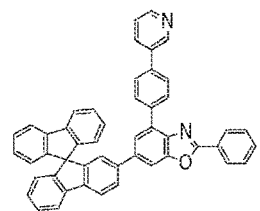
Figure 12:
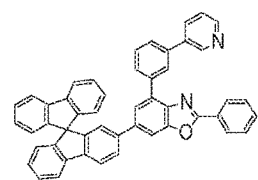
Figure 12:
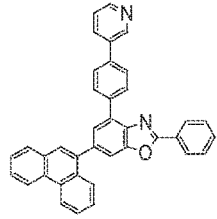
Figure 12:
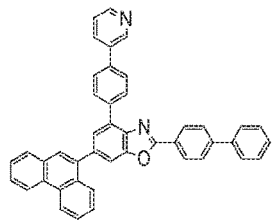
Figure 13:
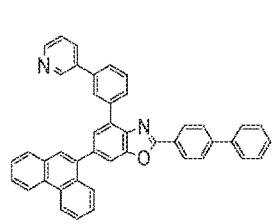
FIG. 13 is a diagram showing structural formulae (ETM-1-76) to (ETM-1-90) that are compounds each having a benzoazole structure.
Figure 13:
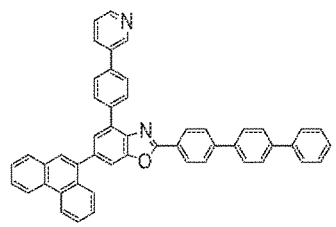
Figure 13:
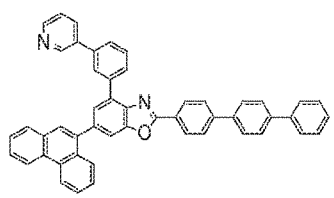
Figure 13:
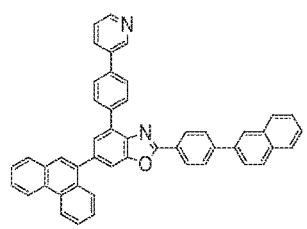
Figure 13:
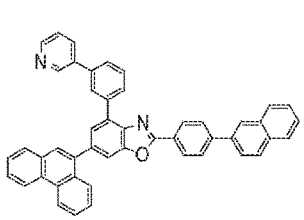
Figure 13:
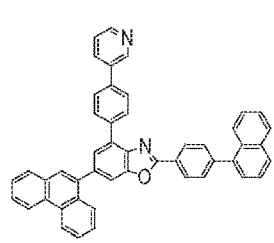
Figure 13:
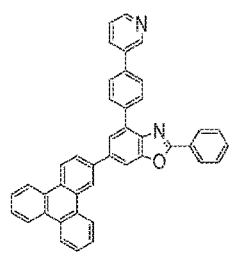
Figure 13:
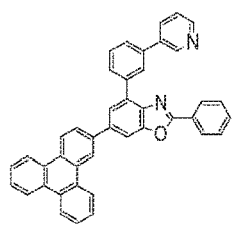
Figure 13:
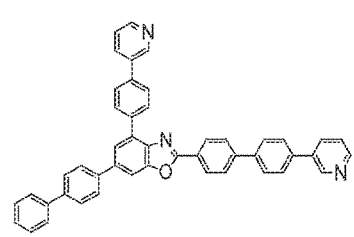
Figure 13:
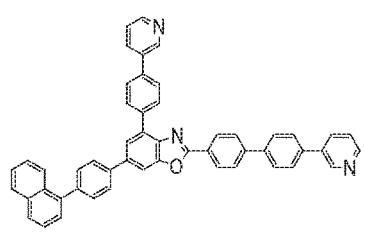
Figure 13:
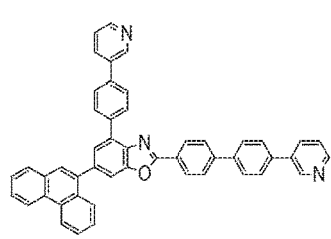
Figure 13:
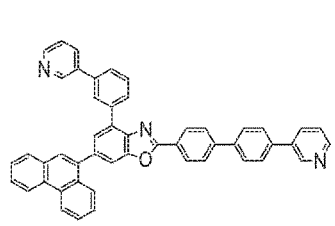
Figure 13:
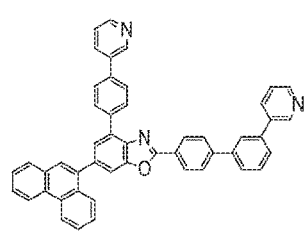
Figure 13:
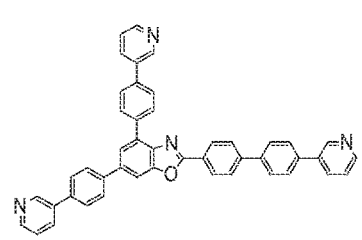
Figure 13:
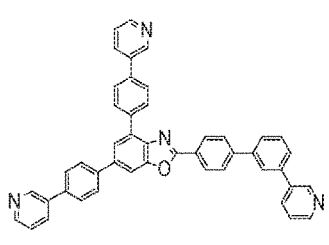
Figure 14:
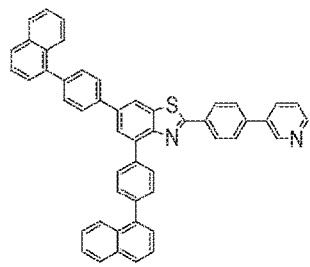
FIG. 14 is a diagram showing structural formulae (ETM-1-91) to (ETM-1-99) that are compounds each having a benzoazole structure.
Figure 14:
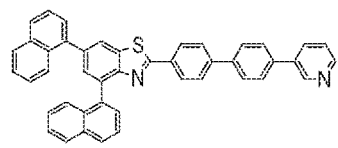
Figure 14:
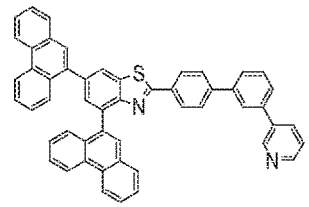
Figure 14:
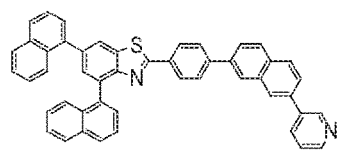
Figure 14:
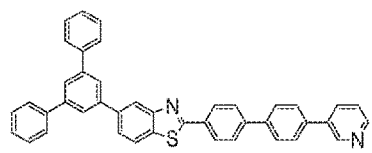
Figure 14:
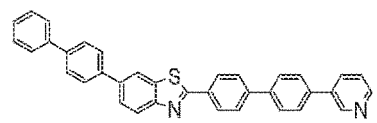
Figure 14:
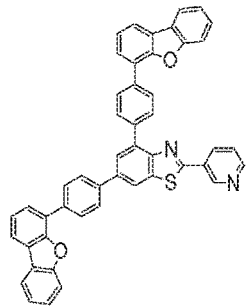
Figure 14:
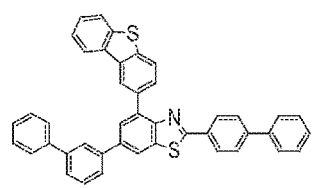
Figure 14:
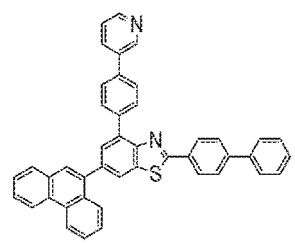
Figure 15:
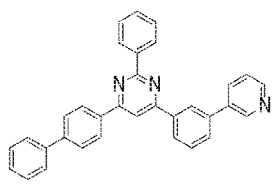
FIG. 15 is a diagram showing structural formulae (ETM-2-1) to (ETM-2-15) that are compounds each having a pyrimidine ring structure.
Figure 15:
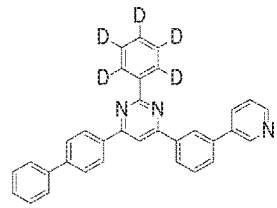
Figure 15:
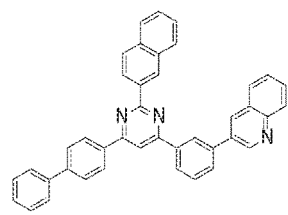
Figure 15:
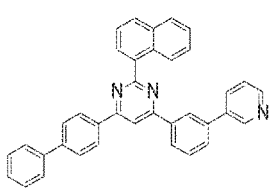
Figure 15:
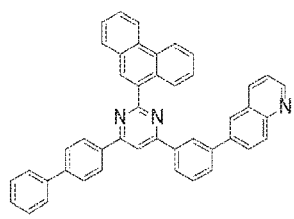
Figure 15:
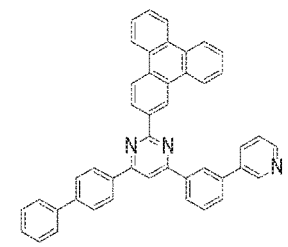
Figure 15:
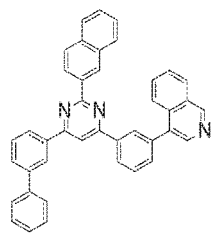
Figure 15:
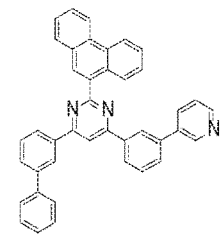
Figure 15:
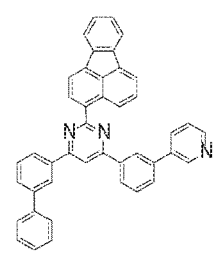
Figure 15:
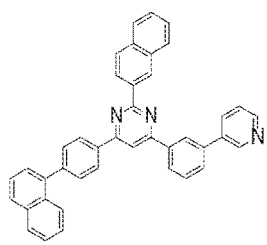
Figure 15:
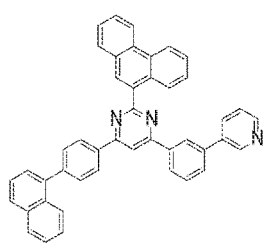
Figure 15:
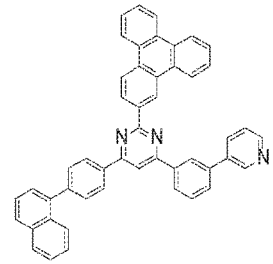
Figure 15:
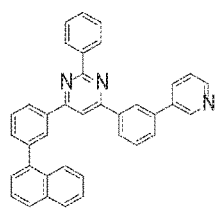
Figure 15:
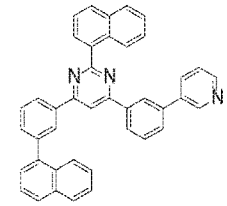
Figure 15:
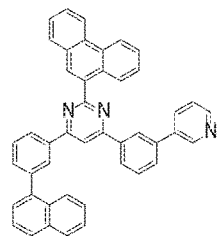
Figure 16:
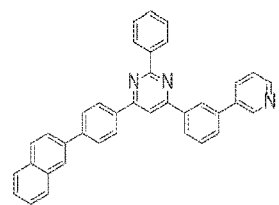
FIG. 16 is a diagram showing structural formulae (ETM-2-16) to (ETM-2-30) that are compounds each having a pyrimidine ring structure.
Figure 16:
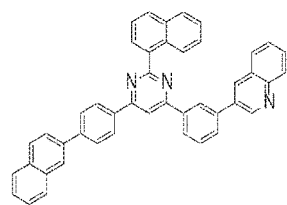
Figure 16:
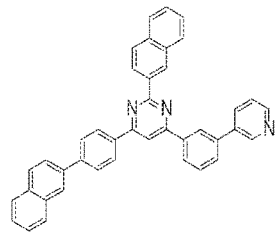
Figure 16:
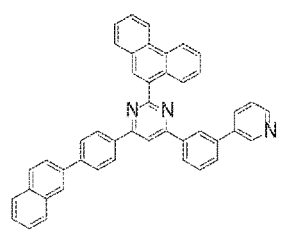
Figure 16:
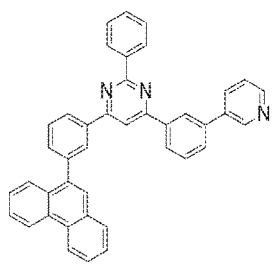
Figure 16:
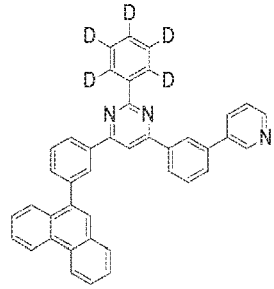
Figure 16:
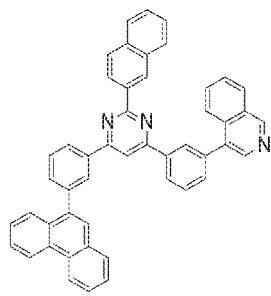
Figure 16:
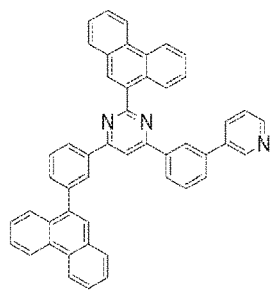
Figure 16:
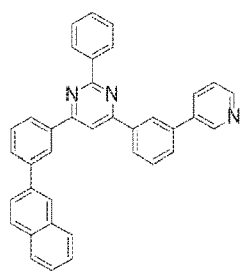
Figure 16:
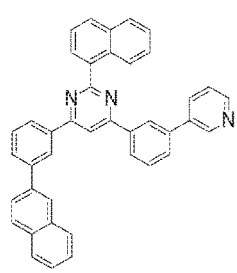
Figure 16:
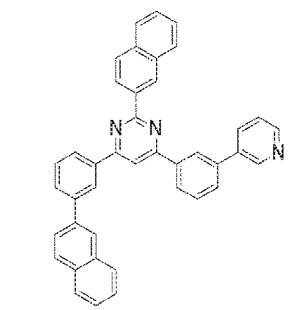
Figure 16:
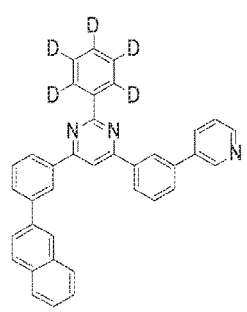
Figure 16:
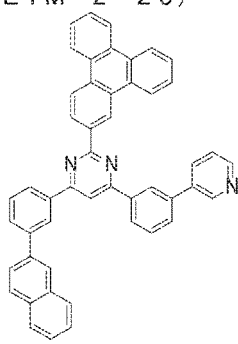
Figure 16:
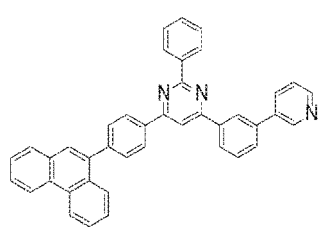
Figure 16:
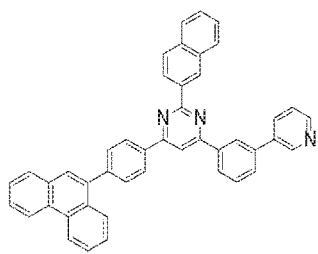
Figure 19:
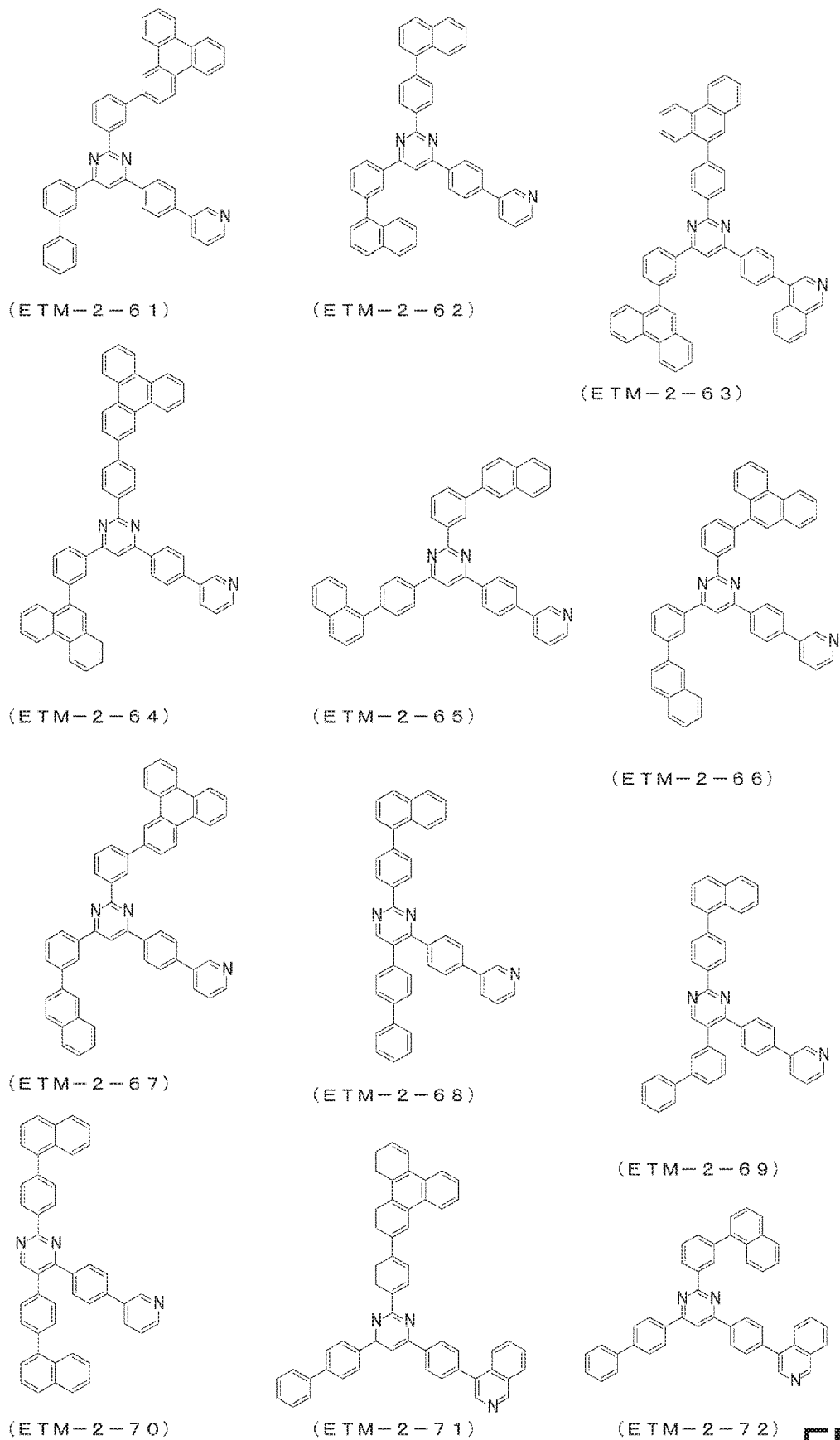
FIG. 19 is a diagram showing structural formulae (ETM-2-61) to (ETM-2-72) that are compounds each having a pyrimidine ring structure.
Figure 20:
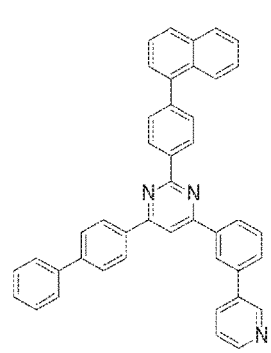
FIG. 20 is a diagram showing structural formulae (ETM-2-73) to (ETM-2-84) that are compounds each having a pyrimidine ring structure.
Figure 20:
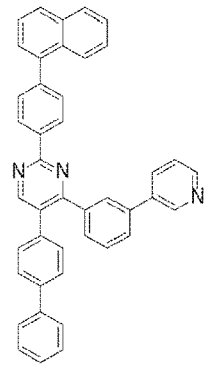
Figure 20:
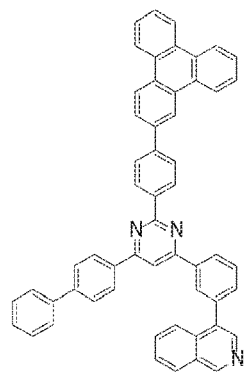
Figure 20:
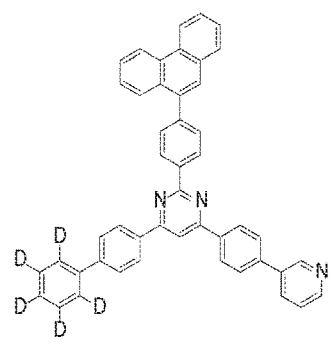
Figure 20:
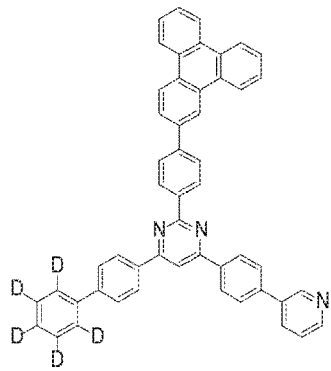
Figure 20:
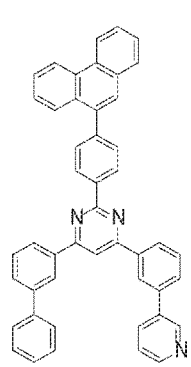
Figure 20:
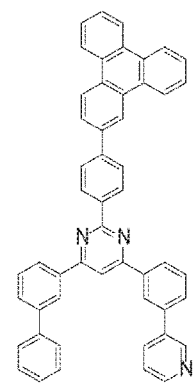
Figure 20:
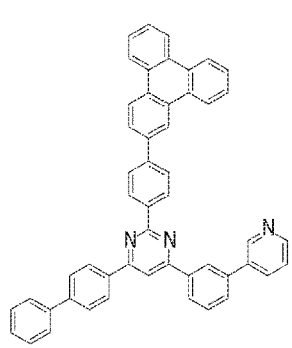
Figure 20:
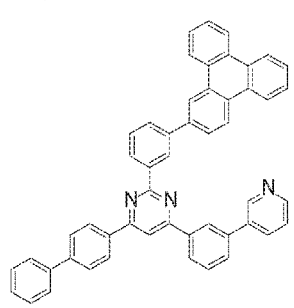
Figure 20:
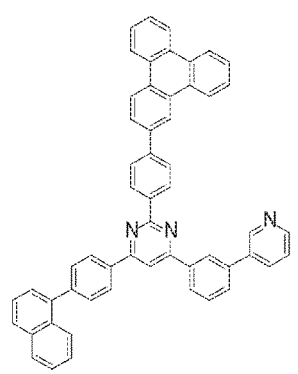
Figure 20:
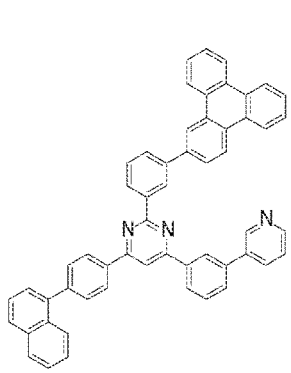
Figure 20:
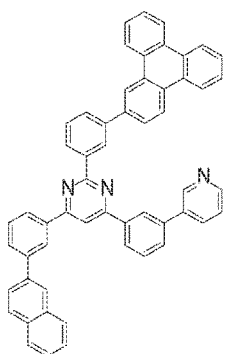
Figure 21:
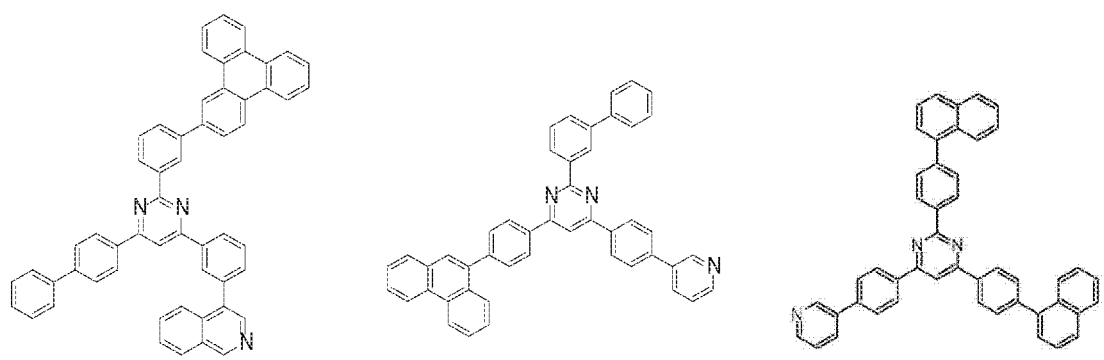
FIG. 21 is a diagram showing structural formulae (ETM-2-85) to (ETM-2-87) that are compounds each having a pyrimidine ring structure.
Figure 22:
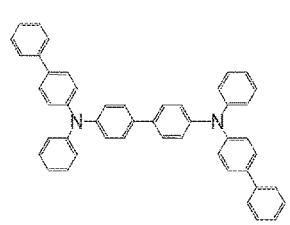
FIG. 22 is a diagram showing structural formulae (HTM-1-1) to (HTM-1-15) that are triphenylamine derivatives.
Figure 22:
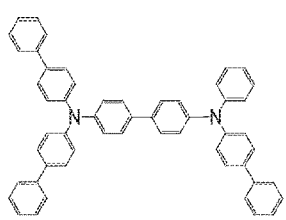
Figure 22:
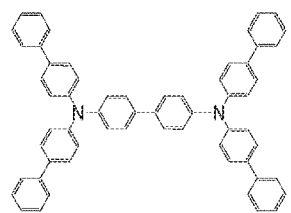
Figure 22:
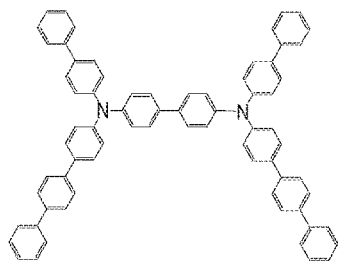
Figure 22:
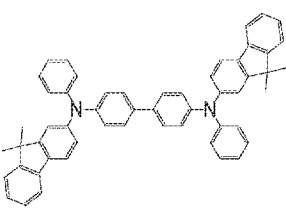
Figure 22:
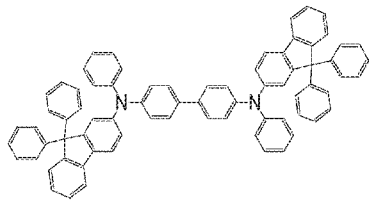
Figure 22:
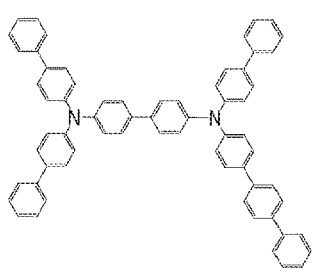
Figure 22:
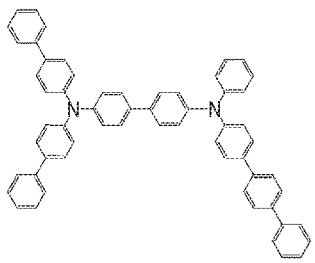
Figure 22:
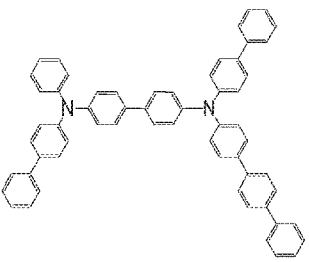
Figure 22:
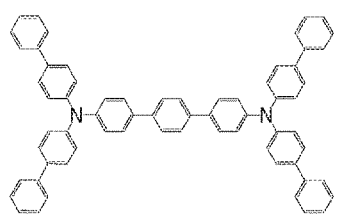
Figure 22:
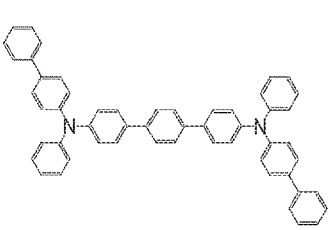
Figure 22:
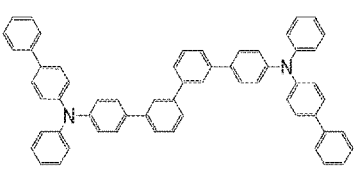
Figure 22:
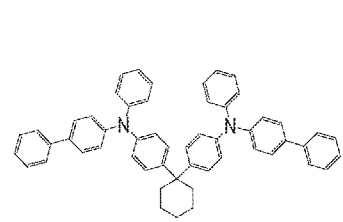
Figure 22:
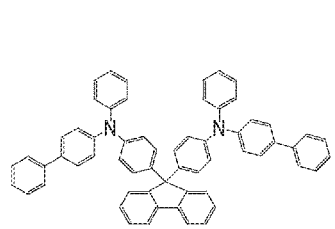
Figure 22:
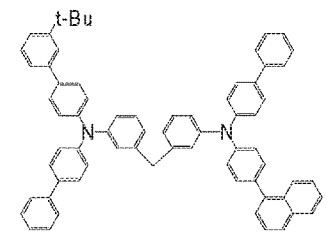
Figure 23:
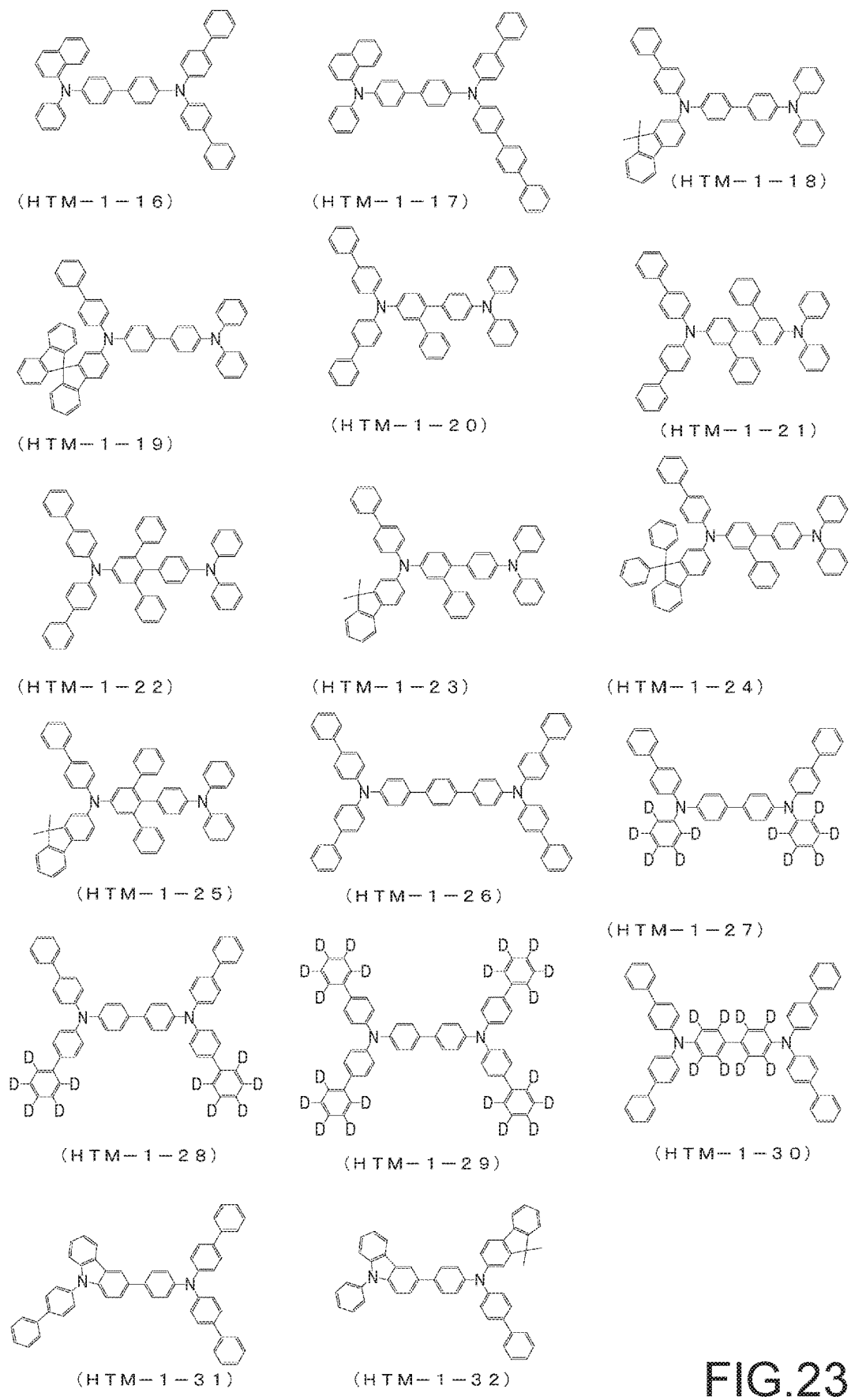
FIG. 23 is a diagram showing structural formulae (HTM-1-16) to (HTM-1-32) that are triphenylamine derivatives.

Structural formulae (HTM-1-1) to (HTM-1-32) are shown in FIGS. 22 and 23 as specific examples of favorable compounds among triphenylamine derivatives represented by the above-mentioned general formula (HTM-1), which are favorably used for the organic EL device according to the present invention. However, the present invention is not limited to these compounds.

Figure 24:
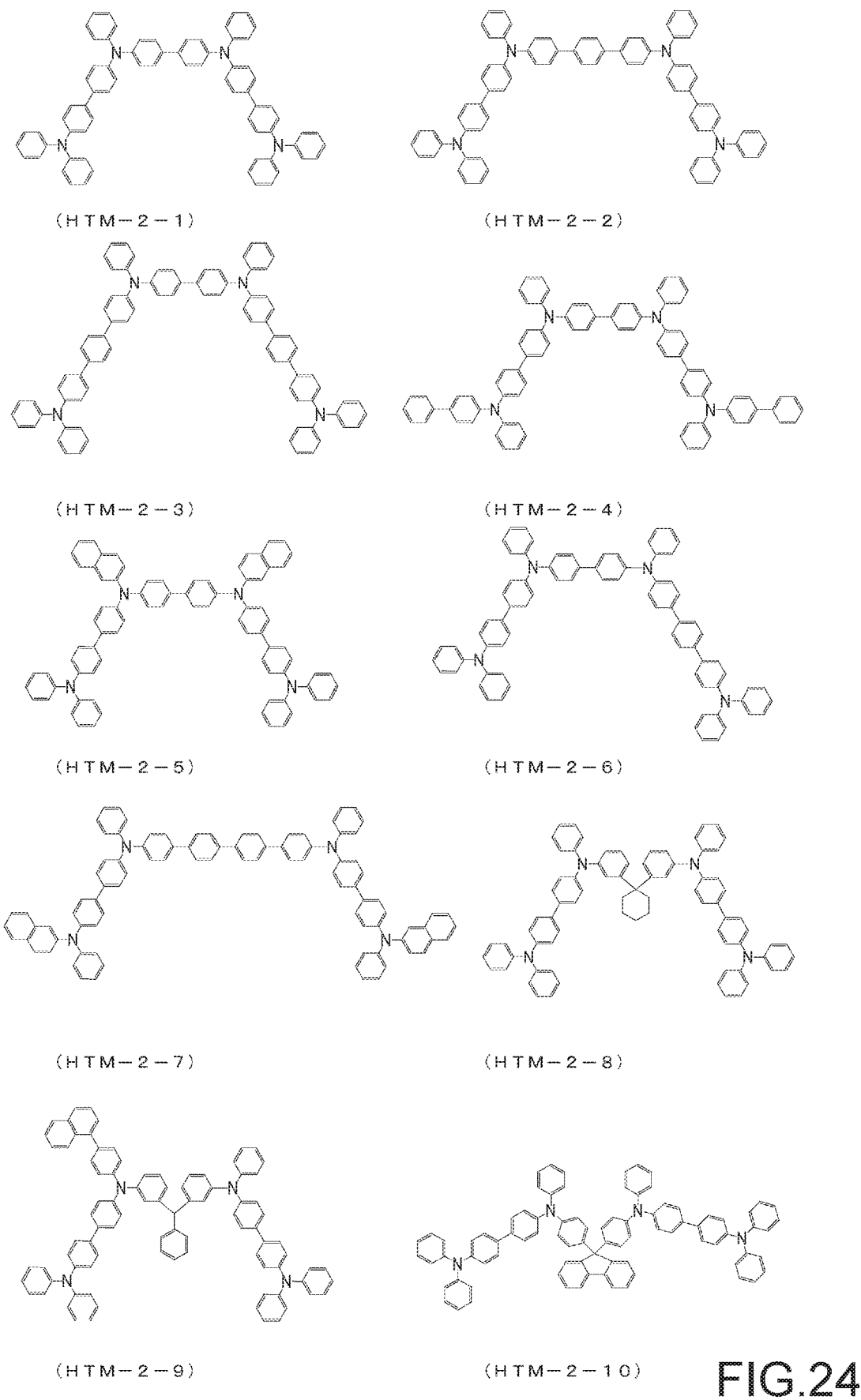
FIG. 24 is a diagram showing structural formulae (HTM-2-1) to (HTM-2-10) that are triphenylamine derivatives.
Figure 25:
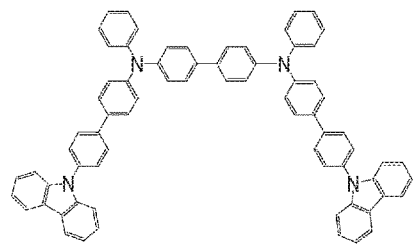
FIG. 25 is a diagram showing structural formulae (HTM-2-11) to (HTM-2-16) that are triphenylamine derivatives.
Figure 25:
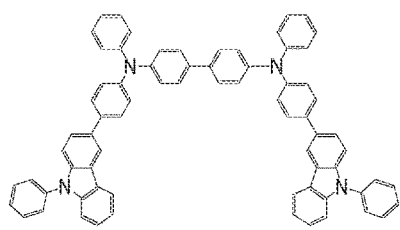
Figure 25:
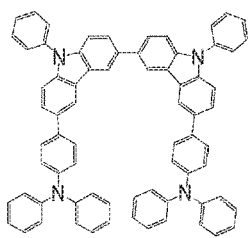
Figure 25:
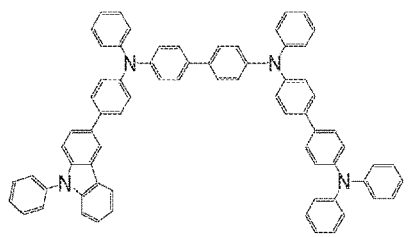
Figure 25:
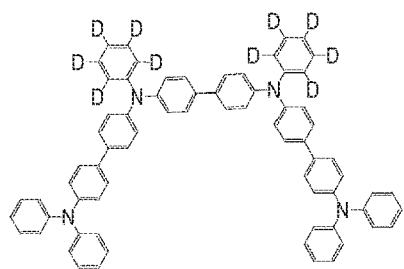
Figure 25:
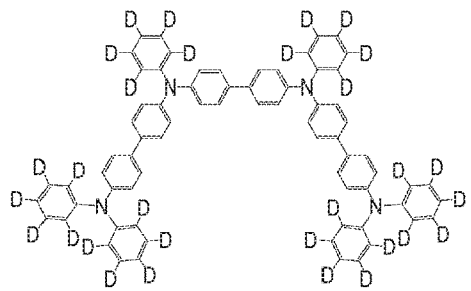

Structural formulae (HTM-2-1) to (HTM-2-16) are shown in FIGS. 24 and 25 as specific examples of favorable compounds among triphenylamine derivatives represented by the above-mentioned general formula (HTM-2), which are favorably used for the organic EL device according to the present invention. However, the present invention is not limited to these compounds.

Note that the above-mentioned compound having a triarylamine structure can be synthesized in accordance with a method well-known per se (see, for example, Patent Literatures 9 to 11).

Purification of compounds represented by the general formulae (1) to (6), (ETM-1), (ETM-2), (HTM-1), and (HTM-2) was carried out by purification by column chromatography, adsorption purification with silica gel, activated carbon, activated clay, or the like, recrystallization with a solvent, a crystallization method, a sublimation purification method, or the like. Identification of the compounds was performed by NMR analysis. As physical property values, a melting point, a glass transition point (Tg), and a work function were measured. The melting point is an index of vapor deposition property. The glass transition point (Tg) is an index of stability in a thin film state. The work function is an index of a hole transport property and a hole blocking property.

The melting point and the glass transition point (Tg) were measured with a powder using a high sensitivity differential scanning calorimeter (DSC3100SA manufactured by Bruker AXS GmbH).

The work function was obtained by preparing a thin film of 100 nm on an ITO substrate and using an ionization potential measuring apparatus (PYS-202 manufactured by Sumitomo Heavy Industries, Ltd.).

Examples of the structure of the organic EL device according to the present invention include those including an anode, a hole injection layer, a hole transport layer, a light-emitting layer, an electron transport layer, an electron injection layer, and a cathode in the stated order on a substrate, those including an electron blocking layer between the hole transport layer and the light-emitting layer, and those including a hole blocking layer between the light-emitting layer and the electron transport layer. In the multilayer structures, several organic layers can be omitted or combined. For example, the hole injection layer and the hole transport layer may be combined or the electron injection layer and the electron transport layer may be combined. Further, two or more organic layers having the same function can be stacked. For example, two hole transport layers may be stacked, two light-emitting layers may be stacked, or two electron transport layers may be stacked.

As the anode of the organic EL device according to the present invention, an electrode material having a large work function such as ITO and gold is used. As the hole injection layer of the organic EL device according to the present invention, a porphyrin compound typified by copper phthalocyanine, a starburst type triphenylamine derivative, an acceptor heterocyclic compound such as hexacyanoazatriphenylene, a coating type polymer material, or the like in addition to the arylamine compounds represented by the above-mentioned general formulae (HTM-1) and (HTM-2) can be used. These materials can be formed into a thin film by a known method such as a spin coat method and an ink jet method in addition to a vapor deposition method.

As the hole transport layer of the organic EL device according to the present invention, the arylamine compounds represented by the above-mentioned general formulae (HTM-1) and (HTM-2) are more favorable, but also a benzidine derivative such as N,N'-diphenyl-N,N'-di(m-tolyl)-benzidine (hereinafter, referred to as TPD), N,N'-diphenyl-N,N'-di(α-naphthyl)-benzidine (hereinafter, referred to as NPD), and N,N,N',N'-tetrabiphenylylbenzidine, 1,1-bis[(di-4-tolylamino)phenyl]cyclohexane (hereinafter, referred to as TAPC), or the like can be used. These materials may be deposited alone. However, any of the materials may be mixed with another material and used as a single deposited layer. Further, a stacked structure may be achieved by depositing layers of the plurality of materials alone, or mixing the plurality of materials and depositing layers thereof. Alternatively, a stacked structure of at least one layer of any of the plurality of materials deposited alone and at least one layer obtained by mixing the plurality of materials and depositing at least one layer thereof may be achieved. Further, as a hole injection/transport layer, a coating polymer material such as poly(3,4-ethylenedioxythiophene) (hereinafter, referred to as PEDOT)/poly(styrene sulfonate) (hereinafter, referred to as PSS) can be used. These materials can be formed into a thin film by a known method such as a spin coat method and an ink jet method in addition to a vapor deposition method.

Further, for the hole injection layer or hole transport layer, those obtained by P-doping the material typically used for the layer with trisbromophenylamine hexachloroantimony or a radialene derivative (see, for example, Patent Literature 12), a polymer compound having, as a partial structure, the structure of a benzidine derivative such as TPD, or the like can be used.

For the electron blocking layer of the organic EL device according to the present invention, a compound having an electron blocking property, such as a carbazol derivative such as 4,4',4''-tri(N-carbazolyl) triphenylamine (hereinafter, referred to as TCTA), 9,9-bis[4-(carbazol-9-yl)phenyl]fluorene, 1,3-bis(carbazol-9-yl)benzene (hereinafter, referred to as mCP), and 2,2-bis(4-carbazol-9-ylphenyl)adamantane (hereinafter, referred to as Ad-Cz), and a compound having a triphenylsilyl group and a triarylamine structure typified by 9-[4-(carbazol-9-yl)phenyl]-9-[4-(triphenylsilyl)phenyl]-9H-fluorene in addition to the arylamine compounds represented by the above-mentioned general formulae (HTM-1) and (HTM-2) can be used. These materials may be deposited alone. However, any of the materials may be mixed with another material and used as a single deposited layer. Further, a stacked structure may be achieved by depositing layers of the plurality of materials alone, or mixing the plurality of materials and depositing layers thereof. Alternatively, a stacked structure of at least one layer of any of the plurality of materials deposited alone and at least one layer obtained by mixing the plurality of materials and depositing at least one layer thereof may be achieved. These materials can be formed into a thin film by a known method such as a spin coat method and an ink jet method in addition to a vapor deposition method.

For the light-emitting layer of the organic EL device according to the present invention, various metal complexes, an anthracene derivative a bis-styryl benzene derivative, a pyrene derivative, an oxazole derivative, a poly(p-phenylene vinylene) derivative, or the like in addition to a metal complex of a quinolinol derivative including $Alq_3$ can be used. Further, the light-emitting layer may be formed of a host material and a dopant material. As the host material, an anthracene derivative is favorably used. In addition, not only the above-mentioned light-emitting material but also a heterocyclic compound having an indole ring as a partial structure of the fused ring, a heterocyclic compound having a carbazol ring as a partial structure of the fused ring, a carbazol derivative, a thiazole derivative, a benzimidazole derivative, a polydialkylfluorene derivative, or the like can be used. Further, as the dopant material, quinacridone, coumarin, rubrene, perylene, and derivatives thereof, a benzopyran derivative, a rhodamine derivative, an aminostyryl derivative, or the like can be used. These materials may be deposited alone. However, any of the materials may be mixed with another material and used as a single deposited layer. Further, a stacked structure may be achieved by depositing layers of the plurality of materials alone, or mixing the plurality of materials and depositing layers thereof. Alternatively, a stacked structure of at least one layer of any of the plurality of materials deposited alone and at least one layer obtained by mixing the plurality of materials and depositing at least one layer thereof may be achieved.

Further, as the light-emitting material, a phosphorescent material can be used. As the phosphorescent material, a phosphorescent material of a metal complex such as iridium and platinum can be used. A green phosphorescent material such as Ir(ppy)$_3$, a blue phosphorescent material such as FIrpic and FIr$_6$, a red phosphorescent material such as Btp$_2$Ir (acac), or the like is used. As the host material (having a hole injection/transporting property) at this time, 4,4'-di(N-carbazolyl) biphenyl (hereinafter, referred to as CEP) and a carbazol derivative such as TCTA and mCP can be used. As a host material having an electron transportability, p-bis (triphenylsilyl)benzene (hereinafter, referred to as UGH$_2$), 2,2',2''-(1,3,5-phenylene)-tris(1-phenyl-1H-benzimidazole) (hereinafter, referred to as, TPBI), or the like can be used, and an organic EL device having high performance can be prepared.

In order to avoid concentration quenching, it is favorable to dope the host material with the phosphorescent material by co-deposition in the range of 1 to 30 weight percent with respect to the entire light-emitting layer.

Further, as the light-emitting material, a material emitting delayed fluorescence such as a CDCB derivative including PIC-TRZ, CC2TA, PXZ-TRZ, and 4CzIPN can be used (see, for example, Non-Patent Literature 3). These materials can be formed into a thin film by a known method such as a spin coat method and an ink jet method in addition to a vapor deposition method.

For the hole blocking layer of the organic EL device according to the present invention, the benzoazole compounds represented by the above-mentioned general formula (1) to (6) can be used. These compounds may double as the material of the electron transport layer. These materials may be deposited alone. However, any of the materials may be mixed with another material and used as a single deposited layer. Further, a stacked structure may be achieved by depositing layers of the plurality of materials alone, or mixing the plurality of materials and depositing layers thereof. Alternatively, a stacked structure of at least one layer of any of the plurality of materials deposited alone and at least one layer obtained by mixing the plurality of materials and depositing at least one layer thereof may be achieved. These materials can be formed into a thin film by a known method such as a spin coat method and an ink jet method in addition to a vapor deposition method.

As the electron transport layer of the organic EL device according to the present invention, the benzoazole compound and the pyrimidine compound respectively represented by the above-mentioned general formulae (ETM-1) and (ETM-2) are more favorable, but also various metal complexes, a triazole derivative, triazine derivative, an oxadiazole derivative, a pyridine derivative, a benzimidazole derivative, a thiadiazole derivative, an anthracene derivative, a carbodiimide derivative, a quinoxaline derivative, a pyridoindole derivative, a phenanthroline derivative, a silole derivative, or the like in addition to a metal complex of a quinolinol derivative including Alq$_3$ and BAlq can be used. These materials may be deposited alone. However, any of the materials may be mixed with another material and used as a single deposited layer. Further, a stacked structure may be achieved by depositing layers of the plurality of materials alone, or mixing the plurality of materials and depositing layers thereof. Alternatively, a stacked structure of at least one layer of any of the plurality of materials deposited alone and at least one layer obtained by mixing the plurality of materials and depositing at least one layer thereof may be achieved. These materials can be formed into a thin film by a known method such as a spin coat method and an ink jet method in addition to a vapor deposition method.

For the electron injection layer of the organic EL device according to the present invention, an alkali metal salt such as lithium fluoride and cesium fluoride, an alkaline earth metal salt such as magnesium fluoride, a metal complex of a quinolinol derivative such as lithiumquinolinol, a metal oxide such as an aluminum oxide, a metal such as ytterbium (Yb), samarium (Sm), calcium (Ca), strontium (Sr), and cesium (Cs), or the like can be used. However, this can be omitted in the favorable selection of the electron transport layer and the cathode.

Further, for the electron injection layer or electron transport layer, those obtained by N-doping the material typically used for the layer with a metal such as cesium can be used.

In the cathode of the organic EL device according to the present invention, an electrode material having a low work function, such as aluminum, an alloy having a lower work function, such as a magnesium silver alloy, a magnesium indium alloy, and an aluminum magnesium alloy, or the like is used as the electrode material.

Hereinafter, the embodiment of the present invention will be specifically described by way of Examples. However, the present technology is not limited to the following Examples as long as the essence of the present invention is not exceeded.

Example 1

Synthesis of 4,6-bis (biphenyl-3-yl)-2-([1,1',3',1''] terphenyl-4-yl)-benzoxazole (Compound 6)

4,6-bis(biphenyl-3-yl)-2-(4-chloro-phenyl)-benzoxazole: 10.0 g, 3-biphenylboronic acid: 7.5 g, bis(dibenzylideneacetone) palladium (0): 0.5 g, tricyclohexylphosphine: 1.1 g, and tripotassium phosphate: 12.1 g were charged into a reaction vessel, and stirred under reflux overnight in a 1,4-dioxane/H$_2$O mixed solvent. The mixture was allowed to cool and then separated. Extraction was performed with ethyl acetate from the aqueous layer, and then, the extract was concentrated. The crude product thus obtained was purified by column chromatography (carrier: silica gel, eluent: dichloromethane/ethyl acetate), and then crystallized with acetone. In this way, 8.3 g (yield of 68.0%) of white powder of 4,6-bis (biphenyl-3-yl)-2-([1,1',3', 1''] terphenyl-4-yl)-benzoxazole (Compound 6) was obtained.

(Chem. 20)

(Compound 6)

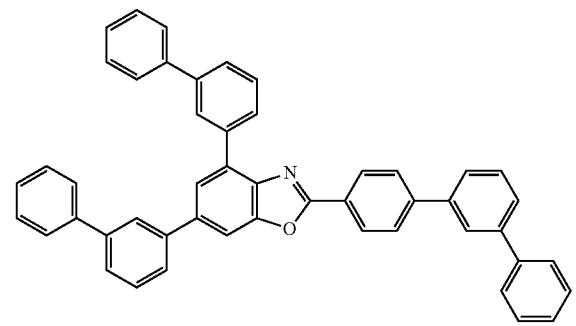

The structure of the obtained white powder was identified using NMR.

The following 33 hydrogen signals were detected by ¹H-NMR (CDCl₃).

δ (ppm)=8.44 (2H), 8.35 (1H), 8.14 (1H), 8.00-7.82 (6H), 7.80-7.47 (20H), 7.46-7.37 (3H).

Example 2

Synthesis of 2-{3,5-di([9H]-carbazol-9-yl)-phenyl}-4,6-diphenyl-benzoxazole (Compound 22)

By using 2-(3,5-dichloro-phenyl)-4,6-diphenyl-benzoxazole and carbazole instead of 4,6-bis(biphenyl-3-yl)-2-(4-chloro-phenyl)-benzoxazole and 3-biphenylboronic acid in Example 1, respectively, and performing the reaction under similar conditions, 4.8 g (yield of 30%) of a white powder of 2-{3,5-di([9H]-carbazol-9-yl)-phenyl}-4,6-diphenyl-benzoxazole (Compound 22) was obtained.

(Chem. 21)

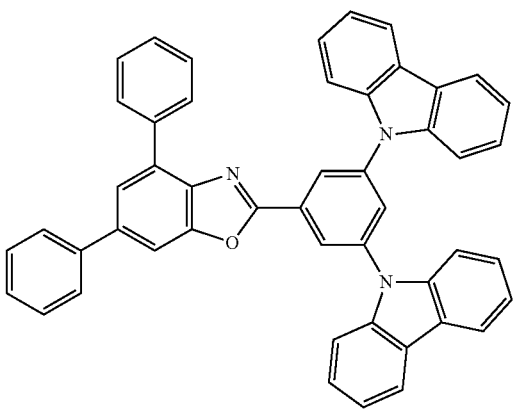

(Compound 22)

The structure of the obtained white powder was identified using NMR.

The following 31 hydrogen signals were detected by ¹H-NMR (CDCl₃).

δ (ppm)=8.67 (2H), 8.21 (4H), 8.10 (2H), 8.01 (1H), 7.85 (1H), 7.79 (1H), 7.73 (2H), 7.63 (4H), 7.57-7.46 (8H), 7.46-7.33 (6H).

Example 3

Synthesis of 2-{2,5-di([9H]-carbazol-9-yl)-phenyl}-4,6-diphenyl-benzoxazole (Compound 24)

2-{2,5-difluoro-phenyl}-4,6-diphenyl-benzoxazole: 3.7 g, carbazole: 3.4 g, and cesium carbonate: 12.9 g were charged into a reaction vessel, and heated and stirred overnight at 120° C. in a DMF solvent. The mixture was allowed to cool, and then H₂O was added thereto. Then, the precipitated solid was collected to obtain a crude product. The crude product was crystallized and purified with a monochlorobenzene/acetone mixed solvent, and thus, 4.3 g (yield of 64%) of white powder of 2-{2,5-di([9H]-carbazol-9-yl)-phenyl}-4,6-diphenyl-benzoxazole (Compound 24) was obtained.

(Chem. 22)

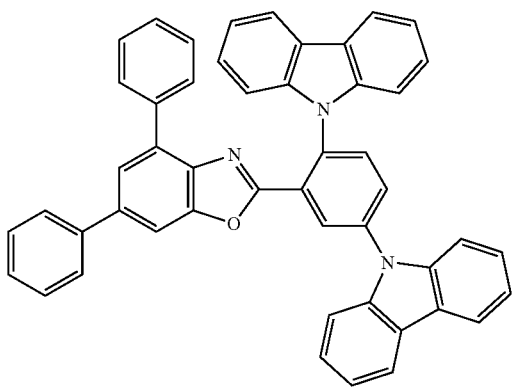

(Compound 24)

The structure of the obtained white powder was identified using NMR.

The following 31 hydrogen signals were detected by ¹H-NMR (CDCl₃).

δ (ppm)=8.81 (1H), 8.25 (4H), 8.02 (1H), 7.94 (1H), 7.69 (2H), 7.63 (1H), 7.56 (2H), 7.55 (2H), 7.48-7.29 (17H).

Example 4

Synthesis of 4,6-bis(biphenyl-3-yl)-2-{([9H]-carbazol-9-yl)-phenyl}-benzoxazole (Compound 45)

By using carbazole instead of 3-biphenylboronic acid in Example 1 and performing the reaction under similar conditions, 4.2 g (yield of 34%) of white powder of 4,6-bis(biphenyl-3-yl)-2-{([9H]-carbazol-9-yl)-phenyl}-benzoxazole (Compound 45) was obtained.

(Chem. 23)

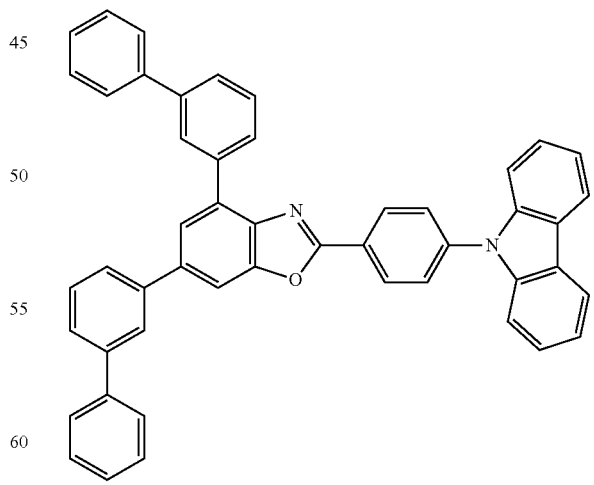

(Compound 45)

The structure of the obtained white powder was identified using NMR.

The following 32 hydrogen signals were detected by ¹H-NMR (CDCl₃).

δ (ppm)=8.59 (2H), 8.36 (1H), 8.19 (2H), 8.15 (1H), 7.97 (1H), 7.92 (1H), 7.94-7.32 (23H).

Example 5

Synthesis of 4,6-bis(biphenyl-3-yl)-2-{4-(9-phenyl-[9H]-carbazol-3-yl)-phenyl}-benzoxazole (Compound 47)

By using 3-(9-phenyl-[9H]-carbazole)-boronic acid instead of 3-biphenylboronic acid in Example 1 and performing the reaction under similar conditions, 3.8 g (yield of 27%) of pale yellow powder of 4,6-bis(biphenyl-3-yl)-2-{4-(9-phenyl-[9H]-carbazol-3-yl)-phenyl}-benzoxazole (Compound 47) was obtained.

(Chem. 24)

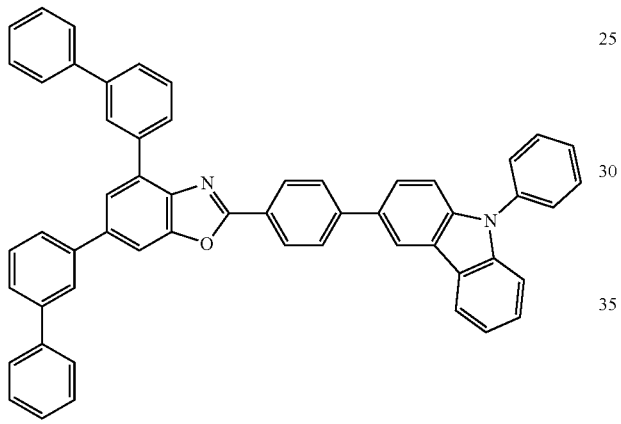

(Compound 47)

The structure of the obtained pale yellow powder was identified using NMR.

The following 36 hydrogen signals were detected by $^1$H-NMR (CDCl$_3$).

δ (ppm)=8.47 (1H), 8.45 (2H), 8.37 (1H), 8.25 (1H), 8.15 (1H), 7.92 (5H), 7.82-7.59 (14H), 7.58-7.33 (11H).

Example 6

Synthesis of 2,6-diphenyl-4-(9,9'-spirobi[9H]fluoren-2-yl)-benzoxazole (Compound 57)

By using 6-Chloro-2-phenyl-4-(9,9'-spirobi[9H]fluoren-2-yl)-benzoxazole and phenylboronic acid instead of 4,6-bis(biphenyl-3-yl)-2-(4-chloro-phenyl)-benzoxazole and 3-biphenylboronic acid in Example 1, respectively, and performing the reaction under similar conditions, 4.5 g (yield of 41%) of white powder of 2,6-diphenyl-4-(9,9'-spirobi[9H]fluoren-2-yl)-benzoxazole (Compound 57) was obtained.

(Chem. 25)

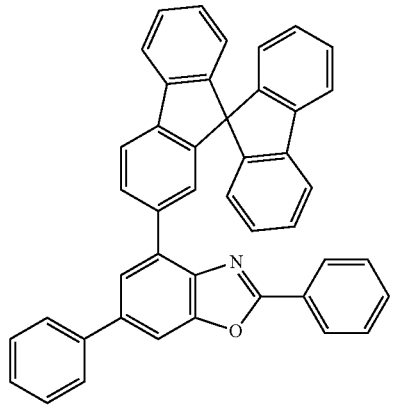

(Compound 57)

The structure of the obtained white powder was identified using NMR.

The following 27 hydrogen signals were detected by $^1$H-NMR (CDCl$_3$).

δ (ppm)=8.15-7.98 (6H) 7.97-7.85 (4H), 7.60-7.36 (9H), 7.17 (4H), 6.90-6.80 (4H).

Example 7

<Synthesis of <6-(Biphenyl-3-yl)-2-(biphenyl-4-yl)-4-(9-phenyl-[9H]-carbazol-3-yl)-benzoxazole (Compound 60)>

By using 6-(biphenyl-3-yl)-2-(4-chlorophenyl)-4-(9-phenyl-[9H]-carbazol-3-yl)-benzoxazole and phenylboronic acid instead of 4,6-bis(biphenyl-3-yl)-2-(4-chloro-phenyl)-benzoxazole and 3-biphenylboronic acid in Example 1, respectively, and performing the reaction under similar conditions, 3.0 g (yield of 44%) of white powder of 6-(Biphenyl-3-yl)-2-(biphenyl-4-yl)-4-(9-phenyl-[9H]-carbazol-3-yl)-benzoxazole (Compound 60) was obtained.

(Chem. 26)

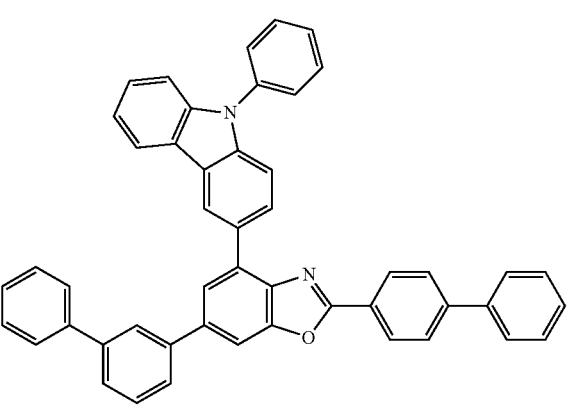

(Compound 60)

The structure of the obtained white powder was identified using NMR.

The following 32 hydrogen signals were detected by $^1$H-NMR (CDCl$_3$).

δ (ppm)=8.90 (1H), 8.45 (2H), 8.30 (1H), 8.26 (1H), 7.94 (1H), 7.91 (1H), 7.85 (2H), 7.80 (3H), 7.74-7.32 (20H).

Example 8

Synthesis of 4-{3,5-di([9H]-carbazol-9-yl)-phenyl}-2,6-diphenyl-benzoxazole (Compound 62)

By using 6-chloro-4-{3,5-di([9H]-carbazol-9-yl)-phenyl}-2-phenyl-benzoxazole and phenylboronic acid instead of 4,6-bis(biphenyl-3-yl)-2-(4-chloro-phenyl)-benzoxazole and 3-biphenylboronic acid in Example 1, respectively, and performing the reaction under similar conditions, 8.0 g (yield of 60%) of white powder of 4-{3,5-di([9H]-carbazol-9-yl)-phenyl}-2,6-diphenyl-benzoxazole (Compound 62) was obtained.

(Chem. 27)

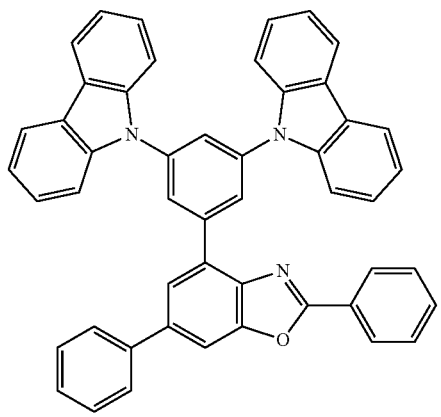

(Compound 62)

The structure of the obtained white powder was identified using NMR.

The following 31 hydrogen signals were detected by $^1$H-NMR (CDCl$_3$).

δ (ppm)=8.52 (2H), 8.42 (2H), 8.21 (4H), 7.91 (1H), 7.90 (1H), 7.87 (1H), 7.85 (4H), 7.71 (2H), 7.65-7.46 (9H), 7.45-7.34 (5H).

Example 9

Synthesis of 6-{3,5-di([9H]-carbazol-9-yl)-phenyl}-2,4-diphenyl-benzoxazole (Compound 69)

By using 6-chloro-2,4-diphenyl-benzoxazole and 3,5-di([9H]-carbazol-9-yl)-phenylboronic acid instead of 4,6-bis(biphenyl-3-yl)-2-(4-chloro-phenyl)-benzoxazole and 3-biphenylboronic acid in Example 1, respectively, and performing the reaction under similar conditions, 6.8 g (yield of 61%) of white powder of 6-{3,5-di([9H]-carbazol-9-yl)-phenyl}-2,4-diphenyl-benzoxazole (Compound 69) was obtained.

(Chem. 28)

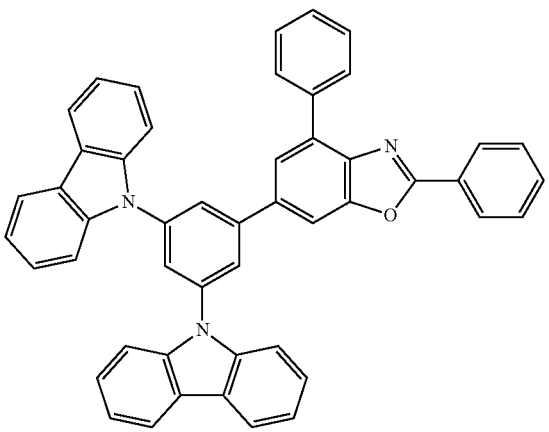

(Compound 69)

The structure of the obtained white powder was identified using NMR.

The following 31 hydrogen signals were detected by $^1$H-NMR (CDCl$_3$).

δ (ppm)=8.35 (2H), 8.21 (4H), 8.11 (2H), 8.07 (2H), 7.91 (2H), 7.88 (1H), 7.66 (4H), 7.59-7.42 (10H), 7.36 (4H).

Example 10

Synthesis of 2-Phenyl-6-(9-phenyl-[9H]-carbazol-3-yl)-4-(5-phenyl-[5H]-pyrido[4,3,b]indol-8-yl)-benzoxazole (Compound 82)

By using 6-chloro-2-phenyl-4-(5-phenyl-[5H]-pyrido[4,3,b]indol-8-yl)-benzoxazole and 9-phenyl-[9H]-carbazol-3-yl-boronic acid instead of 4,6-bis(biphenyl-3-yl)-2-(4-chloro-phenyl)-benzoxazole and 3-biphenylboronic acid in Example 1, respectively, and performing the reaction under similar conditions, 2.9 g (yield of 50%) of yellow powder of 2-Phenyl-6-(9-phenyl-[9H]-carbazol-3-yl)-4-(5-phenyl-[5H]-pyrido[4,3,b]indol-8-yl)-benzoxazole (Compound 82) was obtained.

(Chem. 29)

(Compound 82)

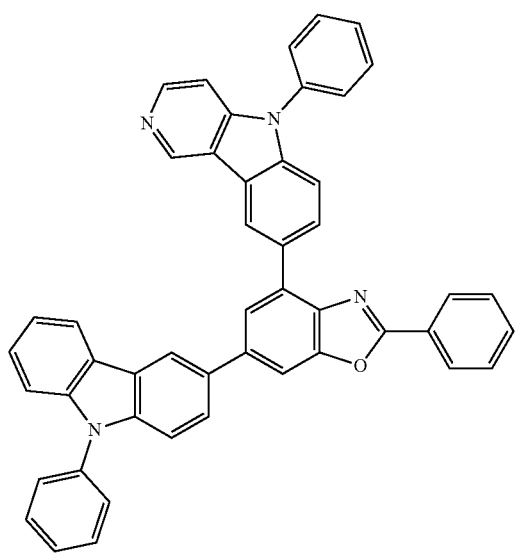

The structure of the obtained yellow powder was identified using NMR.

The following 30 hydrogen signals were detected by $^1$H-NMR (CDCl$_3$).

δ (ppm)=9.56 (1H), 9.04 (1H), 8.59 (1H), 8.53 (1H), 8.48 (1H), 8.45 (1H), 8.36 (1H), 8.26 (2H), 8.05 (1H), 7.93 (2H), 7.88-7.43 (16H), 7.36 (2H).

Example 11

Synthesis of 2-{3,5-di([9H]-carbazol-9-yl)-phenyl}-benzoxazole (Compound 96)

By using 2-(3,5-dichloro-phenyl)-benzoxazole and carbazole instead of 4,6-bis(biphenyl-3-yl)-2-(4-chloro-phenyl)-benzoxazole and 3-biphenylboronic acid in Example 1, respectively, and performing the reaction under similar conditions, 10.6 g (yield of 67%) of white powder of 2-{3,5-di([9H]-carbazol-9-yl)-phenyl}-benzoxazole (Compound 96) was obtained.

(Chem. 30)

(Compound 96)

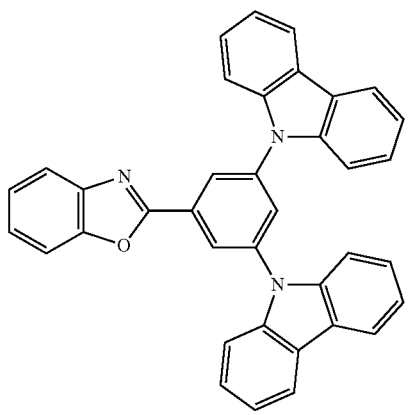

The structure of the obtained white powder was identified using NMR.

The following 23 hydrogen signals were detected by $^1$H-NMR (CDCl$_3$).

δ (ppm)=8.64 (2H), 8.21 (4H), 8.03 (1H), 7.87 (1H), 7.64 (5H), 7.51 (4H), 7.47-7.32 (6H).

Example 12

Synthesis of 2-{3,5-di([9H]-carbazol-9-yl)-biphenyl-4'-yl}-benzoxazole (Compound 97)

2-(4-bromophenyl)-benzoxazole: 4.0 g, and 3,5-di([9H]-carbazol-9-yl)-phenylboronic acid: 7.3 g were charged into a reaction vessel, toluene: 80 mL, ethanol: 20 mL, and then an aqueous solution prepared by dissolving potassium carbonate; 2.4 g in H$_2$O: 20 mL in advance were added thereto, and nitrogen gas was aerated while applying ultrasonic waves for 30 minutes. Tetrakis (triphenylphosphine) palladium (0): 0.3 g was added thereto, and the mixture was stirred overnight with heating under reflux. The mixture was allowed to cool and then, an organic layer was separated by a liquid separation operation and concentrated to obtain a crude product. The crude product was crystallized and purified with a toluene/acetone mixed solvent, and thus, 4.4 g (yield of 50%) of white powder of 2-{3,5-di([9H]-carbazol-9-yl)-biphenyl-4'-yl}-benzoxazole (Compound 97) was obtained.

(Chem. 31)

(Compound 97)

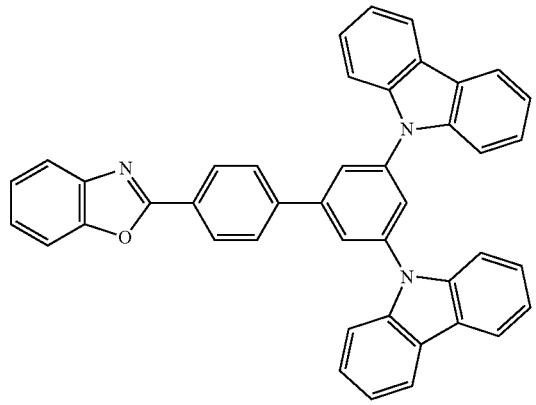

The structure of the obtained white powder was identified using NMR.

The following 27 hydrogen signals were detected by $^1$H-NMR (CDCl$_3$).

δ (ppm)=8.42 (2H), 8.21 (4H), 8.04 (2H), 7.91 (3H), 7.82 (1H), 7.64 (5H), 7.51 (4H), 7.45-7.32 (6H).

Example 13

Synthesis of 2-{3,5-di([9H]-carbazol-9-yl)-phenyl}-6-(biphenyl-4-yl)-4-phenyl-benzoxazole (Compound 98)

By using 2-(3,5-dichloro-phenyl)-6-(biphenyl-4-yl)-4-phenyl-benzoxazole and carbazole instead of 4,6-bis(biphenyl-3-yl)-2-(4-chloro-phenyl)-benzoxazole and 3-biphenylboronic acid in Example 1, respectively, and performing the reaction under similar conditions, 7.9 g (yield of 57%) of white powder of 2-{3,5-di([9H]-carbazol-9-yl)-phenyl}-6-(biphenyl-4-yl)-4-phenyl-benzoxazole (Compound 98) was obtained.

(Chem. 32)

(Compound 98)

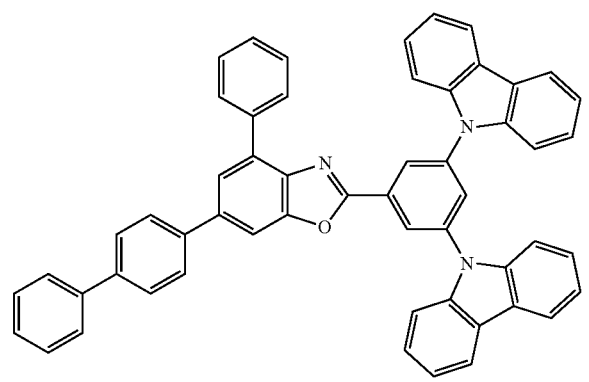

The structure of the obtained white powder was identified using NMR.

The following 35 hydrogen signals were detected by $^1$H-NMR (CDCl$_3$).

δ (ppm)=8.68 (2H), 8.22 (4H), 8.11 (2H), 8.01 (1H), 7.87 (2H), 7.79 (4H), 7.69 (2H), 7.64 (4H), 7.57-7.47 (8H), 7.42 (2H), 7.38 (4H).

Example 14

Synthesis of 2-{3,4-di([9H]-carbazol-9-yl)-phenyl}-4,6-diphenyl-benzoxazole (Compound 99)

By using 2-{3,4-difluoro-phenyl}-4,6-diphenyl-benzoxazole instead of 2-{2,5-difluoro-phenyl}-4,6-diphenyl-benzoxazole in Example 3 and performing the reaction under similar conditions, 3.1 g (yield of 60%) of white powder of 2-{3,4-di([9H]-carbazol-9-yl)-phenyl}-4,6-diphenyl-benzoxazole (Compound 99) was obtained.

(Chem. 33)

(Compound 99)

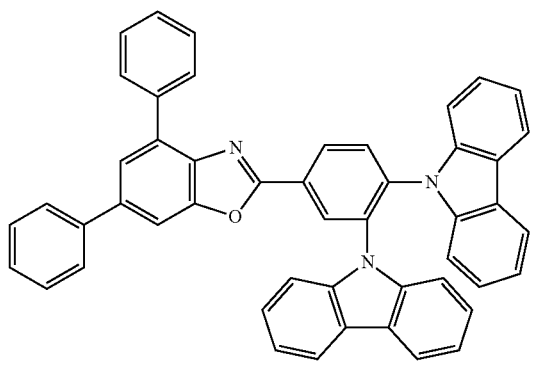

The structure of the obtained white powder was identified using NMR.

The following 31 hydrogen signals were detected by $^1$H-NMR (CDCl$_3$).

δ (ppm)=8.79 (1H), 8.67 (1H), 8.14 (2H), 8.04 (1H), 7.89-7.79 (6H), 7.75 (2H), 7.56 (4H), 7.45 (2H), 7.24 (4H), 7.15-7.06 (8H).

Example 15

Synthesis of 4-(biphenyl-3-yl)-2-(biphenyl-4-yl)-6-(9-phenyl-[9H]-carbazol-3-yl)-benzoxazole (Compound 100)

By using 4-(biphenyl-3-yl)-2-(4-chlorophenyl)-6-(9-phenyl-[9H]-carbazol-3-yl)-benzoxazole and phenylboronic acid instead of 4,6-bis(biphenyl-3-yl)-2-(4-chloro-phenyl)-benzoxazole and 3-biphenylboronic acid in Example 1, respectively, and performing the reaction under similar conditions, 2.1 g (yield of 31%) of white powder of 4-(biphenyl-3-yl)-2-(biphenyl-4-yl)-6-(9-phenyl-[9H]-carbazol-3-yl)-benzoxazole (Compound 100) was obtained.

(Chem. 34)

(Compound 100)

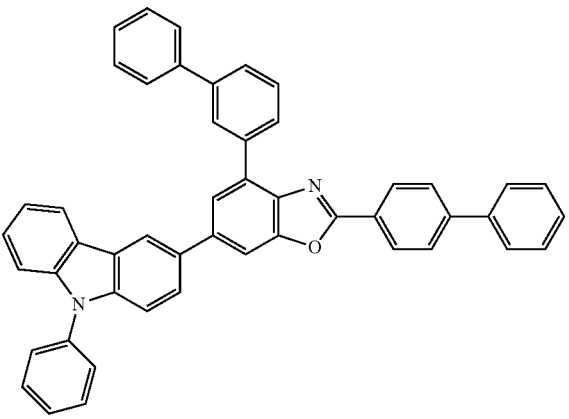

The structure of the obtained white powder was identified using NMR.

The following 32 hydrogen signals were detected by $^1$H-NMR (CDCl$_3$).

δ (ppm)=8.47 (1H), 8.50 (2H), 8.36 (1H), 8.25 (1H), 8.16 (1H), 7.92 (2H), 7.85 (2H), 7.77 (5H), 7.72-7.59 (6H), 7.57-7.33 (11H).

Example 16

The melting point and the glass transition point of the benzoazole compound represented by the general formula (1) were measured using a high sensitivity differential scanning calorimeter (DSC3100SA manufactured by Bruker AXS GmbH).

| transition point | Melting point | Glass |
|---|---|---|
| Compound of Example 1 | Not observed | 82° C. |
| Compound of Example 2 | 273° C. | 144° C. |
| Compound of Example 3 | 256° C. | 136° C. |
| Compound of Example 4 | Not observed | 107° C. |
| Compound of Example 5 | 220° C. | 112° C. |
| Compound of Example 6 | 242° C. | 121° C. |
| Compound of Example 7 | 236° C. | 113° C. |
| Compound of Example 8 | 313° C. | 144° C. |
| Compound of Example 9 | 277° C. | 145° C. |

| transition point | Melting point | Glass |
|---|---|---|
| Compound of Example 10 | Not observed | 180° C. |
| Compound of Example 11 | 261° C. | 117° C. |
| Compound of Example 12 | 243° C. | 135° C. |
| Compound of Example 13 | 315° C. | 162° C. |
| Compound of Example 14 | 270° C. | 144° C. |
| Compound of Example 15 | Not observed | 111° C. |

The compound having a benzoazole structure represented by the general formula (1) has the glass transition point of not less than 100° C., which shows that the thin film state is stable.

Example 17

The compound having a benzoazole structure represented by the general formula (1) was used to prepare a vapor deposition film having a film thickness of 100 nm on an ITO substrate, and the work function thereof was measured by an ionization potential measuring apparatus (PYS-202 manufactured by Sumitomo Heavy Industries, Ltd.).

|  | Work function |
|---|---|
| Compound of Example 1 | 6.34 eV |
| Compound of Example 2 | 6.28 eV |
| Compound of Example 3 | 6.12 eV |
| Compound of Example 4 | 6.20 eV |
| Compound of Example 5 | 6.00 eV |
| Compound of Example 6 | 6.46 eV |
| Compound of Example 7 | 5.98 eV |
| Compound of Example 8 | 6.18 eV |
| Compound of Example 9 | 6.21 eV |
| Compound of Example 10 | 5.94 eV |
| Compound of Example 11 | 6.24 eV |
| Compound of Example 12 | 6.24 eV |
| Compound of Example 13 | 6.32 eV |
| Compound of Example 14 | 6.18 eV |
| Compound of Example 15 | 6.02 eV |

The compound having a benzoazole structure represented by the general formula (1) has a value of work function larger than 5.5 eV that is a value of work function of a general hole transport material such as NPD and TPD and has large hole blocking performance.

Example 18

Figure 26:
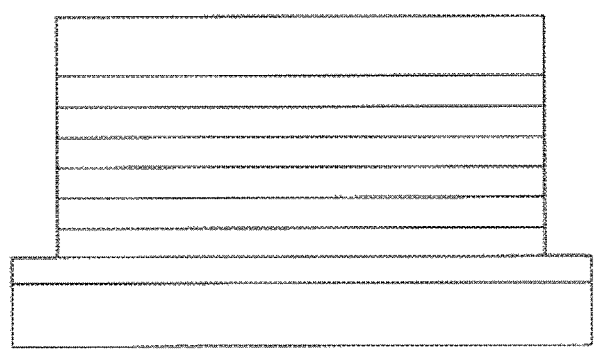
FIG. 26 is a diagram showing a configuration of each of organic EL devices according to Examples 18 to 26 and Comparative Examples 1 and 2.

The organic EL device was prepared by depositing a hole injection layer 3, a hole transport layer 4, a light-emitting layer 5, a hole blocking layer 6, an electron transport layer 7, an electron injection layer 8, and a cathode (aluminum electrode) 9 in the stated order on a transparent anode 2, which has been formed on a glass substrate 1 as an ITO electrode in advance, as shown in FIG. 26.

Specifically, after performing, in isopropyl alcohol for 20 minutes, ultrasonic cleaning on the glass substrate 1 on which ITO having a film thickness of 150 nm was formed, the glass substrate 1 was dried for 10 minutes on a hot plate heated to 200° C. After that, UV ozone treatment was performed for 15 minutes, and then, the ITO-attached glass substrate was mounted in a vacuum deposition machine. The pressure in the vacuum deposition machine was reduced to not more than 0.001 Pa. Subsequently, a film of an electron acceptor (Acceptor-1) having the following structural formula and a compound (HTM-1-1) having the following structural formula were formed, as the hole injection layer 3, to have a film thickness of 10 nm and cover the transparent anode 2 by binary deposition at a deposition rate in which the ratio of the deposition rates of Acceptor-1 and the compound (HTM-1-1) was 3:97. As the hole transport layer 4, a film of the compound (HTM-1-1) having the following structural formula was formed on the hole injection layer 3 to have a film thickness of 60 nm. A film of a compound EMD-1 having the following structural formula and a compound EMH-1 having the following structural formula were formed, as the light-emitting layer 5, on the hole transport layer 4 to have a film thickness of 20 nm by binary deposition at a deposition rate in which the ratio of the deposition rates of EMD-1 and EMH-1 was 5:95. A film of the compound (Compound 22) according to Example 2 was formed on the light-emitting layer 5, as the hole blocking layer 6 to have a film thickness of 5 nm. A film of a compound (ETM-2-87) having the following structural formula and a compound (ETM-3) having the following structural formula were formed, as the electron transport layer 7, on the hole blocking layer 6 to have a film thickness of 25 nm by binary deposition at a deposition rate in which the ratio of the deposition rates of the compound (ETM-2-87) and the compound ETM-3 was 50:50. A film of lithium fluoride was formed, as the electron injection layer 8, on the electron transport layer 7 to have a film thickness of 1 nm. Finally, aluminum was deposited to have a thickness of 100 nm to form the cathode 9. The characteristics of the prepared organic EL device were measured at room temperature in the atmosphere. The measurement results of the light-emitting characteristics when a direct current voltage was applied to the prepared organic EL device were collectively shown in Table 1.

(Chem. 35)

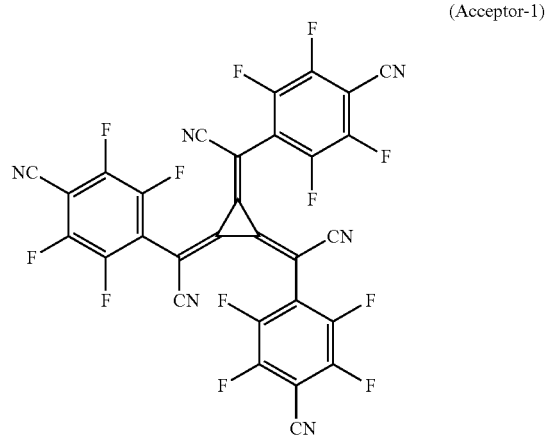

(Acceptor-1)

(Chem. 36)
(HTM-1-1)
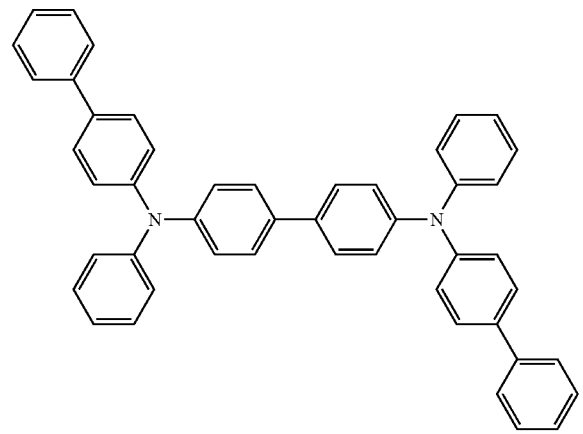
(Chem. 38)
(EMH-1)
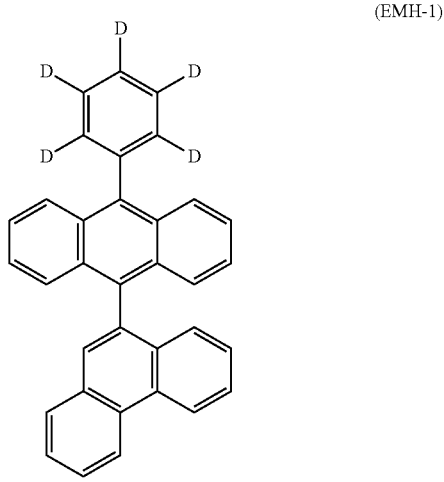
(Chem. 39)
(Compound 22)
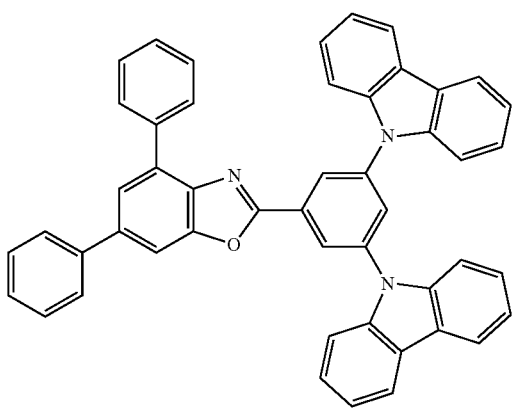
(Chem. 37)
(EMD-1)
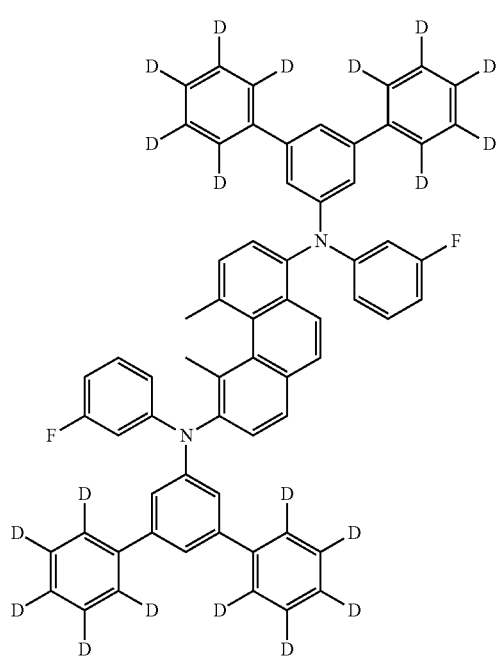
(Chem. 40)
(ETM-2-87)
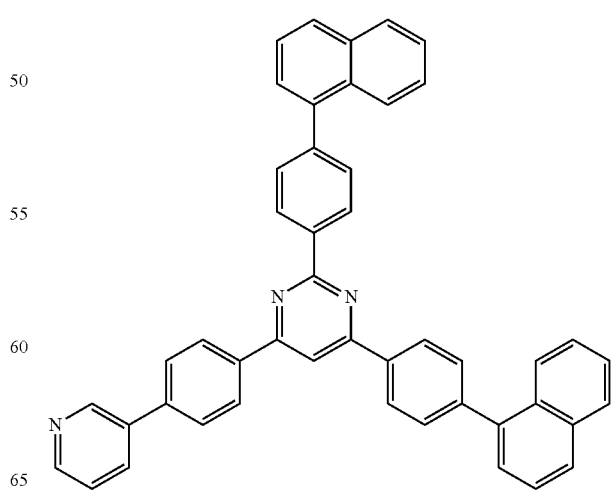

(Chem. 41)

(ETM-3)

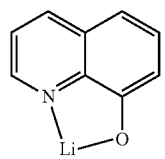

Example 19

An organic EL device was prepared in similar conditions to Example 18 except that the compound (Compound 24) according to Example 3 of the present invention was used as the material of the hole blocking layer 6 instead of the compound (Compound 22) according to Example 2 of the present invention. The characteristics of the prepared organic EL device were measured at room temperature in the atmosphere. The measurement results of the light-emitting characteristics when a direct current voltage was applied to the prepared organic EL device were collectively shown in Table 1.

(Chem. 42)

(Compound 24)

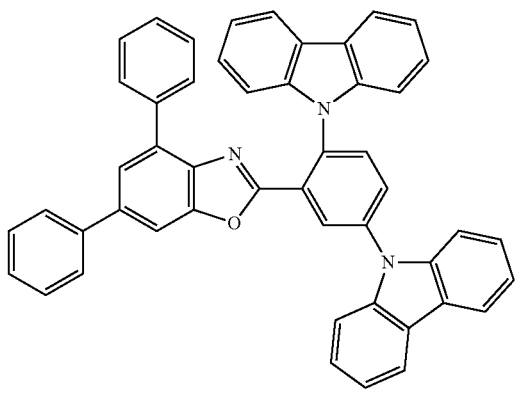

Example 20

An organic EL device was prepared in similar conditions to Example 18 except that the compound (Compound 60) according to Example 7 of the present invention was used as the material of the hole blocking layer 6 instead of the compound (Compound 22) according to Example 2 of the present invention. The characteristics of the prepared organic EL device were measured at room temperature in the atmosphere. The measurement results of the light-emitting characteristics when a direct current voltage was applied to the prepared organic EL device were collectively shown in Table 1.

(Chem. 43)

(Compound 60)

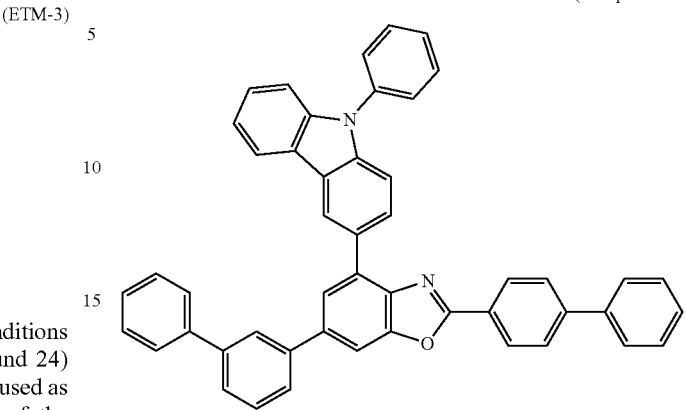

Example 21

An organic EL device was prepared in similar conditions to Example 18 except that the compound (Compound 62) according to Example 8 of the present invention was used as the material of the hole blocking layer 6 instead of the compound (Compound 22) according to Example 2 of the present invention. The characteristics of the prepared organic EL device were measured at room temperature in the atmosphere. The measurement results of the light-emitting characteristics when a direct current voltage was applied to the prepared organic EL device were collectively shown in Table 1.

(Chem. 44)

(Compound 62)

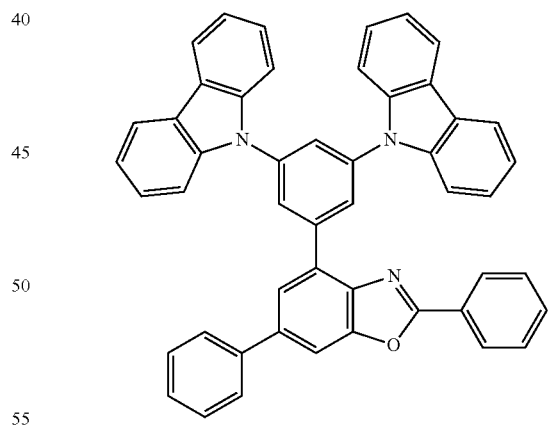

Example 22

An organic EL device was prepared in similar conditions to Example 18 except for the compound (Compound 69) according to Example 9 of the present invention was used as the material of the hole blocking layer 6 instead of the compound (Compound 22) according to Example 2 of the present invention. The characteristics of the prepared organic EL device were measured at room temperature in the atmosphere. The measurement results of the light-emitting characteristics when a direct current voltage was applied to the prepared organic EL device were collectively shown in Table 1.

(Chem. 45)

(Compound 69)

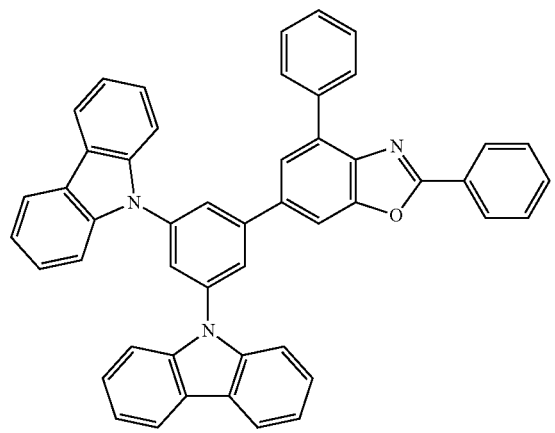

Example 23

An organic EL device was prepared in similar conditions to Example 18 except that the compound (Compound 96) according to Example 11 of the present invention was used as the material of the hole blocking layer 6 instead of the compound (Compound 22) according to Example 2 of the present invention. The characteristics of the prepared organic EL device were measured at room temperature in the atmosphere. The measurement results of the light-emitting characteristics when a direct current voltage was applied to the prepared organic EL device were collectively shown in Table 1.

(Chem. 46)

(Compound 96)

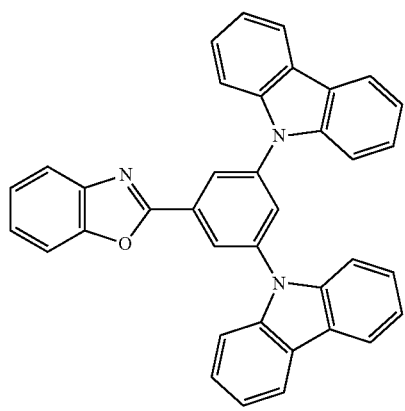

Example 24

An organic EL device was prepared in similar conditions to Example 18 except that the compound (Compound 97) according to Example 12 of the present invention was used as the material of the hole blocking layer 6 instead of the compound (Compound 22) according to Example 2 of the present invention. The characteristics of the prepared organic EL device were measured at room temperature in the atmosphere. The measurement results of the light-emitting characteristics when a direct current voltage was applied to the prepared organic EL device were collectively shown in Table 1.

(Chem. 47)

(Compound 97)

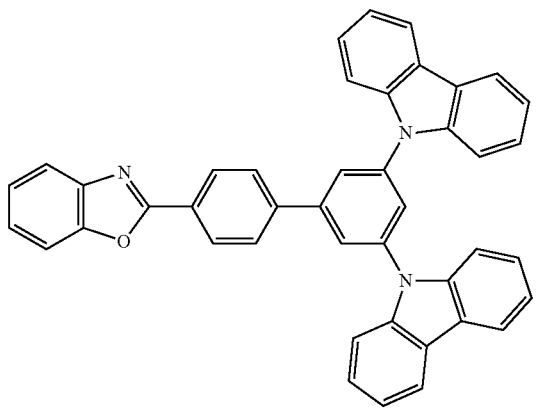

Example 25

An organic EL device was prepared in similar conditions to Example 18 except that the compound (Compound 98) according to Example 13 of the present invention was used as the material of the hole blocking layer 6 instead of the compound (Compound 22) according to Example 2 of the present invention. The characteristics of the prepared organic EL device were measured at room temperature in the atmosphere. The measurement results of the light-emitting characteristics when a direct current voltage was applied to the prepared organic EL device were collectively shown in Table 1.

(Chem. 48)

(Compound 98)

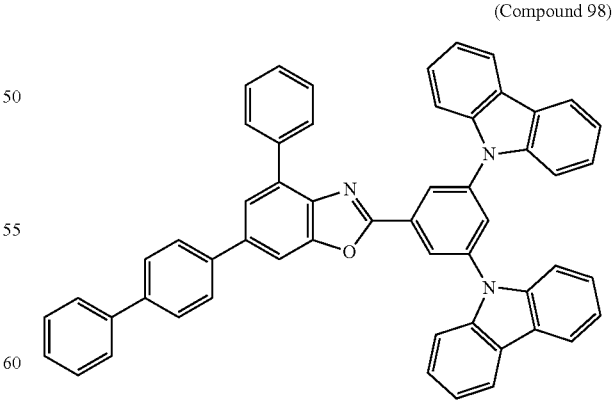

Example 26

An organic EL device was prepared in similar conditions to Example 18 except that the compound (Compound 99)

according to Example 14 of the present invention was used as the material of the hole blocking layer 6 instead of the compound (Compound 22) according to Example 2 of the present invention. The characteristics of the prepared organic EL device were measured at room temperature in the atmosphere. The measurement results of the light-emitting characteristics when a direct current voltage was applied to the prepared organic EL device were collectively shown in Table 1.

(Chem. 49)

(Compound 99)

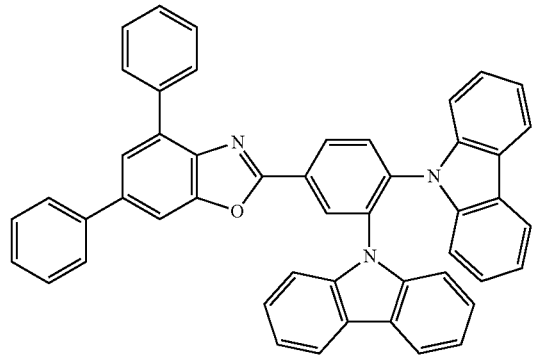

Comparative Example 1

For comparison, an organic EL device was prepared in similar conditions to Example 18 except that a compound ETM-4 having the following structural formula was used as the material of the hole blocking layer 6 instead of the compound (Compound 22) according to Example 2 of the present invention. The characteristics of the prepared organic EL device were measured at room temperature in the atmosphere. The measurement results of the light-emitting characteristics when a direct current voltage was applied to the prepared organic EL device were collectively shown in Table 1.

(Chem. 50)

(ETM-4)

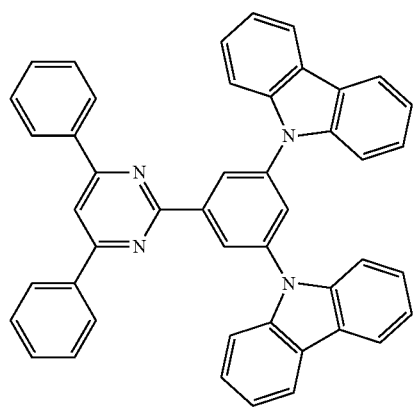

Comparative Example 2

For comparison, an organic EL device was prepared in similar conditions to Example 18 except that the above-mentioned compound (ETM-2-87) was used as the material of the hole blocking layer 6 instead of the compound (Compound 22) according to Example 2 of the present invention. The characteristics of the prepared organic EL device were measured at room temperature in the atmosphere. The measurement results of the light-emitting characteristics when a direct current voltage was applied to the prepared organic EL device were collectively shown in Table 1.

(Chem. 51)

(ETM-2-87)

The device lifetime was measured using each of the organic EL devices prepared in Examples 18 and 26 and Comparative Examples 1 and 2, and the results were collectively shown in Table 1. The device lifetime was measured as the time until the light emission luminance attenuated to 1900 cd/m$^2$ (corresponding to 95% in the case where the initial luminance was 100%: 95% attenuation) when constant current driving was performed with the light emission luminance (initial luminance) at the start of light emission set to 2000 cd/m$^2$.

TABLE 1

|  | Hole blocking layer | Voltage [V] (@ 10 mA/cm²) | Luminance [cd/m²] (@ 10 mA/cm²) | Light emission efficiency [cd/A] (@ 10 mA/cm²) | Power efficiency [lm/W] (@ 10 mA/cm²) | Device lifetime 95% attenuated |
|---|---|---|---|---|---|---|
| Example 18 | Compound 22 | 3.48 | 1008 | 10.08 | 9.11 | 235 hours |
| Example 19 | Compound 24 | 3.52 | 1004 | 10.04 | 8.97 | 212 hours |
| Example 20 | Compound 60 | 3.49 | 1009 | 10.09 | 9.10 | 151 hours |
| Example 21 | Compound 62 | 3.50 | 980 | 9.80 | 8.81 | 204 hours |
| Example 22 | Compound 69 | 3.52 | 985 | 9.85 | 8.80 | 272 hours |
| Example 23 | Compound 96 | 3.51 | 999 | 9.99 | 8.95 | 217 hours |
| Example 24 | Compound 97 | 3.47 | 1010 | 10.10 | 9.16 | 195 hours |
| Example 25 | Compound 98 | 3.52 | 985 | 9.85 | 8.81 | 256 hours |
| Example 26 | Compound 99 | 3.52 | 1007 | 10.07 | 8.99 | 227 hours |
| Comparative Example 1 | ETM-4 | 3.53 | 966 | 9.66 | 8.60 | 117 hours |
| Comparative Example 2 | ETM-2-87 | 3.66 | 900 | 9.00 | 7.74 | 137 hours |

As shown in Table 1, the drive voltage when a current having a current density of 10 mA/cm² was caused to flow was lowered to 3.47 to 3.52 V in the organic EL devices according to Examples 18 to 26 as compared with the 3.53 to 3.66 V of the organic EL devices according to Comparative Examples 1 and 2. Further, the light emission efficiency was improved to 9.80 to 10.10 cd/A in the organic EL devices according to Examples 18 to 26 as compared with 9.00~9.66 cd/A of the organic EL devices according to Comparative Examples 1 and 2. Also the power efficiency of the organic EL devices according to Examples 18 to 26 was largely improved to 8.80 to 9.16 lm/W as compared with 7.74 to 8.60 lm/W of the organic EL devices according to Comparative Examples 1 and 2. In particular, the device lifetime (95% attenuation) was largely extended to 151 to 272 hours in the organic EL devices according to Examples 18 to 26 as compared with 117 to 137 hours of the organic EL devices according to Comparative Examples 1 and 2.

As described above, the organic EL device according to the present invention is excellent in the light emission efficiency and power efficiency as compared with the existing organic EL devices because hole blocking performance, hole resistance performance, and exciton confinement performance are improved by selecting a specific benzoazole-based compound as the material of a hole blocking layer. Thus, it has been found that it is possible to realize an organic EL device having a long lifetime.

INDUSTRIAL APPLICABILITY

The compound having a specific benzoazole structure according to the present invention is excellent in electron injection property and hole blocking performance and is stable in a thin film state, and thus is suitably used as a compound for organic EL device. By preparing an organic EL device using the compound, it is possible to achieve high efficiency, reduce the drive voltage, and improve the durability. For example, it has become possible to expand to home appliances and lighting applications.

REFERENCE SIGNS LIST 1 glass substrate
2 transparent anode
3 hole injection layer
4 hole transport layer
5 light-emitting layer
6 hole blocking layer
7 electron transport layer
8 electron injection layer
9 cathode
20

The invention claimed is:

1. An organic electroluminescence device (hereinafter, abbreviated as organic EL device) including at least an anode, a hole transport layer, a light-emitting layer, a hole blocking layer, an electron transport layer, and a cathode in this order, characterized in that the hole blocking layer includes a compound having a benzoazole structure represented by the following general formula (1);

(Chem. 1)

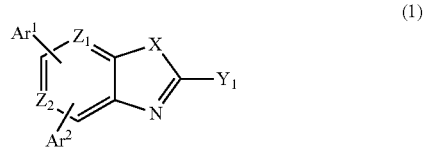

(1)

In the formula, $Ar^1$ and $Ar^2$ may be the same or different from each other and each represent a hydrogen atom, a deuterium atom, a substituted or unsubstituted aromatic hydrocarbon group, a substituted or unsubstituted fused polycyclic aromatic group, or a substituted or unsubstituted aromatic heterocyclic group, $Y_1$ represents a substituted or unsubstituted aromatic hydrocarbon group, a substituted or unsubstituted fused polycyclic aromatic group, a substituted or unsubstituted aromatic heterocyclic group, a straight-chained or branched alkyl group that has 1 to 6 carbon atoms and may have a substituent group, a cycloalkyl group that has 5 to 10 carbon atoms and may have a substituent group, or a straight-chained or branched alkenyl group that has 2 to 6 carbon atoms and may have a substituent group, X represents an oxygen atom or a sulfur atom, and $Z_1$ and $Z_2$ may be the same or different from each other and each represent a carbon atom or a nitrogen atom; and wherein the aromatic heterocyclic group of $Y_1$ is other than a carbazolyl group.

2. The organic EL device according to claim 1, characterized in that
the general formula (1) includes a compound having a benzoazole structure represented by the following general formula (2);

(Chem. 2)

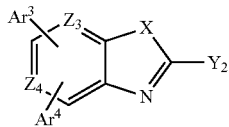

(2)

In the formula, $Ar^3$ and $Ar^4$ may be the same or different from each other and each represent a hydrogen atom, a deuterium atom, a substituted or unsubstituted aromatic hydrocarbon group, or a substituted or unsubstituted aromatic heterocyclic group, $Y_2$ represents a substituted or unsubstituted aromatic hydrocarbon group, a substituted or unsubstituted aromatic heterocyclic group, a straight-chained or branched alkyl group that has 1 to 6 carbon atoms and may have a substituent group, a cycloalkyl group that has 5 to 10 carbon atoms and may have a substituent group, or a straight-chained or branched alkenyl group that has 2 to 6 carbon atoms and may have a substituent group, X represents an oxygen atom or a sulfur atom, and $Z_3$ and $Z_4$ may be the same or different from each other and each represent a carbon atom or a nitrogen atom; and
wherein the aromatic heterocyclic group of each of $Ar^3$, $Ar^4$, and $Y_2$ is other than an azine ring, the aromatic heterocyclic group of $Y_2$ is also other than a carbazolyl group, and the substituent group of each of $Ar^3$, $Ar^4$, and $Y_2$ is other than a fused polycyclic aromatic group and an azine ring.

3. The organic EL device according to claim 2, characterized in that
the general formula (2) includes a compound having a benzoazole structure represented by the following general formula (3);

(Chem. 3)

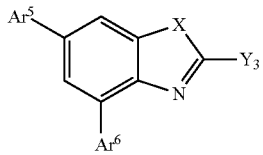

(3)

In the formula, $Ar^5$ and $Ar^6$ may be the same or different from each other and each represent a hydrogen atom, a deuterium atom, a substituted or unsubstituted aromatic hydrocarbon group, or a substituted or unsubstituted aromatic heterocyclic group, $Y_3$ represents a substituted or unsubstituted aromatic hydrocarbon group, a substituted or unsubstituted aromatic heterocyclic group, a straight-chained or branched alkyl group that has 1 to 6 carbon atoms and may have a substituent group, a cycloalkyl group that has 5 to 10 carbon atoms and may have a substituent group, or a straight-chained or branched alkenyl group that has 2 to 6 carbon atoms and may have a substituent group, and X represents an oxygen atom or a sulfur atom; and
wherein the aromatic heterocyclic group of each of $Ar^5$ and $Ar^6$ is other than an azine ring, the aromatic heterocyclic group of $Y_3$ is other than a carbazolyl group and an azine ring, and the substituent group of $Ar^5$, $Ar^6$, and $Y_3$ is other than a fused polycyclic aromatic group and an azine ring.

4. The organic EL device according to claim 3, characterized in that
the general formula (3) includes a compound having a benzoazole structure represented by the following general formula (4);

(Chem. 4)

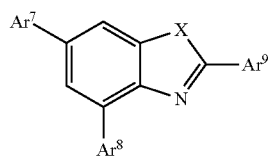

(4)

In the formula, $Ar^7$ to $Ar^8$ may be the same or different from each other and each represent a hydrogen atom, a deuterium atom, a substituted or unsubstituted aromatic hydrocarbon group, or a substituted or unsubstituted aromatic heterocyclic group, $Ar^9$ represents a substituted or unsubstituted aromatic hydrocarbon group, or a substituted or unsubstituted aromatic heterocyclic group, and X represents an oxygen atom or a sulfur atom; and
wherein the aromatic heterocyclic group of each of $Ar^7$ to $Ar^9$ is other than an azine ring, the aromatic heterocyclic group of $Ar^9$ is also other than a carbazolyl group, and the substituent group of each of $Ar^7$ to $Ar^9$ is other than a fused polycyclic aromatic group and an azine ring.

5. The organic EL device according to claim 4, characterized in that
the general formula (4) includes a compound having a benzoazole structure represented by the following general formula (5);

(Chem. 5)

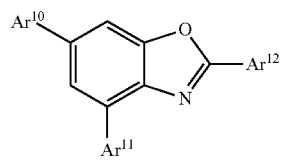

(5)

In the formula, $Ar^{10}$ to $Ar^{11}$ may be the same or different from each other and each represent a hydrogen atom, a deuterium atom, a substituted or unsubstituted aromatic hydrocarbon group, or a substituted or unsubstituted aromatic heterocyclic group; $Ar^{12}$ represents a substituted or unsubstituted aromatic hydrocarbon group, or a substituted or unsubstituted aromatic heterocyclic group; and
wherein the aromatic heterocyclic group of each of $Ar^{10}$ to $Ar^{12}$ is other than an azine ring, the aromatic heterocyclic group of $Ar^{12}$ is also other than a carbazolyl group, and the substituent group $Ar^{10}$ to $Ar^{12}$ is other than a fused polycyclic aromatic group and an azine ring.

6. The organic EL device according to claim 5, characterized in that
the general formula (5) includes a compound having a benzoazole structure represented by the following general formula (6);

(Chem. 6)

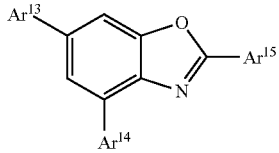

(6)

In the formula, $Ar^{13}$ to $Ar^{14}$ may be the same or different from each other and each represent a hydrogen atom, a deuterium atom, a substituted or unsubstituted aromatic hydrocarbon group, or a substituted or unsubstituted aromatic heterocyclic group; $Ar^{15}$ represents a substituted or unsubstituted aromatic hydrocarbon group, or a substituted or unsubstituted aromatic heterocyclic group; and
wherein the aromatic heterocyclic group of each of $Ar^{13}$ to $Ar^{15}$ is other than an azine ring, the aromatic heterocyclic group of $Ar^{15}$ is also other than a carbazolyl group, the substituent group of each of each of $Ar^{13}$ to $Ar^{15}$ is other than a fused polycyclic aromatic group and an azine ring, and at least one monovalent group represented by the following structural formula (A-1) or (A-2) is included as the aromatic heterocyclic group of each of $Ar^{13}$ to $Ar^{15}$ or the substituent group of each of $Ar^{13}$ to $Ar^{15}$;

(Chem. 7)

(A-1)

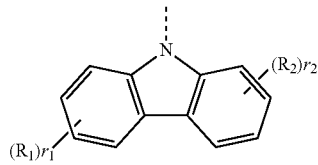

(Chem. 8)

(A-2)

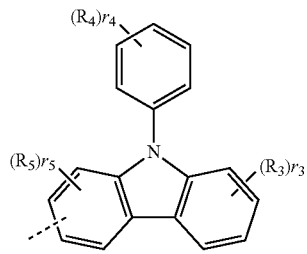

In the formula, a broken line represents a binding site, each of $R_1$ to $R_5$ is a deuterium atom, a fluorine atom, a chlorine atom, a cyano group, a nitro group, a straight-chained or branched alkyl group that has 1 to 6 carbon atoms and may have a substituent group, a cycloalkyl group that has 5 to 10 carbon atoms and may have a substituent group, a straight-chained or branched alkenyl group that has 2 to 6 carbon atoms and may have a substituent group, a straight-chained or branched alkyloxy group that has 1 to 6 carbon atoms and may have a substituent group, a cycloalkyloxy group that has 5 to 10 carbon atoms and may have a substituent group, a substituted or unsubstituted aromatic hydrocarbon group, a substituted or unsubstituted aromatic heterocyclic group, or a substituted or unsubstituted aryloxy group, $r_1$ to $r_5$ may be the same or different from each other, $r_1$ to $r_3$ each represent an integer of 0 to 4, $r_4$ represents an integer of 0 to 5, and $r_5$ represents an integer of 0 to 3; In a case where any of $r_1$ to $r_5$ is an integer of two or more, a plurality of $R_1$, a plurality of $R_2$, a plurality of $R_3$, a plurality of $R_4$, or a plurality of $R_5$ bonded to the same benzene ring may be the same as or different from each other and the plurality of $R_1$, the plurality of $R_2$, the plurality of $R_3$, and the plurality of $R_5$ may be bonded to the same substituted benzene ring via a single bond, a substituted or unsubstituted methylene group, an oxygen atom, or a sulfur atom to form a ring.

7. The organic EL device according to claim 1, characterized in that
the electron transport layer includes a compound having a benzoazole structure represented by the following general formula (ETM-1) or a compound having a pyrimidine ring structure represented by the following general formula (ETM-2);

(Chem. 9)

(ETM-1)

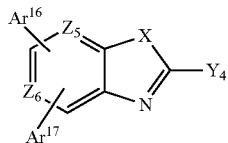

In the formula, $Ar^{16}$ and $Ar^{17'}$ may be the same or different from each other and each represent a hydrogen atom, a deuterium atom, a substituted or unsubstituted aromatic hydrocarbon group, a substituted or unsubstituted aromatic heterocyclic group, or a substituted or unsubstituted fused polycyclic aromatic group, $Y_4$ represents a substituted or unsubstituted aromatic hydrocarbon group, a substituted or unsubstituted aromatic heterocyclic group, a substituted or unsubstituted fused polycyclic aromatic group, a straight-chained or branched alkyl group that has 1 to 6 carbon atoms and may have a substituent group, a cycloalkyl group that has 5 to 10 carbon atoms and may have a substituent group, or a straight-chained or branched alkenyl group that has 2 to 6 carbon atoms and may have a substituent group, X represents an oxygen atom or a sulfur atom, and $Z_5$ and $Z_6$ may be the same or different from each other and each represent a carbon atom or a nitrogen atom; and
wherein the aromatic heterocyclic group of $Y_4$ is other than a carbazolyl group;

(Chem. 10)

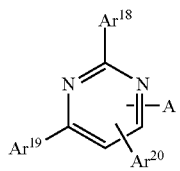

(ETM-2)

In the formula, $Ar^{18}$ represents a substituted or unsubstituted aromatic hydrocarbon group, a substituted or unsubstituted aromatic heterocyclic group, or a substituted or unsubstituted fused polycyclic aromatic group, $Ar^{19}$ and $Ar^{20}$ each represent a hydrogen atom, a deuterium atom, a substituted or unsubstituted aromatic hydrocarbon group, a substituted or unsubstituted aromatic heterocyclic group, or a substituted or unsubstituted fused polycyclic aromatic group, both $Ar^{19}$ and $Ar^{20}$ do not represent any of a hydrogen atom and a deuterium atom, and A represents a monovalent group represented by the following structural formula (ETM-A);

(Chem. 11)

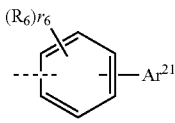

(ETM-A)

In the formula, a broken line represents a binding site, $Ar^{21}$ represents a substituted or unsubstituted aromatic heterocyclic group, $R_6$ represents a deuterium atom, a fluorine atom, a chlorine atom, a cyano group, a trifluoromethyl group, a straight-chained or branched alkyl group that has 1 to 6 carbon atoms and may have a substituent group, a cycloalkyl group that has 5 to 10 carbon atoms and may have a substituent group, a straight-chained or branched alkenyl group that has 2 to 6 carbon atoms and may have a substituent group, a substituted or unsubstituted aromatic hydrocarbon group, a substituted or unsubstituted aromatic heterocyclic group, or a substituted or unsubstituted fused polycyclic aromatic group, and $r_6$ represents an integer of 0 to 4; In a case where $r_6$ is an integer of two or more, a plurality of $R_6$ bonded to the same benzene ring may be the same or different from each other and $R_6$ and $Ar^{21}$ may be bonded to each other via a single bond, a substituted or unsubstituted methylene group, an oxygen atom, or a sulfur atom to form a ring.

8. The organic EL device according to claim 7, characterized in that
the hole transport layer has a two-layer structure of a first hole transport layer and a second hole transport layer, and the first hole transport layer is a triphenylamine derivative represented by the following general formula (HTM-1) or (HTM-2);

(Chem. 12)

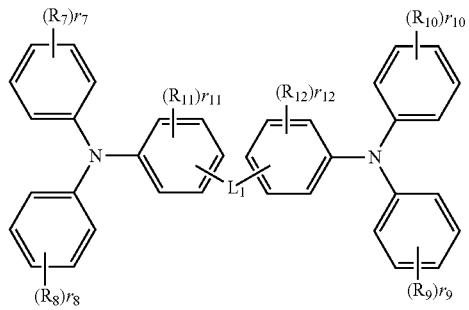

(HTM-1)

In the formula, each of $R_7$ to $R_{12}$ represents a deuterium atom, a fluorine atom, a chlorine atom, a cyano group, a nitro group, a straight-chained or branched alkyl group that has 1 to 6 carbon atoms and may have a substituent group, a cycloalkyl group that has 5 to 10 carbon atoms and may have a substituent group, a straight-chained or branched alkenyl group that has 2 to 6 carbon atoms and may have a substituent group, a straight-chained or branched alkyloxy group that has 1 to 6 carbon atoms and may have a substituent group, a cycloalkyloxy group that has 5 to 10 carbon atoms and may have a substituent group, a substituted or unsubstituted aromatic hydrocarbon group, a substituted or unsubstituted aromatic heterocyclic group, a substituted or unsubstituted fused polycyclic aromatic group, or a substituted or unsubstituted aryloxy group $r_7$ to $r_{12}$ may be the same or different from each other, $r_7$ to $r_{10}$ each represent an integer of 0 to 5, and $r_{11}$ and $r_{12}$ each represent an integer of 0 to 4; In a case where any of $r_7$ to $r_{12}$ is an integer of two or more, a plurality of $R_7$, a plurality of $R_8$, a plurality of $R_9$, a plurality of $R_{10}$ a plurality of $R_{11}$, or a plurality of $R_{12}$ bonded to the same benzene ring may be the same or different from each other; Further, a benzene ring and a substituent group substituted with a benzene ring, a plurality of substituent groups substituted with the same benzene ring, or benzene rings adjacent to each other via a nitrogen atom may be bonded to each other via a single bond, a substituted or unsubstituted methylene group, an oxygen atom, or a sulfur atom to form a ring; $L_1$ represents a bivalent group represented by the following structural formulae (HTM-A) to (HTM-F) or a single bond;

(Chem. 13)

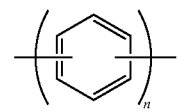

(HTM-A)

In the formula, n represents an integer of 1 to 3;

[Chem. 14]

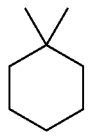

(HTM-B)

[Chem. 15]

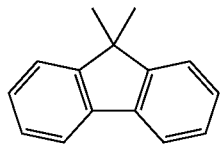

(HTM-C)

[Chem. 16]

—CH$_2$—

(HTM-D)

[Chem. 17]

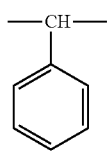

(HTM-E)

[Chem. 18]

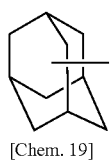

(HTM-F)

[Chem. 19]

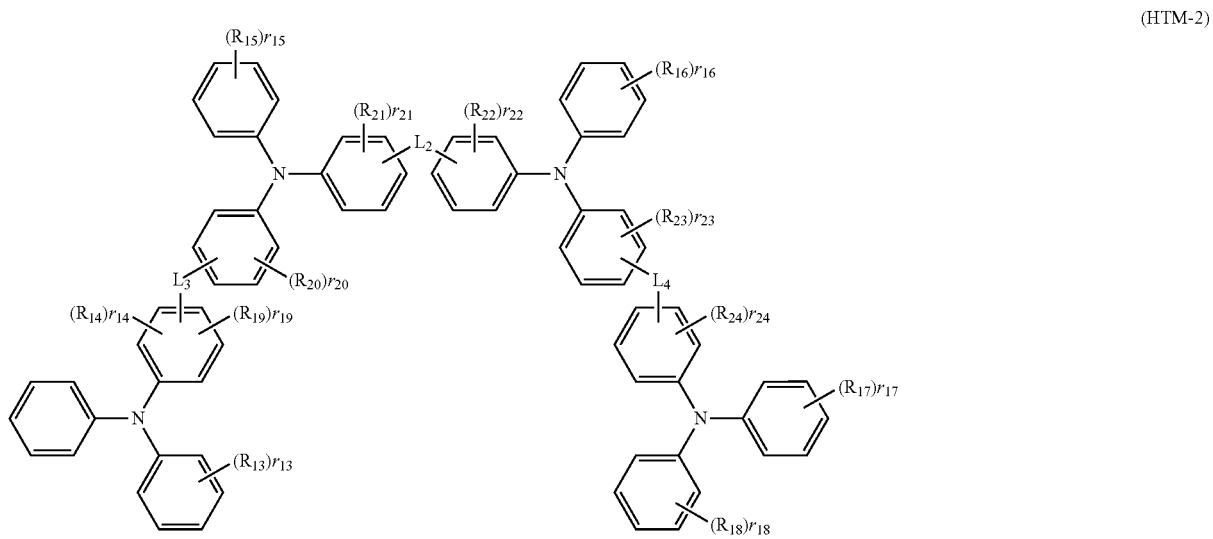

(HTM-2)

In the formula, R$_{13}$ to R$_{24}$ each represent a deuterium atom, a fluorine atom, a chlorine atom, a cyano group, a nitro group, a straight-chained or branched alkyl group that has 1 to 6 carbon atoms and may have a substituent group, a cycloalkyl group that has 5 to 10 carbon atoms and may have a substituent group, a straight-chained or branched alkenyl group that has 2 to 6 carbon atoms and may have a substituent group, a straight-chained or branched alkyloxy group that has 1 to 6 carbon atoms and may have a substituent group, a cycloalkyloxy group that has 5 to 10 carbon atoms and may have a substituent group, a substituted or unsubstituted aromatic hydrocarbon group, a substituted or unsubstituted aromatic heterocyclic group, a substituted or unsubstituted fused polycyclic aromatic group, or a substituted or unsubstituted aryloxy group; $r_{13}$ to $r_{24}$ may be the same or different from each other, $r_{13}$ to $r_{18}$ each represent an integer of 0 to 5, and $r_{19}$ to $r_{24}$ each represent an integer of 0 to 4; In a case where any of $r_{13}$ to $r_{24}$ is an integer of two or more, a plurality of $R_{13}$, a plurality of $R_{14}$, a plurality of $R_{15}$, a plurality of $R_{16}$, a plurality of $R_{17}$, a plurality of $R_{18}$, a plurality of $R_{19}$, a plurality of $R_{20}$, a plurality of $R_{21}$, a plurality of $R_{22}$, a plurality of $R_{23}$, or a plurality of $R_{24}$ bonded to the same benzene ring may be the same or different from each other; Further, a benzene ring and a substituent group substituted with a benzene ring, a plurality of substituent groups substituted with the same benzene ring, or benzene rings adjacent to each other via a nitrogen atom may be bonded to each other via a single bond, a substituted or unsubstituted methylene group, an oxygen atom, or a sulfur atom to form a ring; $L_2$ to $L_4$ may be the same or different from each other, and each represent a bivalent group represented by the following structural formulae (HTM-A) to (HTM-F) or a single bond.

\* \* \* \* \*